United States Patent
Ahluwalia

(10) Patent No.: US 10,639,072 B2
(45) Date of Patent: *May 5, 2020

(54) UTERINE MANIPULATOR

(71) Applicant: Prabhat Kumar Ahluwalia, Little Falls, NY (US)

(72) Inventor: Prabhat Kumar Ahluwalia, Little Falls, NY (US)

( * ) Notice: Subject to any disclaimer, the term of this patent is extended or adjusted under 35 U.S.C. 154(b) by 417 days.

This patent is subject to a terminal disclaimer.

(21) Appl. No.: 15/347,904

(22) Filed: Nov. 10, 2016

(65) Prior Publication Data

US 2017/0112535 A1 Apr. 27, 2017

Related U.S. Application Data

(63) Continuation of application No. 14/204,766, filed on Mar. 11, 2014, now Pat. No. 9,522,252.

(60) Provisional application No. 61/777,350, filed on Mar. 12, 2013.

(51) Int. Cl.
| | |
|---|---|
| *A61B 17/42* | (2006.01) |
| *A61M 25/00* | (2006.01) |
| *A61B 90/50* | (2016.01) |
| A61B 90/00 | (2016.01) |
| A61B 90/57 | (2016.01) |
| A61B 17/00 | (2006.01) |

(52) U.S. Cl.
CPC .......... *A61B 17/4241* (2013.01); *A61B 90/50* (2016.02); *A61M 25/0068* (2013.01); *A61B 2017/00455* (2013.01); *A61B 2017/00557* (2013.01); *A61B 2017/00738* (2013.01); *A61B 2017/00862* (2013.01); *A61B 2090/0801* (2016.02); *A61B 2090/0807* (2016.02); *A61B 2090/571* (2016.02); *A61M 2025/0073* (2013.01)

(58) Field of Classification Search
CPC ............ A61B 17/4241; A61M 25/001; A61M 25/0067; A61M 25/0068; A61M 25/007
USPC ....................................................... 606/119
See application file for complete search history.

(56) References Cited

U.S. PATENT DOCUMENTS

| | | | | |
|---|---|---|---|---|
| 845,249 | A * | 2/1907 | Morris ................... | A61M 25/04 604/104 |
| 5,540,700 | A * | 7/1996 | Rowden ............. | A61B 17/4241 600/201 |
| 6,773,418 | B1* | 8/2004 | Sharrow ............... | A61M 3/027 600/201 |
| 2005/0277948 | A1* | 12/2005 | Cedars ................... | A61B 17/42 606/119 |
| 2010/0106163 | A1* | 4/2010 | Blair ................... | A61B 17/4241 606/119 |
| 2010/0331859 | A1* | 12/2010 | Omori ................ | A61B 17/4241 606/130 |
| 2011/0259344 | A1* | 10/2011 | Ahluwalia ................ | A61F 6/06 128/834 |

* cited by examiner

*Primary Examiner* — Martin T Ton
(74) *Attorney, Agent, or Firm* — Pierson IP, PLLC

(57) ABSTRACT

An embodiment includes a uterine manipulator system comprising: a collar including a first shelf connected to the inner surface of the collar; a stabilizer including a stabilizer rim adapted to couple to the first shelf; and a shaft adapted to pass through the stabilizer and a hollow tunnel of the collar with a bulbous tip. Other embodiments are described herein.

19 Claims, 38 Drawing Sheets

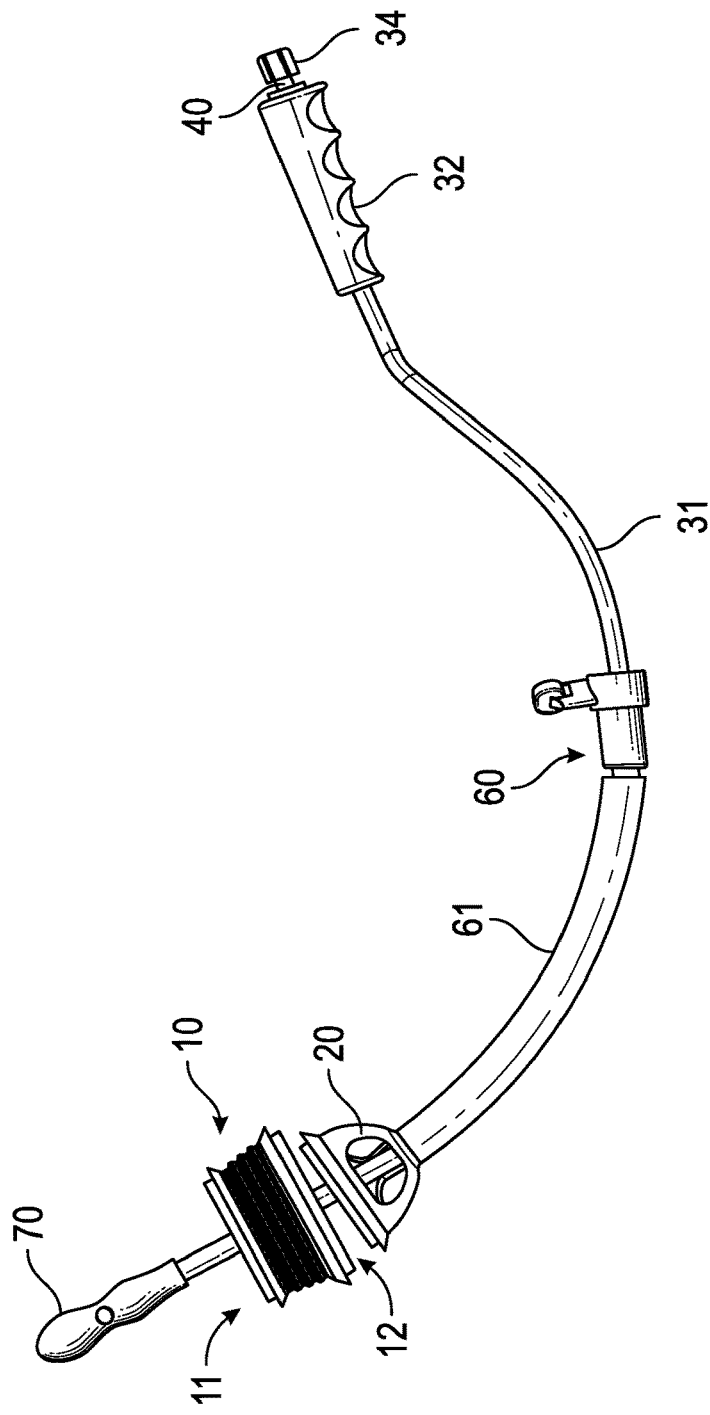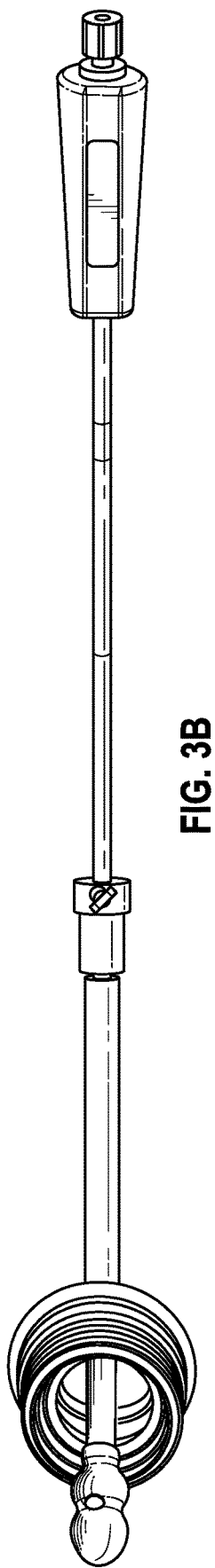
FIG. 3A
FIG. 3B

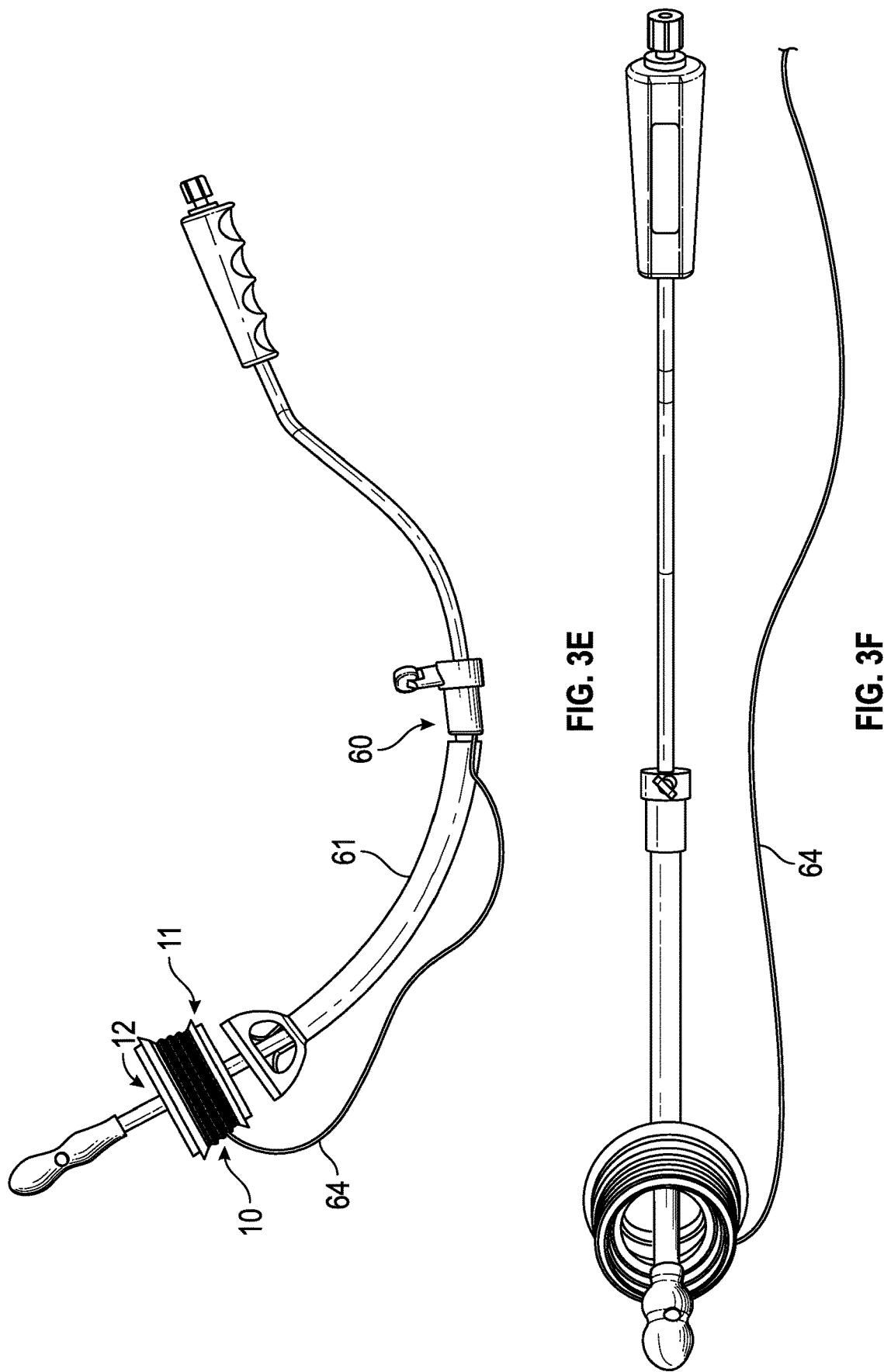

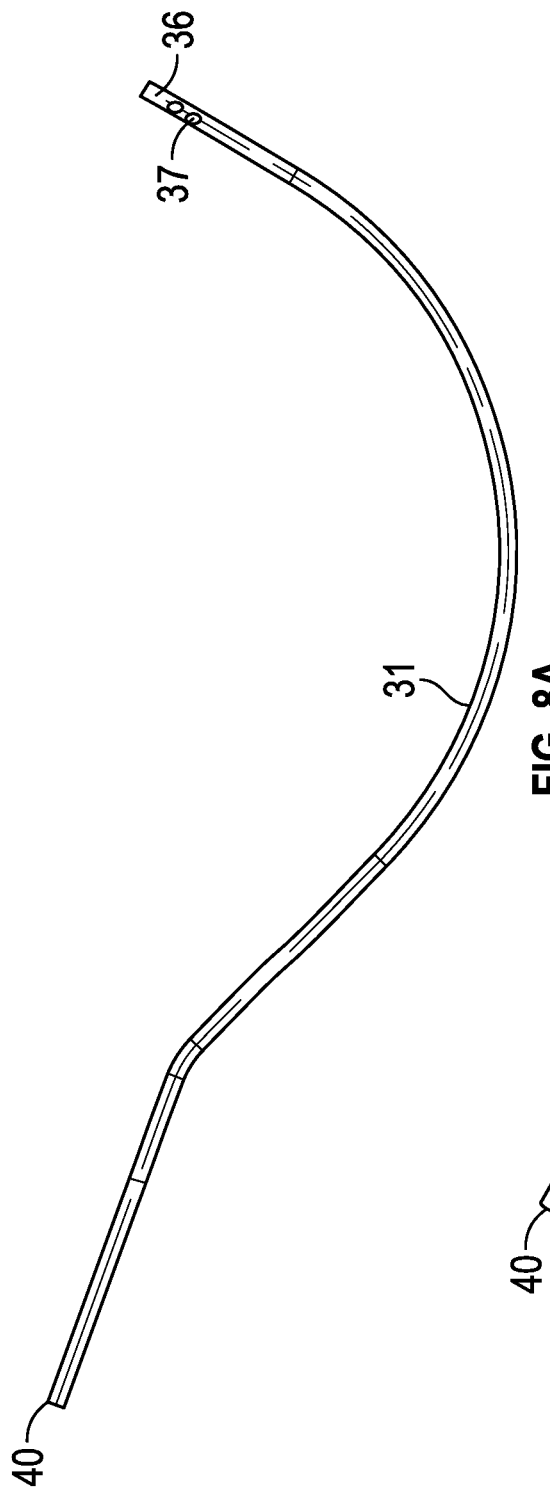
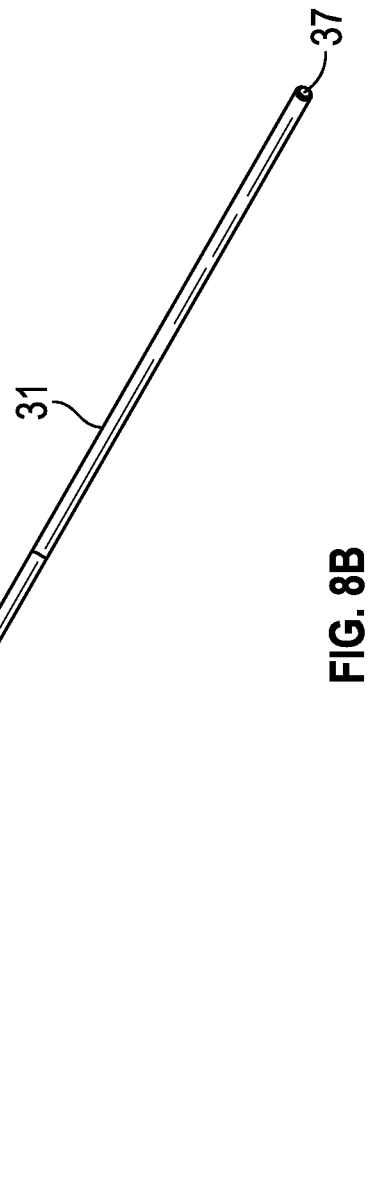
FIG. 8A
FIG. 8B

US 10,639,072 B2

UTERINE MANIPULATOR

This application claims priority to U.S. Provisional Patent Application Ser. No. 61/777,350 filed on Mar. 12, 2013, the content of which is hereby incorporated by reference. This application also is a continuation of and claims a benefit under 35 U.S.C. § 120 of prior filed Non-Provisional application Ser. No. 14/204,766 filed on Mar. 11, 2014, the content of which is hereby incorporated by reference

BACKGROUND

U.S. patent application. Publication Ser. No. 13/091,517, entitled FORNIX MANIPULATOR and filed on Apr. 21, 2011 ('517 application), shares a common inventor with the present application. The '517 application discloses a fornix manipulator including a collar and stabilizer to be attached to a uterine shaft. The fornix manipulator addresses several problems, including imprecise fornix delineation and deviation; vaginal shortening; abdominal deflation; blocked cervical access; unnecessary tissue damage from blind cervical retrieval, device insertion and retrieval, and lack of a platform for organ dissection.

BRIEF DESCRIPTION OF DRAWINGS

The accompanying drawings are included to provide a further understanding of the general inventive concept and are incorporated in and constitute a part of this specification. The drawings illustrate exemplary embodiments of the general inventive concept and, together with the description, serve to explain principles of the general inventive concept. Features and advantages of embodiments of the present invention will become apparent from the appended claims, the following detailed description of one or more example embodiments, and the corresponding figures:

FIGS. 3A-3H illustrate embodiments of a uterine manipulator, where either end of the collar is being employed as the receiving end.

FIGS. 4E-4F illustrate cross-sectional views of alternative embodiments of a collar.

FIGS. 8A-8H illustrate embodiments of a uterine shaft, embodiments of a dye delivery system, embodiments of an adolescent uterine manipulator system, and embodiments of an adult uterine manipulator system.

DETAILED DESCRIPTION

Preferred embodiments of the general inventive concept will be described below in more detail with reference to the accompanying drawings. These embodiments are provided so that this disclosure will be thorough and complete, and will convey the scope of the general inventive concept to those skilled in the art. The embodiments of the general inventive concept may, however, be embodied in different forms and should not be constructed as limited to the embodiments set forth herein. Although numerous specific details are set forth, embodiments of the invention may be practiced without these specific details. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. Like numbers refer to like elements throughout. Well-known structures and techniques have not been shown in detail to avoid obscuring an understanding of this description.

An embodiment of the invention includes an improvement to uterine manipulators and dye delivery systems that addresses several issues, such as minimizing surgical error, facilitating dye delivery, fostering easy manipulation of a patient's anatomy, and/or reducing healthcare and hospital costs. An embodiment includes a uterine manipulator having a collar, stabilizer, uterine shaft, outer tube, pressing portion, handle, and/or special tip. Another embodiment includes a dye delivery system having a uterine shaft and special tip. However, embodiments are not limited to addressing these issues, and other benefits, features, and/or utilities may be apparent to one of ordinary skill in the art.

Figure 1:
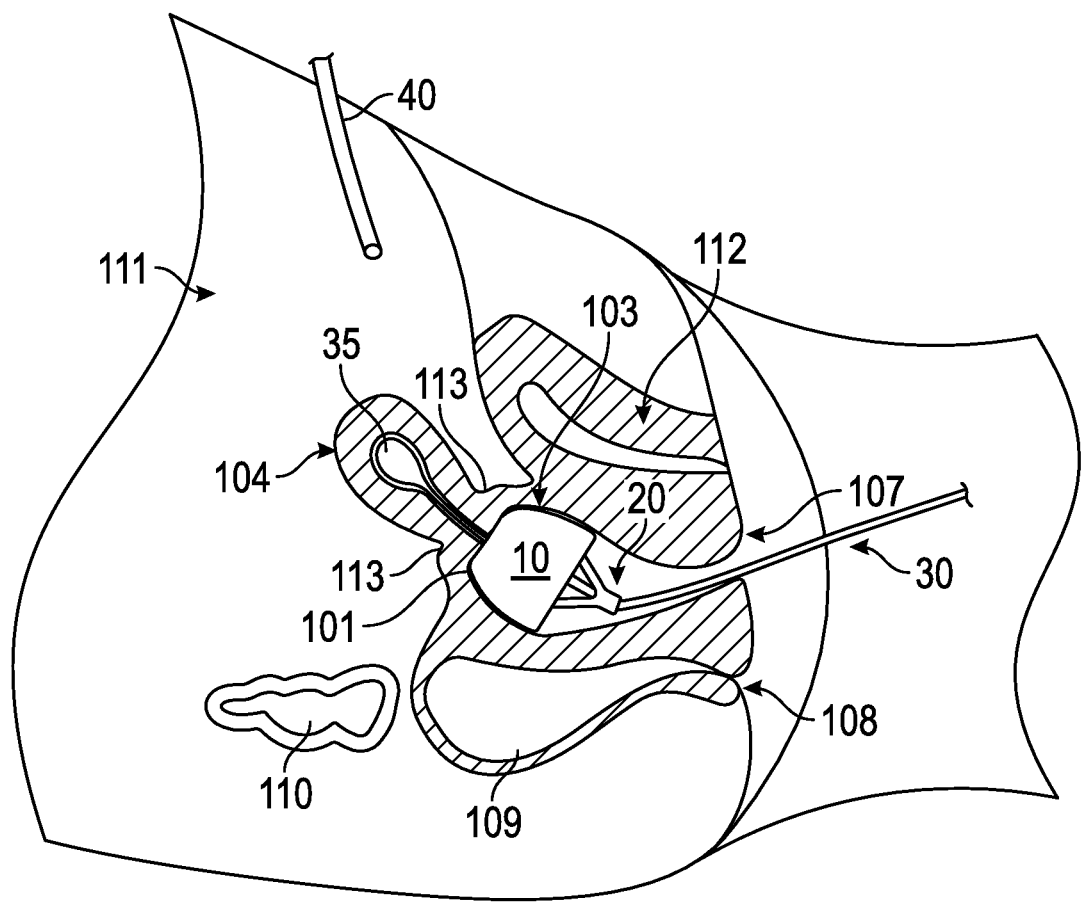
FIG. 1 illustrates a conventional uterine manipulator from the 571' application.

FIG. 1 shows a schematic of a uterine manipulator 30, including a collar 10, stabilizer 20, and balloon tip 35 from the '571 application. More specifically, FIG. 1 shows a sagittal cross-section of a female pelvis. The cervix opens into the uterus 104. On one side of the vagina 107, toward the front of the body, is a bladder 112. On another side of the vagina 107, toward the rear of the body, is the rectum 109 between intestines 110 and the anus 108, which opens from the rectum 109 to outside the body. Surgeons may access the uterus 104 and other organs from the abdominal cavity 111. The fornix is a cylindrical ring of tissue encircling the cervix and lower uterus. The lowest cylindrical ring is the intravaginal fornix 101, which encircles the cervix and is visible from the vaginal canal. The upper-most cylindrical ring of the fornix is the intra-abdominal fornix 113. When viewed from the abdomen, the anterior half of the intra-abdominal fornix 113 may be visible, but it is neither demarcated nor obvious to the human eye. The ring of the intra-abdominal fornix 113 passes between the uterus 104 and rectum 109, and also passes between the uterus 104 and bladder 112, as indicated by FIG. 1.

Several problems and injuries may result when using conventional devices, known as uterine manipulators, to manipulate the fornix. These problems include imprecise fornix delineation and deviation; vaginal shortening; and abdominal deflation. Injury can also result from blocked cervical access and blind cervical retrieval; device insertion and retrieval; and lack of a platform while dissecting vital organs away from the fornix and vaginal wall.

Figure 2A:
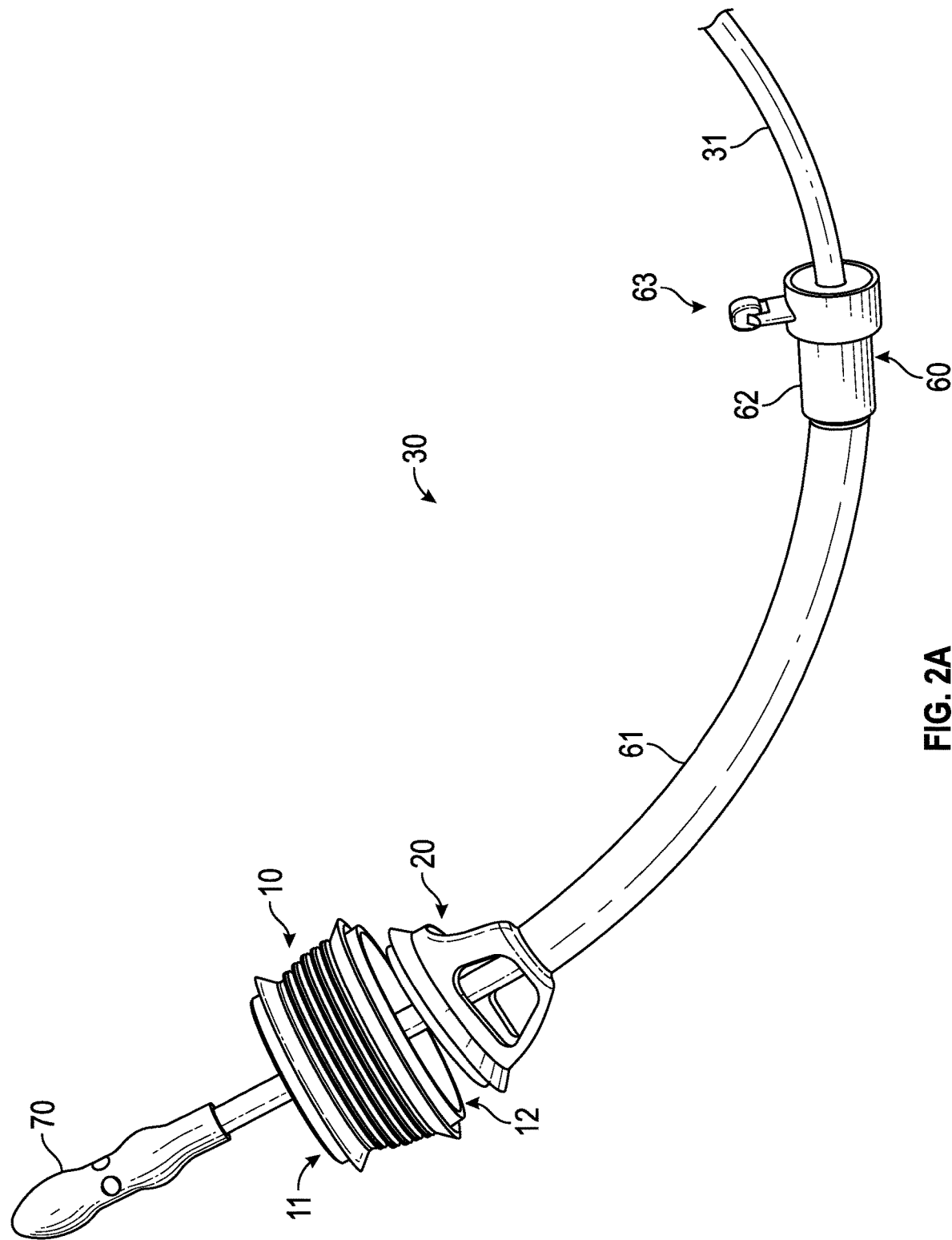
FIGS. 2A-2B illustrate embodiments of a uterine manipulator containing a uterine shaft, tip, collar, stabilizer, and a pressing portion including an outer tube, fixing portion, and screw.
Figure 2B:
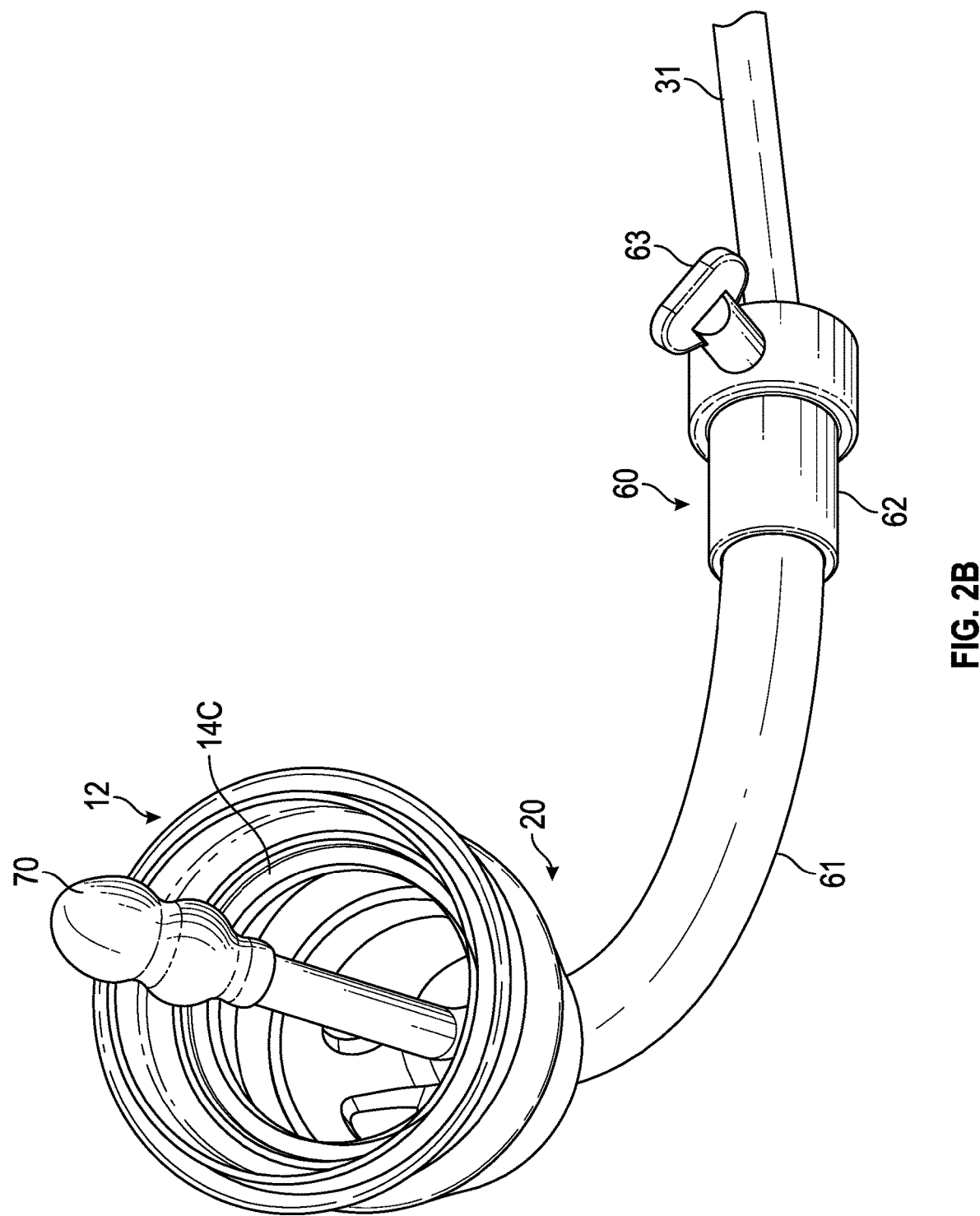

FIGS. 2A-2B illustrate an embodiment from two different angles. Uterine manipulator 30 includes a uterine shaft 31, tip 70, collar 10, stabilizer 20, an outer tube 61, and a pressing portion 60, comprising of a fixing portion 62 and screw 63 (e.g., set screw). In FIG. 2A, smaller diameter end 11 of the collar 10 is the receiving end for the cervix. In FIG. 2B, larger diameter end 12 of the collar 10 is the receiving end for the cervix. In other words, collar 10 is reversible.

FIGS. 3A-3D and 3E-3H illustrate an embodiment of a uterine manipulator 30 from four perspectives including a handle 32, inlet 40, cap 34, uterine shaft 31, tip 70, collar 10, stabilizer 20, an outer tube 61, and a pressing portion 60. In FIGS. 3A-3D, end 11 of the collar 10 is the receiving end for the cervix. In FIGS. 3E-3H, end 12 of the collar 10 is the receiving end for the cervix. In other words, collar 10 is reversible.

Dual-Use Collar

Figure 4A:
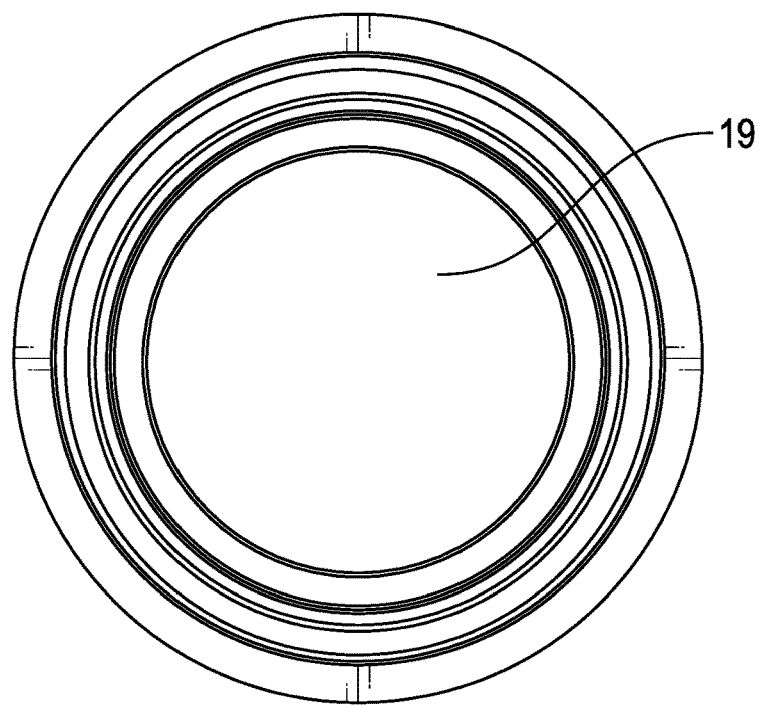
FIGS. 4A-4F illustrate three perspectives of an embodiment of a collar in addition to a cross-sectional view.
Figure 4B:
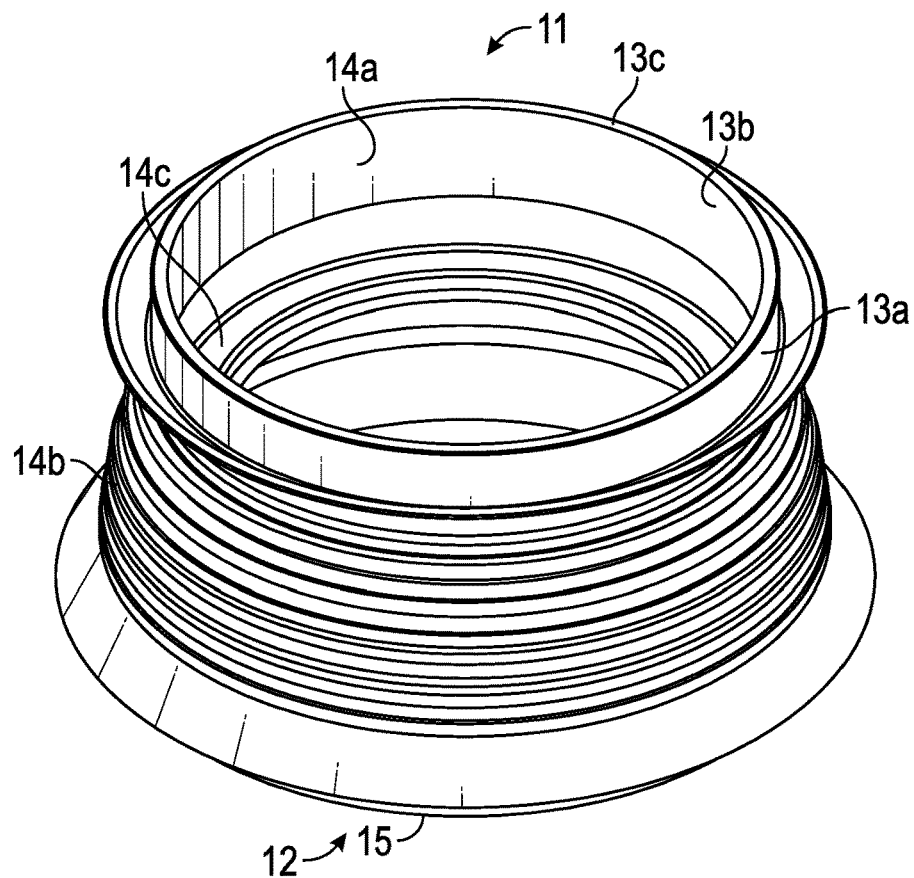
Figure 4C:
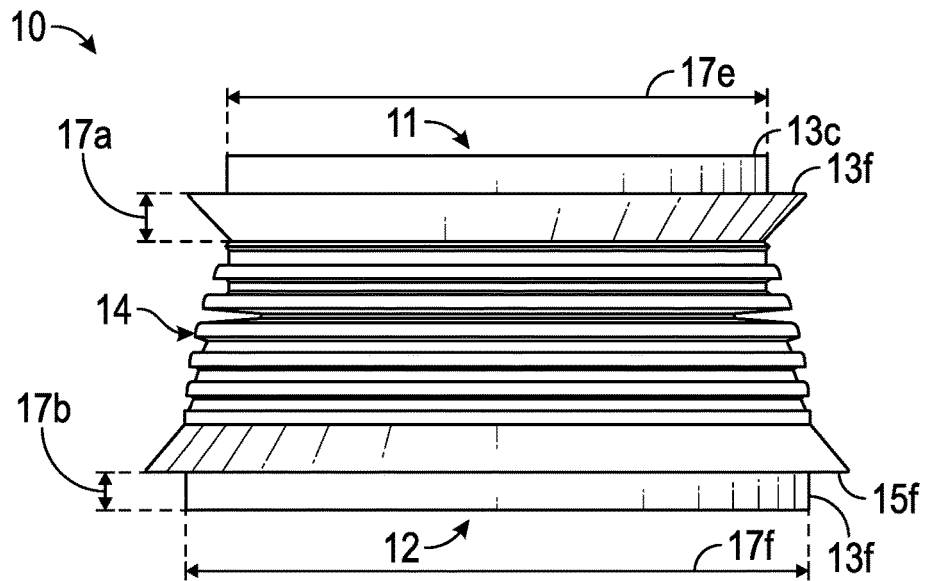
Figure 4D:
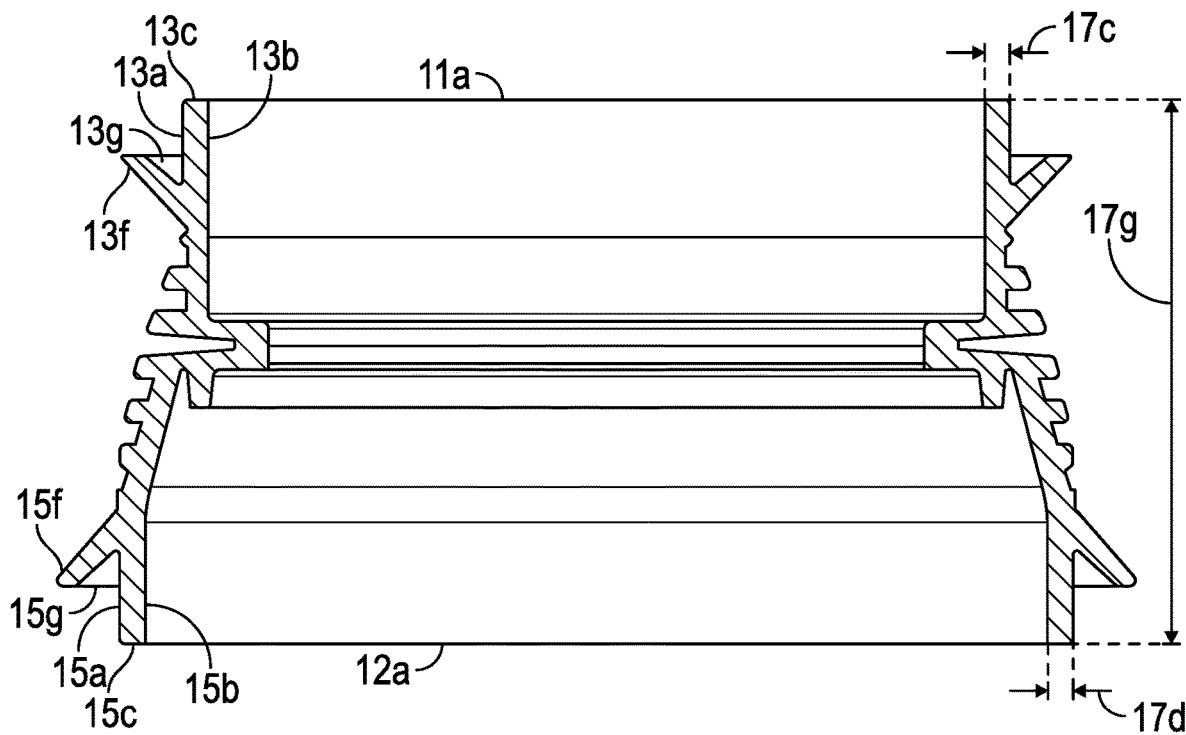

FIGS. 4A-4D illustrate a shape of a collar 10 in an embodiment. FIG. 4A is a top view of an embodiment of the collar 10, FIG. 4B is a perspective view, FIG. 4C is a side view, and FIG. 4D is a cross-sectional view of FIG. 4C.

The collar 10 includes two ends 11 and 12, the diameter of end 12 exceeding the diameter of end 11. A sidewall 14 defines a profile of the collar 10 with an inner surface 14a and outer surface 14b. The sidewall also defines an opening 11a of the end 11 and another opening 12a of the opposite end 12. Between the openings 11a and 12a, the sidewall 14 also defines an inner cavity 19 and is ribbed with ridges 9. The sidewall may be smooth, have even ridges, or uneven ridges of varying width and size. The sidewall may be of even or uneven density.

The opening of 11a is defined by a rim 13 having an outer edge 13a, an inner edge 13b, and a rim surface 13c between the outer and inner edges 13a and 13b. The collar 10 may also include a second outer rim edge 13f separated by a trough or gully 13g. Additional rim edges may be added as needed (e.g., 2, 3, 4, 5 or more).

In addition, the collar is dual-rimmed. Just as opening 11a is defined by a rim 13, so is the opening 12a defined by a rim 15. The rim has an outer edge 15a, an inner edge 15b, and a rim surface 15c between the outer and inner edges 15a and 15b. It may also have a second outer rim edge 15f separated by a trough or gully 15g. Additional rim edges may be added as needed (e.g., 2, 3, 4, 5 or more). The '517 application describes a variety of rim shapes and configurations applicable to rim 13 of end 11, depicted also in many of the figures. These shapes and configurations are also applicable to rim 15 of end 12. In addition, although the collar is described as double-rimmed, it may also be single rimmed. The number of rims on one end of the collar need not correspond to the number of rims on the other end.

Cervixes have different lengths, diameter and shapes. Surgeons may delineate and manipulate the fornix using either rim 15 of end 12, or rim 13 of end 11, depending on which end more snuggly or appropriately fits around the cervix. In other words, end 12 or end 11 of collar 10 may serve as a receiving end of the collar that slides over the cervix and contacts the intra-vaginal fornix.

In the embodiment shown in FIG. 4A-4D, the surgeon has two alternative diameters to fit onto the cervix—the diameter of end 11 defined by rim element 13c or alternatively, the larger diameter of end 12 defined by rim element 15c. Because there is variation in cervical size across patients, both ends being the possible receiving end saves hospitals and surgeons substantial time and cost. Instead of trials with multiple collars, surgeons need only experiment with either side of one collar.

In addition to reducing surgical time and cost, the dual-rimmed collar reduces the risk of surgical error resulting from over-estimating the cervical size. Surgeons may overestimate the size of the cervix due to optical illusions. In particular, the vaginal wall and tissue surrounding the cervix may mislead the surgeon to believe the cervix is larger than it is. However, with a dual-rimmed collar, a surgeon who believes the cervix is large in diameter may apply the larger end 12 as the receiving end. She may also test her assumption by trying the reverse smaller end (end 11) to determine if she overestimated the cervical diameter. If overestimated, she may use the smaller end.

The dual-rimmed collar does not complicate insertion or retrieval. Even if the larger diameter end 12 is to be used as the receiving end, the smaller diameter end 11 may be inserted in the vaginal canal first, allowing the vaginal opening to expand to the larger diameter as the device is inserted. Once the collar is within the vaginal canal, the surgeon may rotate the device within the vaginal canal and slide the appropriate end over the cervix. If the end is too large or too small in diameter for the cervix, the surgeon may slide the collar 10 off the cervix, rotate the device, and slide the other end onto the cervix. Alternatively, the device may be inserted sideways, so the sidewall 14 is inserted first.

Repeated trials indicate that in some embodiments, the distances 17a and 17b between the rim edges 13c and 13f, and 15c and 15f, respectively, may be 0-2 mm, 2-4 mm, 4-6 mm, or 6-8 mm. In some embodiments, the distances 17c and 17d between the rim edges 13a and 13b, and 15a and 15b, respectively, may be 0-2 mm or 2-4 mm. In some embodiments, the diameter 17e of end 11 may be between 15-20 mm, 20-25 mm, or 25-30 mm, 30-35 mm, or 35-40 mm, or 40-45 mm. In some embodiments, the diameter 17f of end 12 may be between 20-25 mm, 25-30 mm, 30-35 mm, 35-40 mm, or 40-45 mm. In some embodiments, the distance 17g between end 11 and end 12 may be between 5-10 mm, 10-15 mm, 15-20 mm, 20-25 mm, 25-30 mm, 30-35 mm, or 35-40 mm. The diameter may be 40 mm or more for women who have undergone natural childbirth.

Figure 3C:
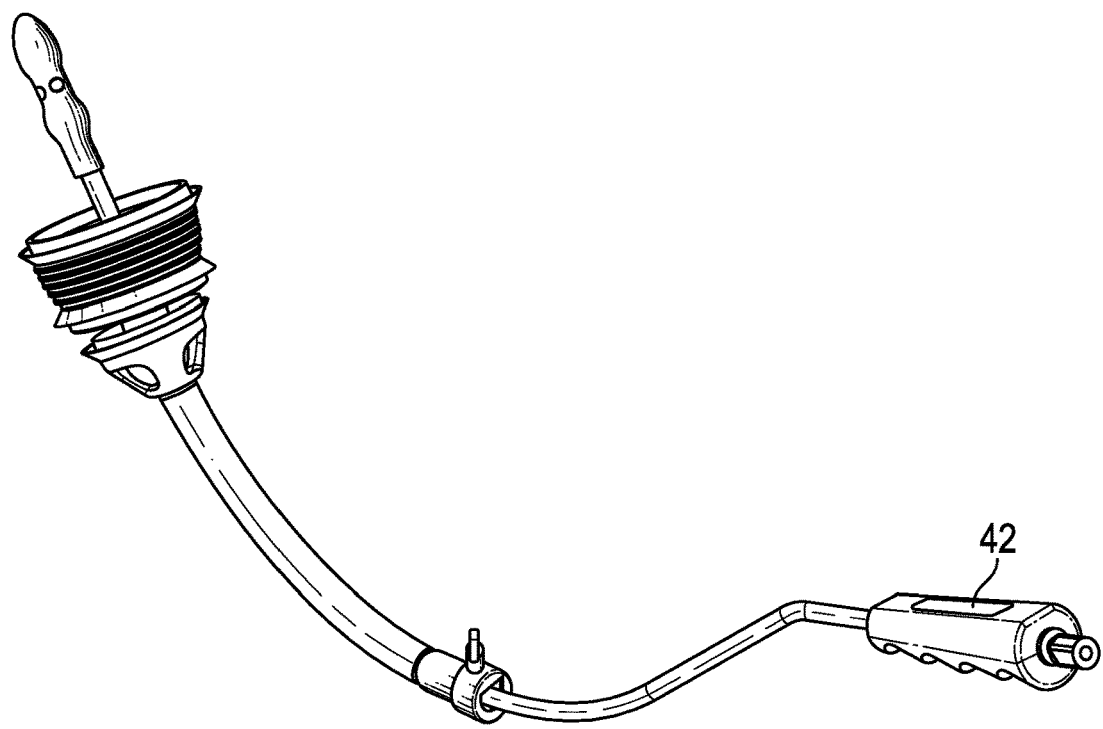
Figure 3D:
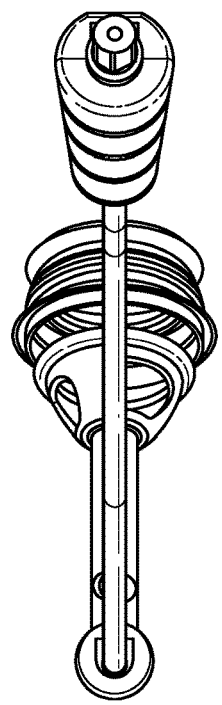
Figure 3G:
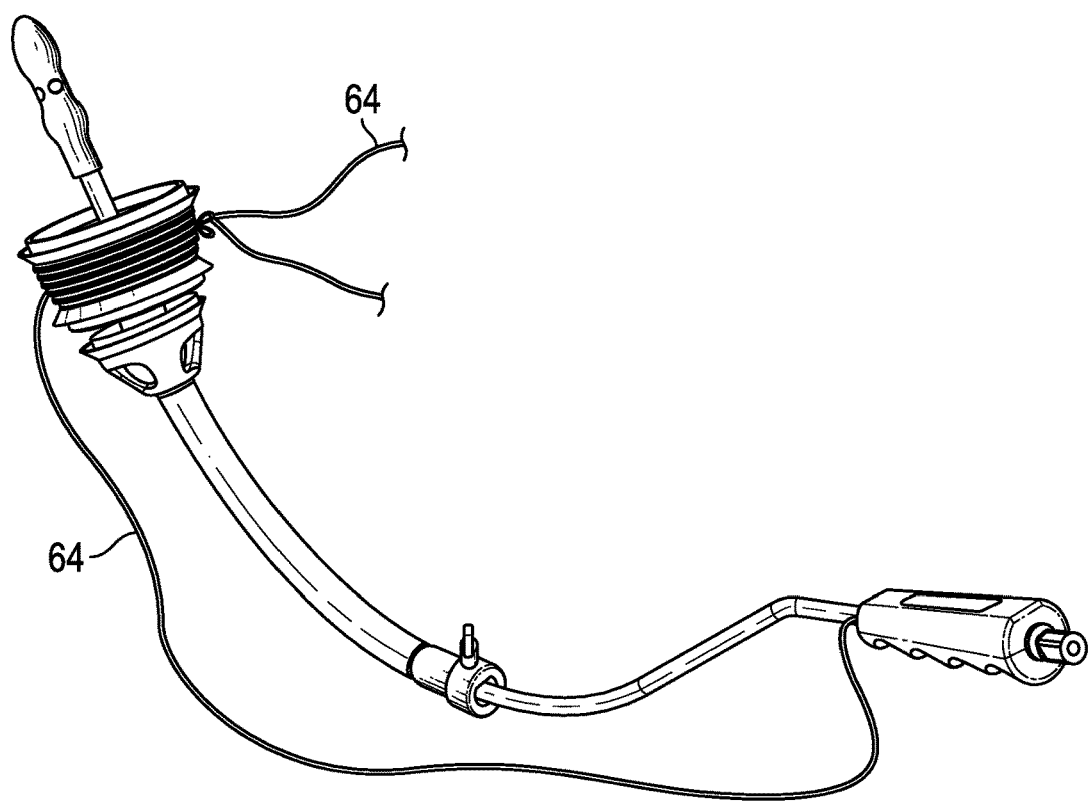
Figure 3H:
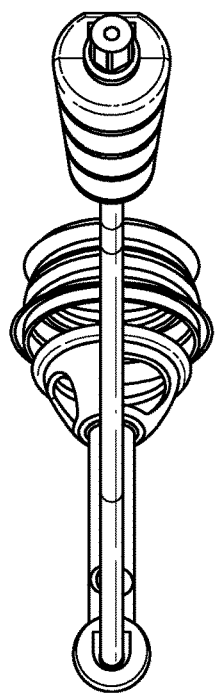
Figure 13A:
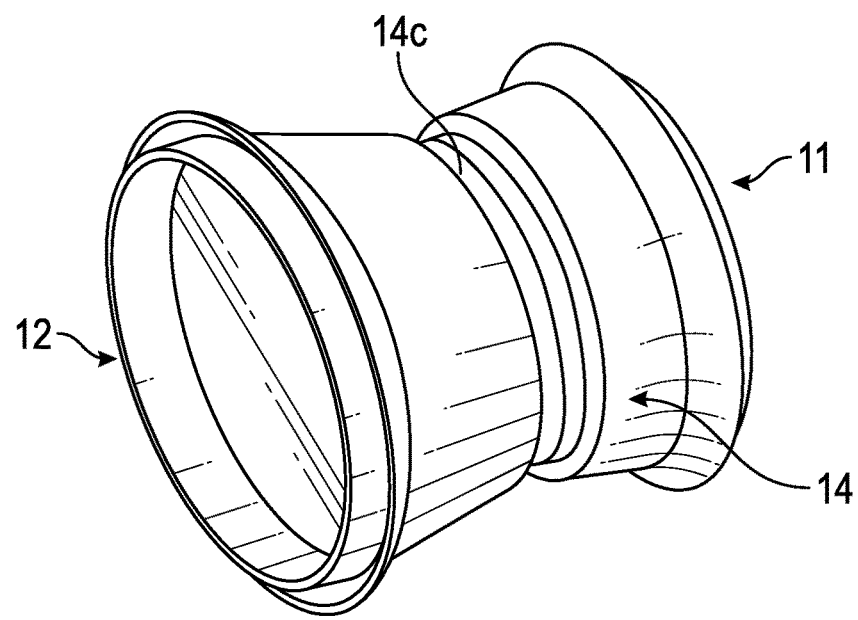
FIGS. 13A-13C illustrate embodiments of a collar.
Figure 13B:
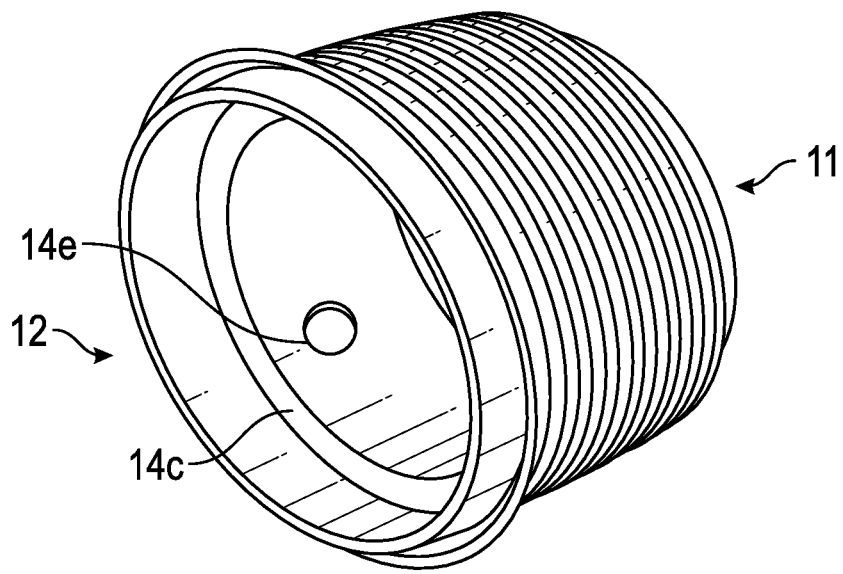

A string, mesh, or strap (hereinafter "strap") 64 may connect between the collar 10 and the outer tube 61, pressing portion 60, shaft 31, handle 32 or any part of the uterine manipulator 30 to allow easy removal of the collar 10 along with the uterine manipulator 30, as shown in FIGS. 3E and 3G. The collar 10 may include a hole 14e along the side wall 14 or either collar end 11 or end 12, as shown in FIG. 13B. The strap 64 may be connected to the hole 14e via a ring, knot, a tie, glue, or any other means. Alternatively, the strap may be tied around the diameter of the collar's sidewalls 14, as shown in FIG. 3G. In another embodiment, the strap 64 is connected to the collar 10 but does not connect to any other portion of the uterine manipulator system and instead hangs loosely, inside our outside the vaginal canal, as shown in FIG. 3F.

Dual-Use Collar for Universal Stabilizer

Each collar 10 may use a stabilizer 20 in some embodiments to further delineate the fornix. When the end 26 of stabilizer 20 is pressed against an end or rim of collar 10, the collar 10 delineates the fornix intra-abdominally. However, if the collar is dual-use and the diameters of the collar end 12 and collar end 11 are different, then the stabilizer must be made in two different sizes, with two diameters corresponding to the respective diameters of collar ends 11 and 12, or alternatively rim 13 and 15 if the stabilizer is configured to press against the collar's rim. This is costly and cumbersome.

FIGS. 5A-5D illustrate an embodiment wherein a single universal stabilizer 20 may be used to stabilize either end of the collar 10. In this embodiment, the collar 10 contains an inner ridge, ledge, shelf, abutment, rim, ring, protrusion, or shelf (hereinafter "shelf") 14c located between collar end 12 and collar end 11 and in communication with or coupled to wall 14. FIG. 4B and cross-section 4D also show a shelf 14c placed at the midpoint of the collar 10.

Figure 5A:
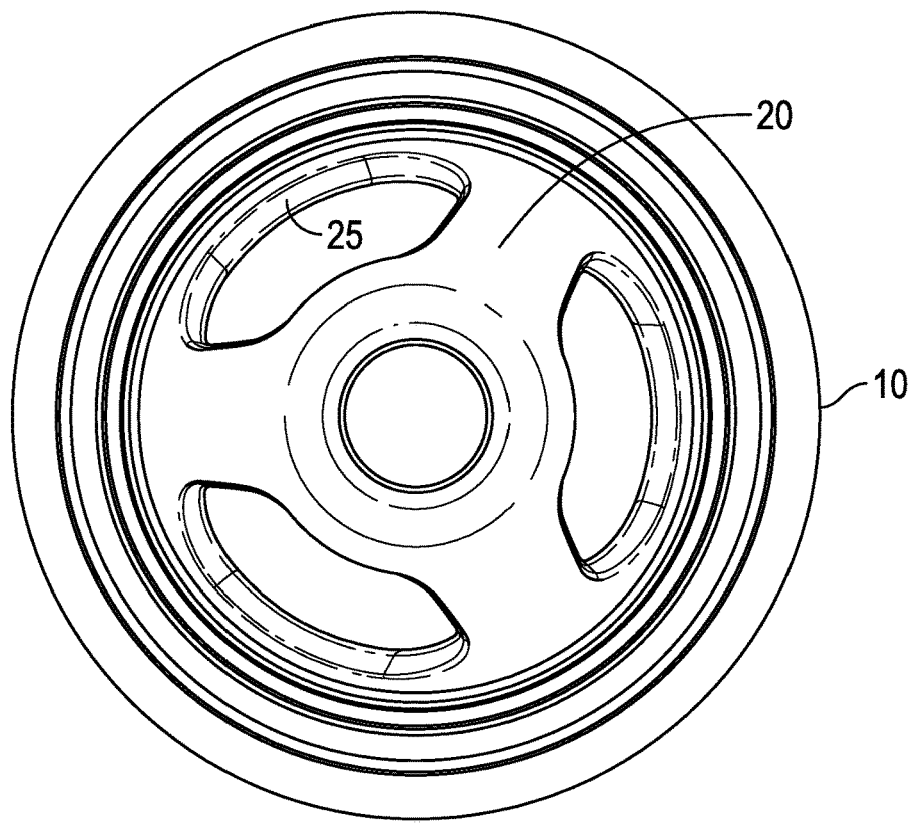
FIGS. 5A-5D illustrate an embodiment of a stabilizer fitted into either end of a collar.
Figure 5B:
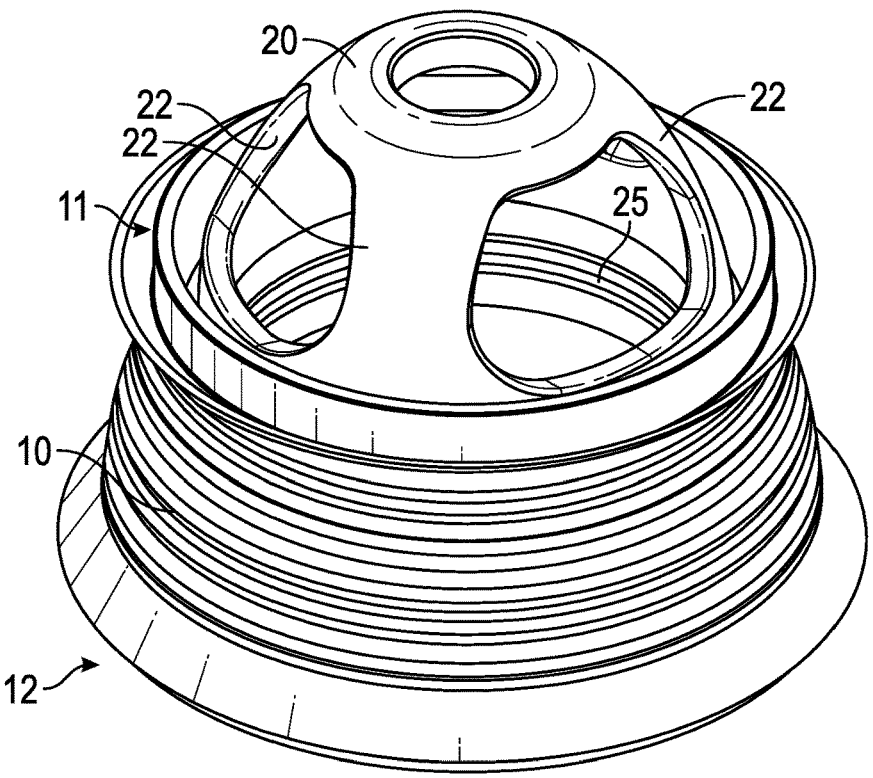
Figure 5C:
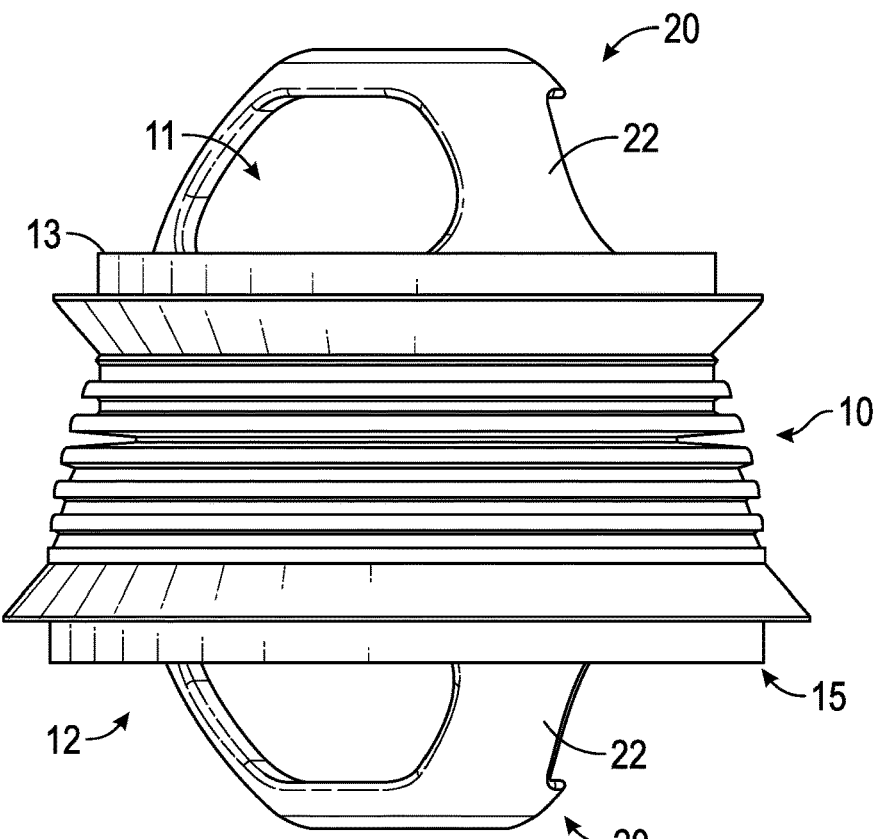

FIG. 5A is a top-down view of an embodiment where the stabilizer end 26 is inserted into collar end 11 and pressed against the collar's inner shelf 14c. FIG. 5B is a perspective view. FIG. 5C shows that an embodiment of stabilizer 20 may be inserted into either end 11 or end 12 of collar 10. Specifically, rim 25 of stabilizer 20 may snap, slide, lock into or simply presses against either side of the shelf 14c. In other embodiments, the arms 22 of the stabilizer—whether unified by a rim or not—may snap, fit or stop into or onto the inner shelf 14c from either end of the collar, depending on which end the surgeon chooses to use a receiving end to contact the cervix.

Figure 5D:
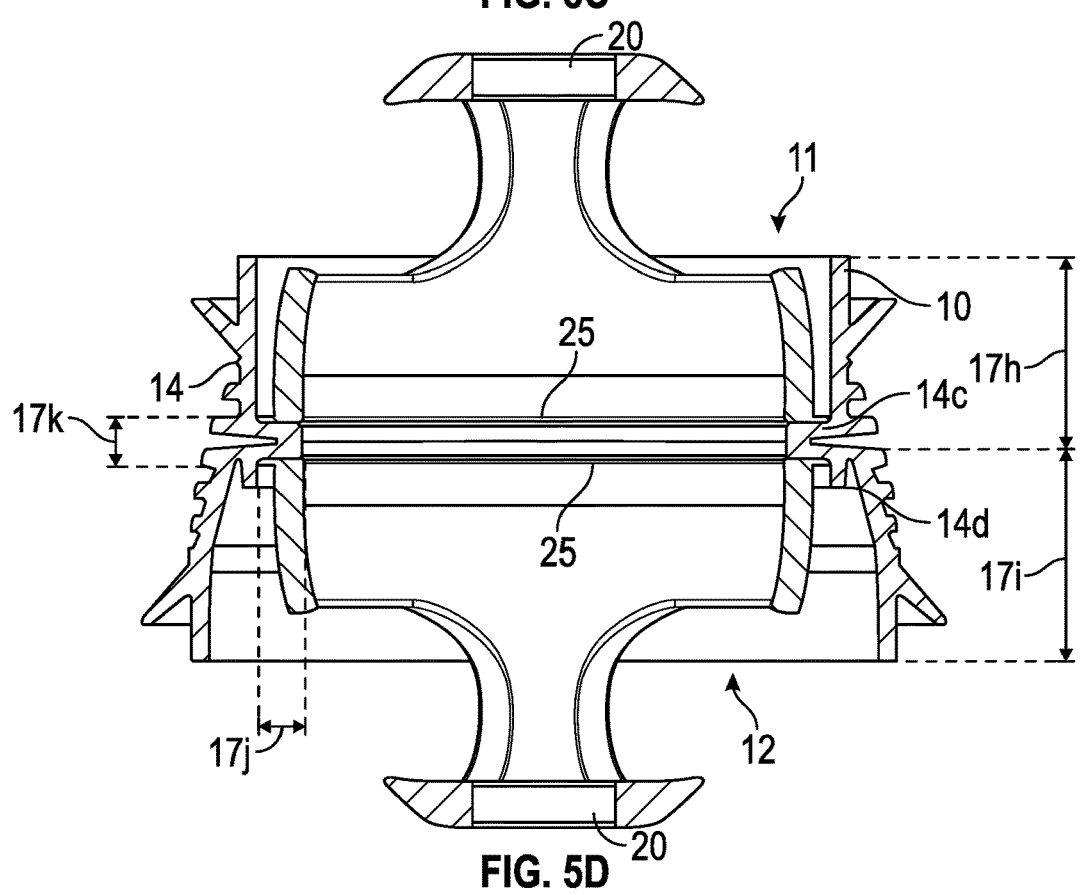

FIG. 5D shows a cross-section of FIG. 5C wherein one stabilizer 20 abuts one face of shelf 14c while another stabilizer 20 abuts the opposite face of shelf 14c. The illustration of two stabilizers at once abutting either face of the shelf 14c in FIGS. 5C and 5D is only to illustrate how a single stabilizer end 26 may press against shelf 14c from either end 11 or end 12 of collar 10, not to show that two stabilizers are used simultaneously. Thus, only one stabilizer is needed, instead of two, which reduces hospital and surgical costs.

As shown in FIG. 5D, shelf 14c may be located at any point between the ends 11 and 12, including but not limited to the midpoint of the side wall 14. When the shelf 14c is located near or at the midpoint of wall 14 as shown in FIGS. 5A-5D, the rim 25 or prongs 22 of the stabilizer 20, whether unified by a rim 25 or not, may fit into, contact, or press against either side of the shelf 14c on the interior sidewall 14a.

Figure 4E:
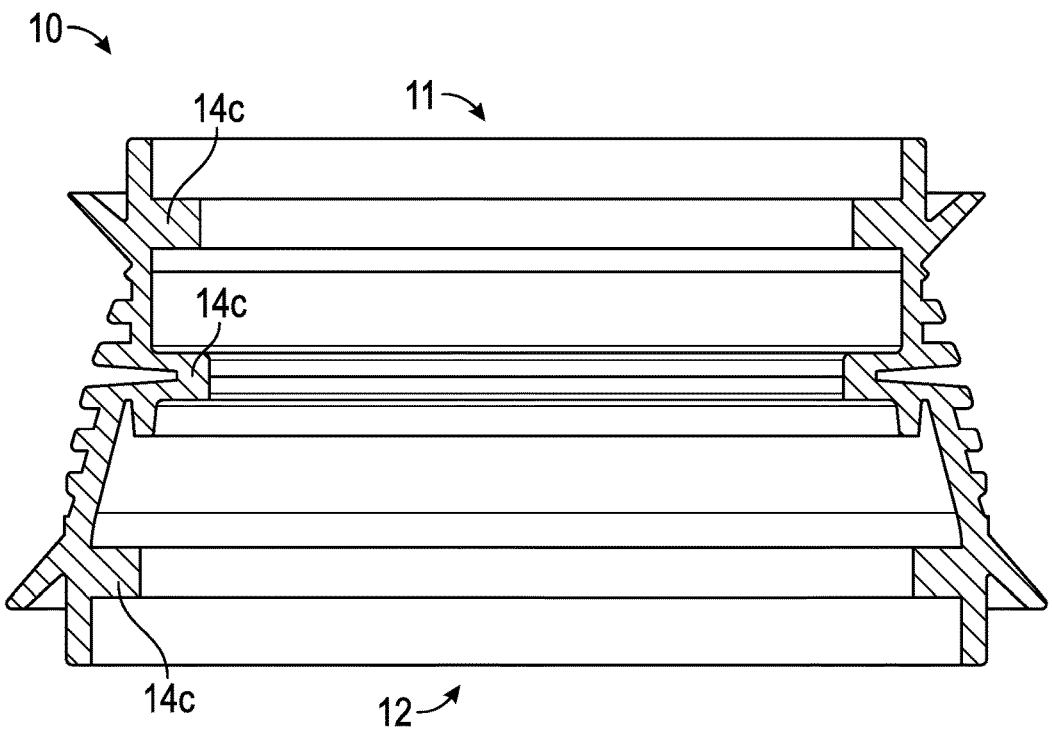
Figure 4F:
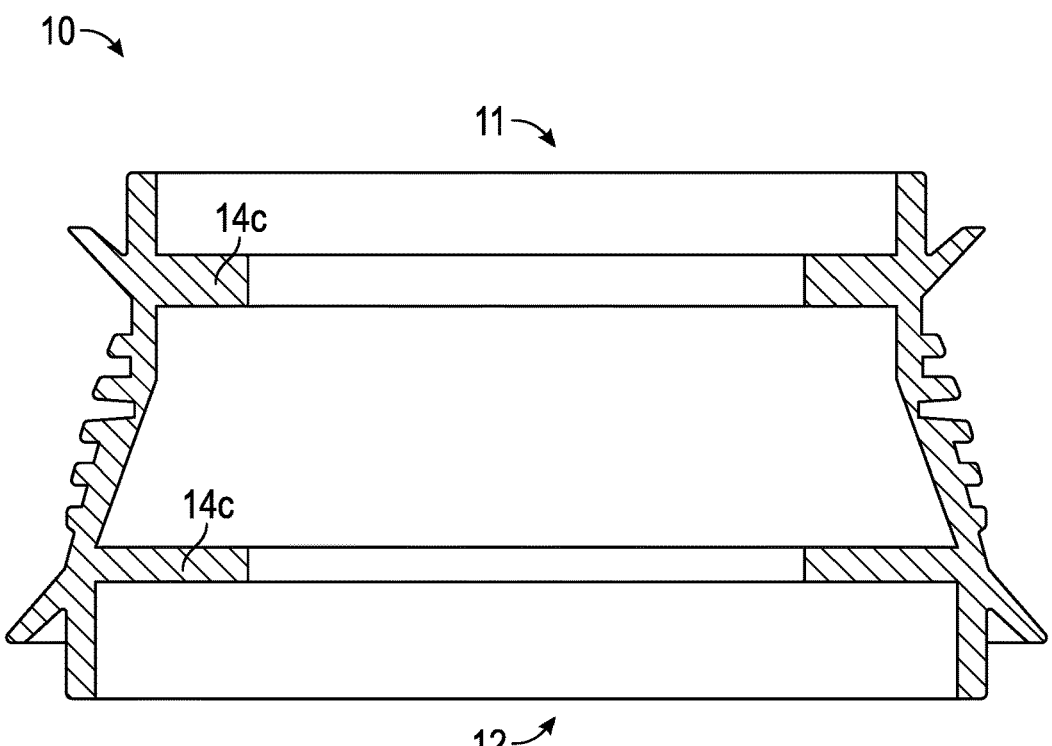

In some embodiments, the collar's wall 14 may have one or more sets of shelves lining two or more different locations of the wall 14. In other words, the interior of sidewall 14 of collar 10 may contain a series of evenly or unevenly spaced parallel shelves. For example, a shelf 14c may be positioned away from the midpoint and closer to collar end 11, and another shelf 14c may be positioned closer to collar end 12, as shown in FIG. 4F. In such an embodiment, when the stabilizer end 26 abuts the shelf 14c, the distance between the stabilizer base portion 21 and the receiving end of the collar is greater than if the shelf 14c were placed at the midpoint of the inner wall 14. This embodiment creates a longer inner cavity 19 to accommodate longer cervixes, which slide through the length of the collar (e.g., FIG. 13B). The shelf sets may have identical designs, or may have different designs according to the possibilities described below.

In another embodiment, the collar's wall 14 may have more than two sets of shelves to accommodate stabilizers of different depths and diameters. For example, a collar may contain one or more shelves 14c located on either side of the inner wall 14's midpoint, as shown in FIG. 4E. Thus, a stabilizer with a larger diameter may abut a shelf located closer to end 11 or end 12 of the collar, whereas a stabilizer of smaller diameter may be designed to slide past the first shelf and press against a second shelf closer to or at the midpoint of collar wall 14. Multiple shelves of different diameters would accommodate cervixes of different lengths. The shelf sets may have identical designs, or may have different designs according to the possible embodiments described below.

In an embodiment, a shelf 14c may be comprised of one or more continuous circular rings, protrusions, or ledges which the prongs 22, rim 25, or end 26 of the stabilizer snaps, slides, locks into or simply presses against. In another embodiment, the shelf 14c may be one or more discontinuous shelf tabs, protrusions, abutments, which the prongs 22, rim 25 (which may or may not be continuous in different embodiments), or end 26 of the stabilizer snaps, slides, locks into or simply presses against. The discontinuous shelf tabs may be evenly or unevenly spaced, polygonal, curved, or mixed. The discontinuous shelf tabs have the same or different shapes and be smooth, jagged or mixed. In another embodiment, the shelf 14c may be comprised of a subset of both continuous and discontinuous shelves. Mixed shelves would facilitate a locking mechanism of stabilizer rim 25 to collar 10. In other embodiments, when a collar contains multiple sets of shelves, one set may be continuous while the other set is discontinuous. One set may also include both continuous and discontinuous sub-shelves to facilitate a locking function.

In other embodiments, a shelf 14c may be angled against the sidewall 14, be rounded, have a trapezoidal or polygonal surface, or the like to further facilitate security and stability of the stabilizer end or rim 25. In addition, a shelf 14c may have an angled or perpendicular shelf 14d to reduce slide or slippage of the stabilizer rim and hold it in place. The angled shelf 14d may be continuous or discontinuous as a series of shelf tabs, with possible configurations described in the preceding paragraph. An angled shelf or shelf tabs is/are particularly useful on the side of the shelf facing end 12, which may have a greater surface area because of the increasing diameter of the sidewall 14 from end 11 to end 12. Alternatively, the inner sidewalls may have varying thickness to achieve the same effect as shelves or to support a shelf or multiple shelves.

The surface area of the shelf 14c may be increased to the point where it creates a continuous disc or surface without holes. In such an embodiment, the disc creates a closed end of the collar so that the stabilizer end 25 presses against the closed end. This embodiment reduces the dual-use collar into a single use collar and limits intravaginal access to the cervix.

In some embodiments, the distance 17h between the shelf 14c and end 11 may be between 2-5 mm, 5-10 mm, 10-15 mm, 15-20 mm, 20-25 mm, or 25-30 mm. In some embodiments, the distance 17i between the shelf 14c and end 12 may be between 2-5 mm, 5-10 mm, 10-15 mm, 15-20 mm, 20-25 mm, or 25-30 mm. In some embodiments, the distance 17j between the inner edge of shelf 14c and the closest edge of shelf tab 14d may be between 0-1 mm, 1-2 mm, 2-4 mm, 4-6 mm, or 6-8 mm. In some embodiments, the shelf thickness 17k may be between 0-1 mm, 1-2 mm, 2-4 mm, 4-6 mm, 6-8 mm, or 8-10 mm.

Dual-Use Stabilizer

Figure 6A:
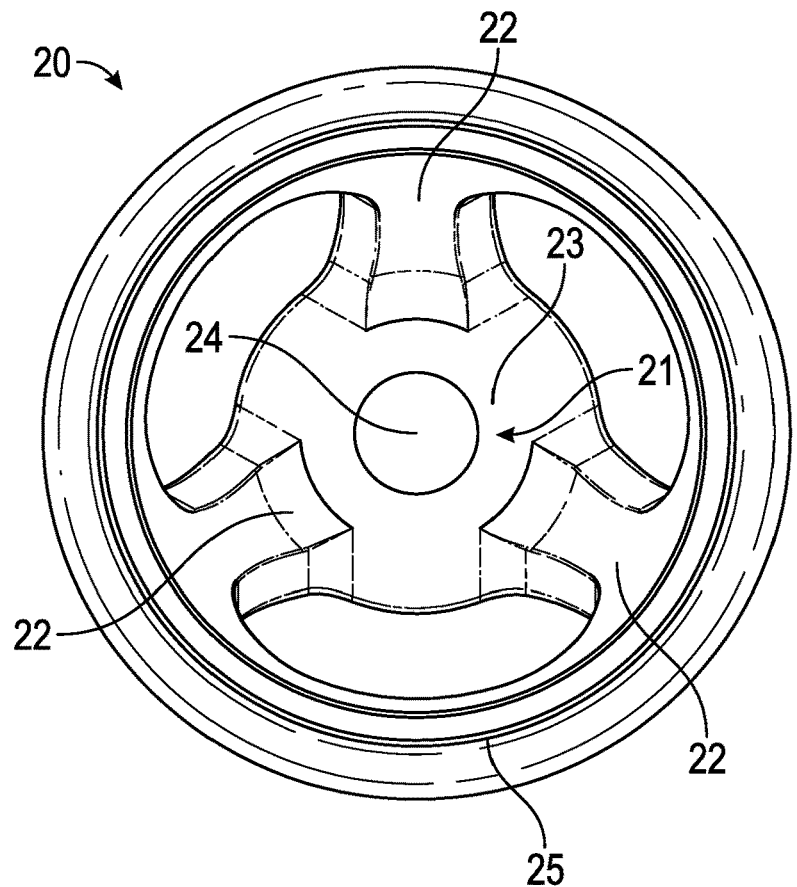
FIGS. 6A-6E illustrate an embodiment of a stabilizer with a delineating rim.

FIGS. 6A-6E illustrate a stabilizer 20 according to an embodiment of the invention. As shown in FIG. 6A, the stabilizer 20 includes a base portion 21, prongs 22 extending from the base portion 21, and a rim 25 unifying the prongs 22 (although other embodiments may forego a continuous rim and include one or more prongs). The base portion 21 includes walls 23 that define an opening 24 at a center portion of the base portion. The opening 24 is of sufficient size to pass a tube or shaft, such as a shaft 31 of a uterine manipulator (as shown in FIG. 2A). The opening may also include an extended guide hole with walls 33 to facilitate passage of the shaft, as shown in FIG. 14C. In another embodiment, the stabilizer has a sidewall 29 without prongs or windows, as shown in FIG. 14A.

As shown in FIG. 6A, the stabilizer 20 contains a rim surface 25 having an outer edge 25a, an inner edge 25b, and a rim surface 25c between the outer and inner edges 25a and 25b. The stabilizer 20 also includes a second outer rim edge 25f separated from surface 25a by a trough or gully 25g.

Figure 14A:
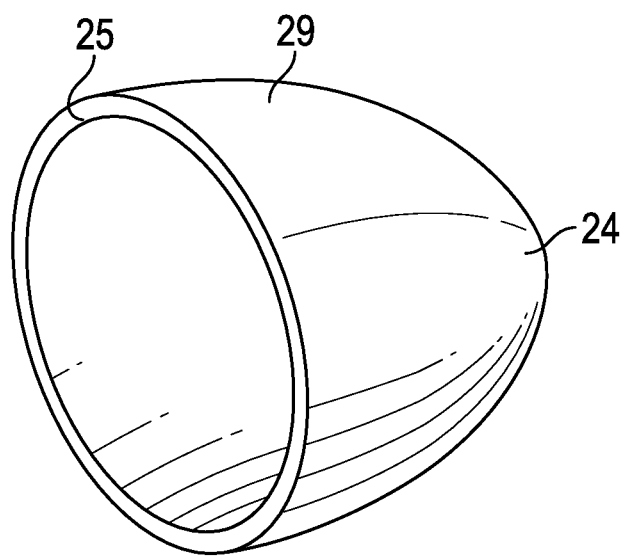
FIGS. 14A-14H illustrate embodiments of a stabilizer.
Figure 14B:
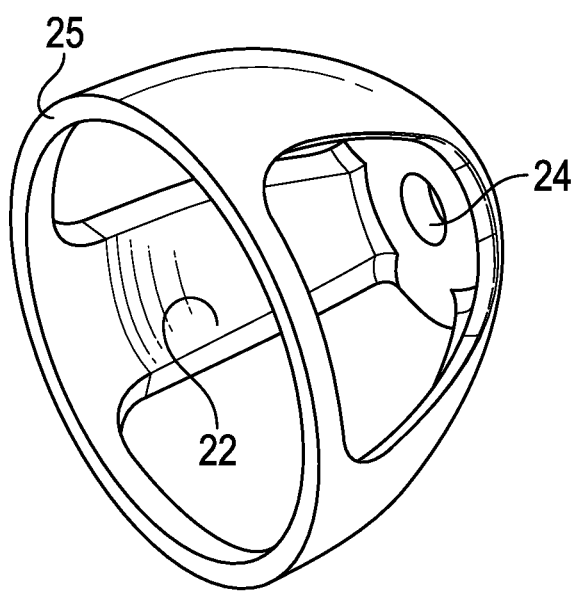
Figure 14C:
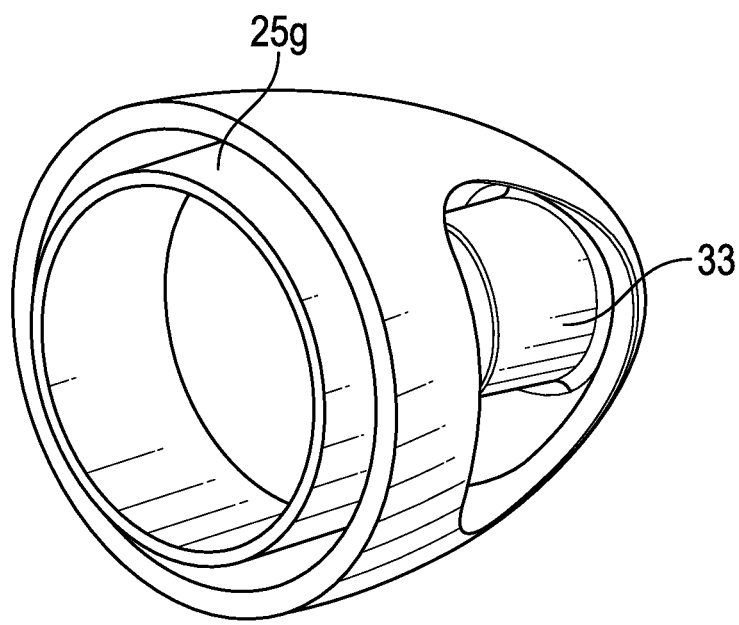
Figure 14D:
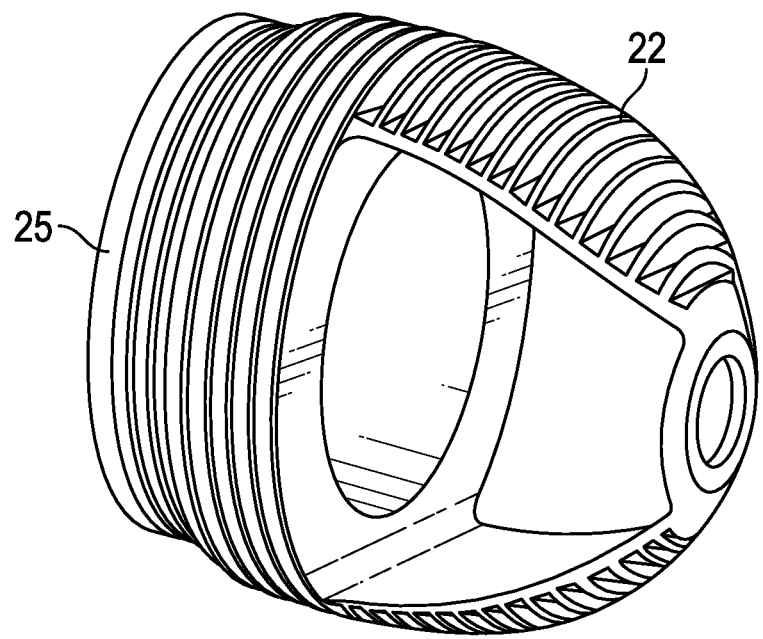

FIGS. 14A through 14F illustrate alternative embodiments of the stabilizer, containing features that may be mixed and matched. FIG. 14A shows a stabilizer with a sidewall 29. This sidewall 29 may have one or more windows or holes 27, as shown in FIGS. 14E-14H. FIG. 14B shows an embodiment that is single-rimmed, whereas FIG. 14C shows a double-rimmed embodiment. FIG. 14D shows an embodiment of a stabilizer with ridged or ribbed sidewalls.

Figure 6B:
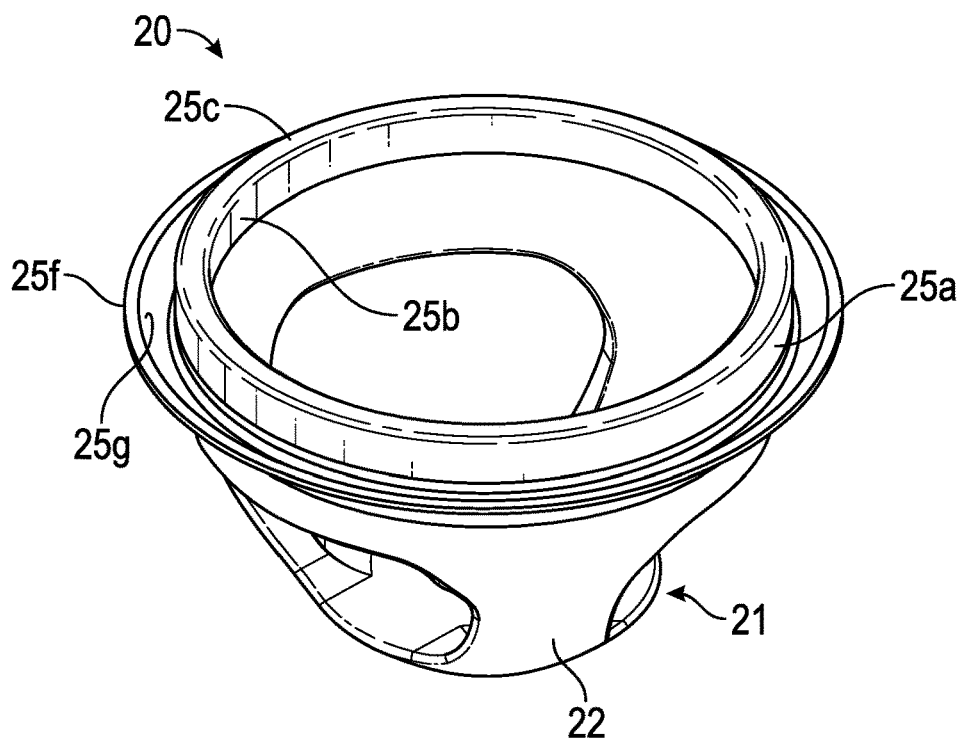
Figure 6C:
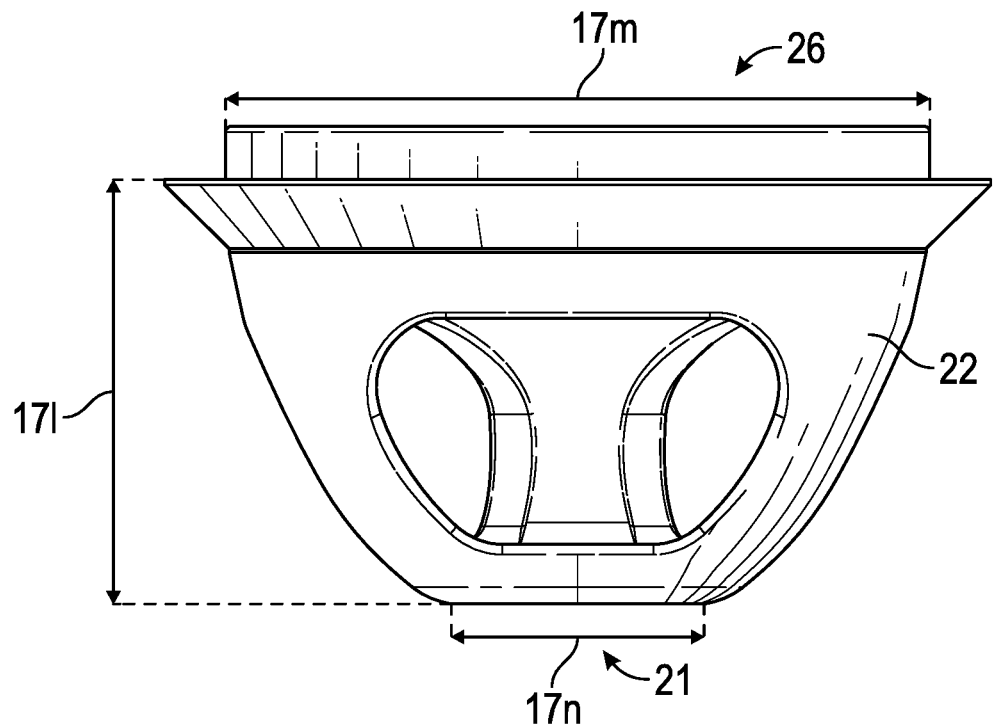
Figure 6D:
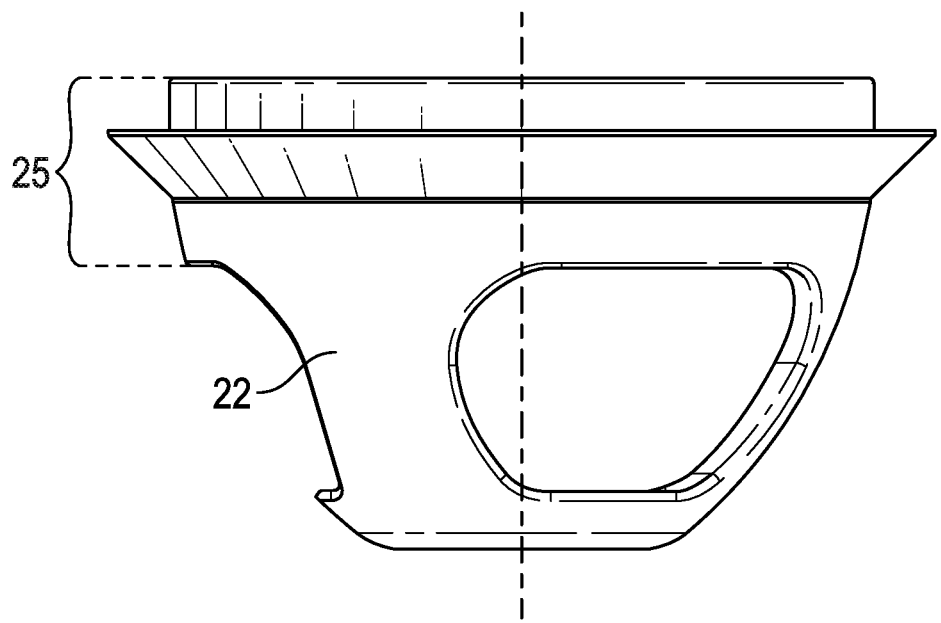
Figure 6E:
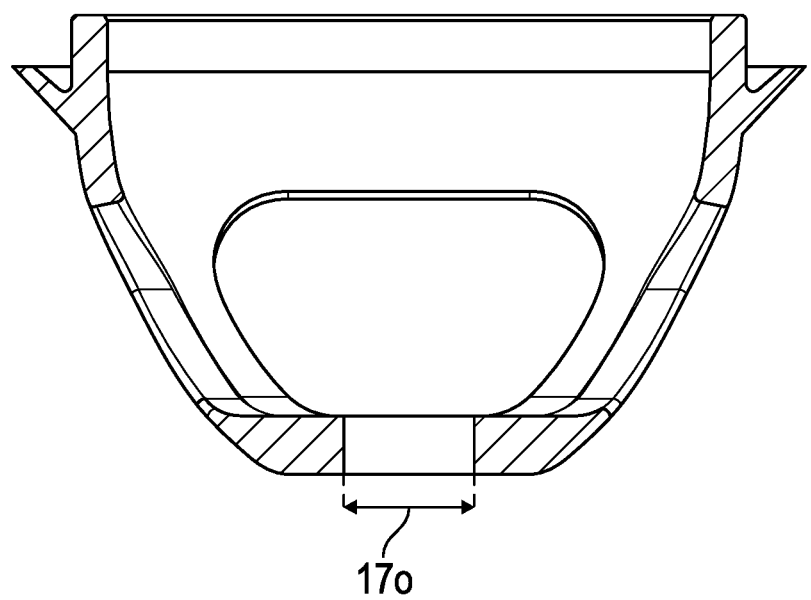
Figure 14E:
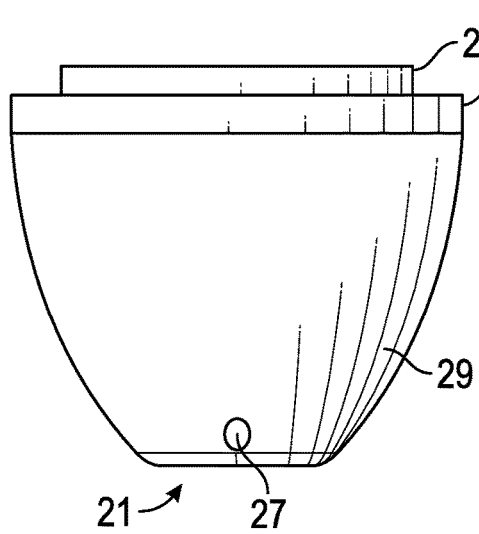
Figure 14F:
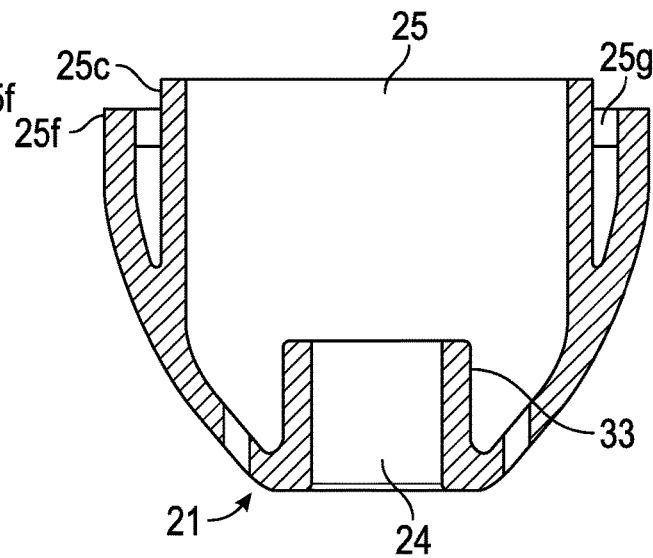
Figure 14G:
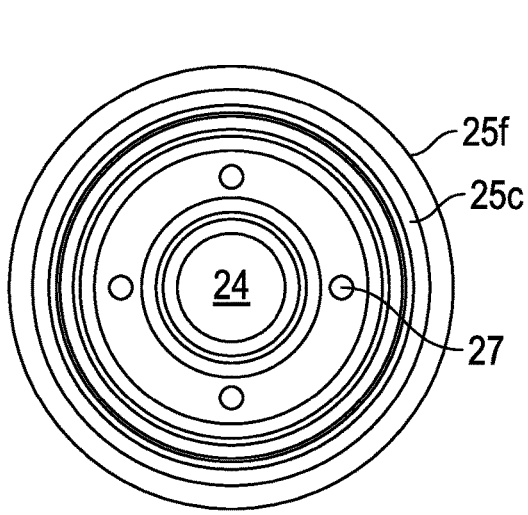
Figure 14H:
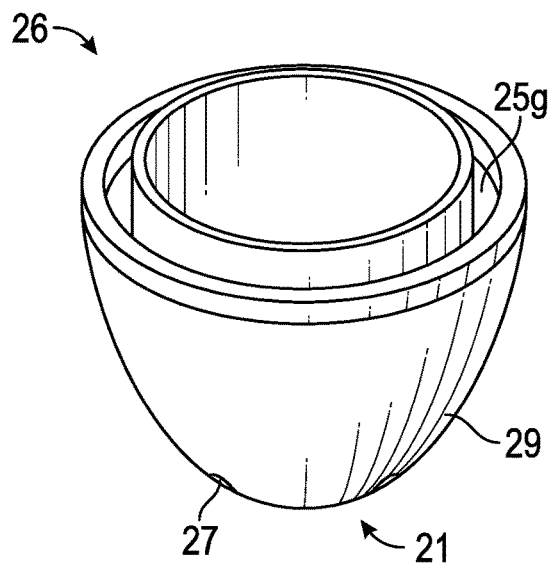

FIGS. 14E through 14F illustrate four views of an embodiment of a stabilizer. FIG. 14E is a side-view, 14F a cross-sectional view, 14G a top-down view, and 14H is an angled view. In this embodiment, the stabilizer 20 includes a base portion 21, sidewall 29 extending from the base portion 21 with windows 27, and a rim 25. The opening 24 is of sufficient size to pass a tube or shaft, such as a shaft 31 of a uterine manipulator. The opening 24 also includes an extended guide hole with walls 33 to facilitate passage of the shaft. The holes 27 may be utilized to suture the cervix with the stabilizer 20 for easy removal of the cervix after a colpotomy or hysterectomy. In other words, a surgeon may pass a needle and thread through the hole to suture the cervix to the stabilizer's sidewall 29. The sidewall 29 may be smooth, or alternatively ridged or ribbed as the stabilizer prongs shown in FIG. 14D The '517 application describes a variety of rim shapes and configurations applicable to rim 13 of end 11, depicted also in many of the figures. These and other shapes and configurations are also applicable to rim 25 of stabilizer 20. The stabilizer may also serve as a delineator for abnormally small cervixes and may contain a gully 25g as shown in FIG. 6B to facilitate an incision. For example, for abnormally small cervixes that are smaller in diameter than end 11 of the collar 10, the surgeon may slide the stabilizer over the cervix without the accompanying collar, and use stabilizer's rim 25 to delineate the fornix, as shown in FIG. 8E. Small cervixes do not require the same support as a normal or large cervix; therefore the stabilizer is sufficient in serving as a fornix manipulator or delineator, further reducing the need for multiple collars and saving costs.

In some embodiments, the stabilizer may have a number of embodiments. In some embodiments, the height 171 between the base portion 21 and unifying rim 25 may be between 5-10 mm, 10-15 mm, 15-20 mm, 20-25 mm, or 25-30 mm. In some embodiments, the diameter 17m of the rim 25 may be between 10-15 mm, 15-20 mm, 20-25 mm, 25-30 mm, 30-35 mm, or 35-40 mm. In some embodiments, the diameter 17n of the base portion 21 may be between 5-10 mm, 10-15 mm, 15-20 mm, or 20-25 mm. In some embodiments, the diameter 17o of the opening 24 may be between 0-2 mm, 2-4 mm, 4-6 mm, 6-8 mm, or 8-10 mm.

Reinforced Stabilizer

Figures 7A, 7B:
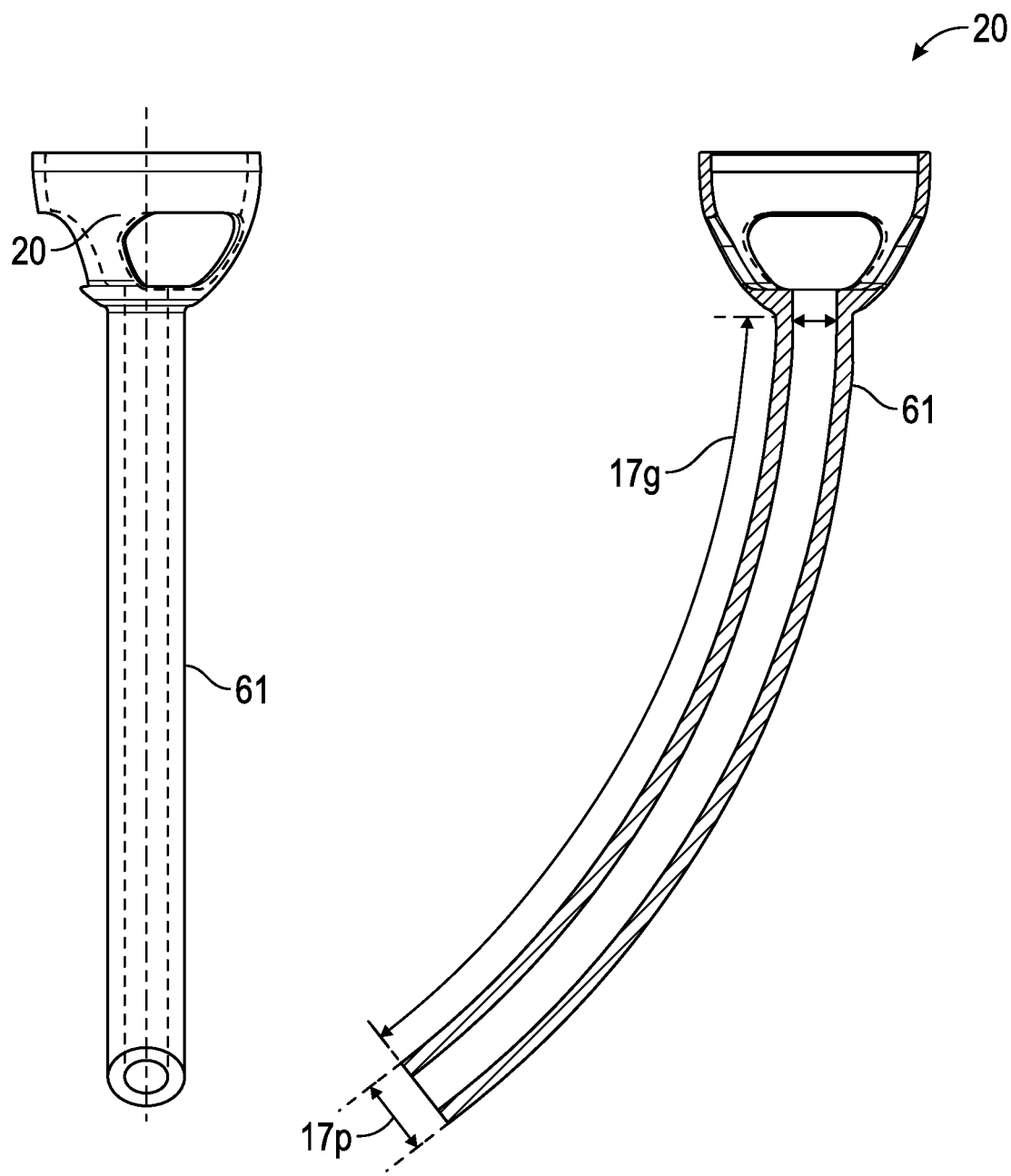
FIGS. 7A-7B illustrate an embodiment of a reinforced stabilizer.
Figure 17:
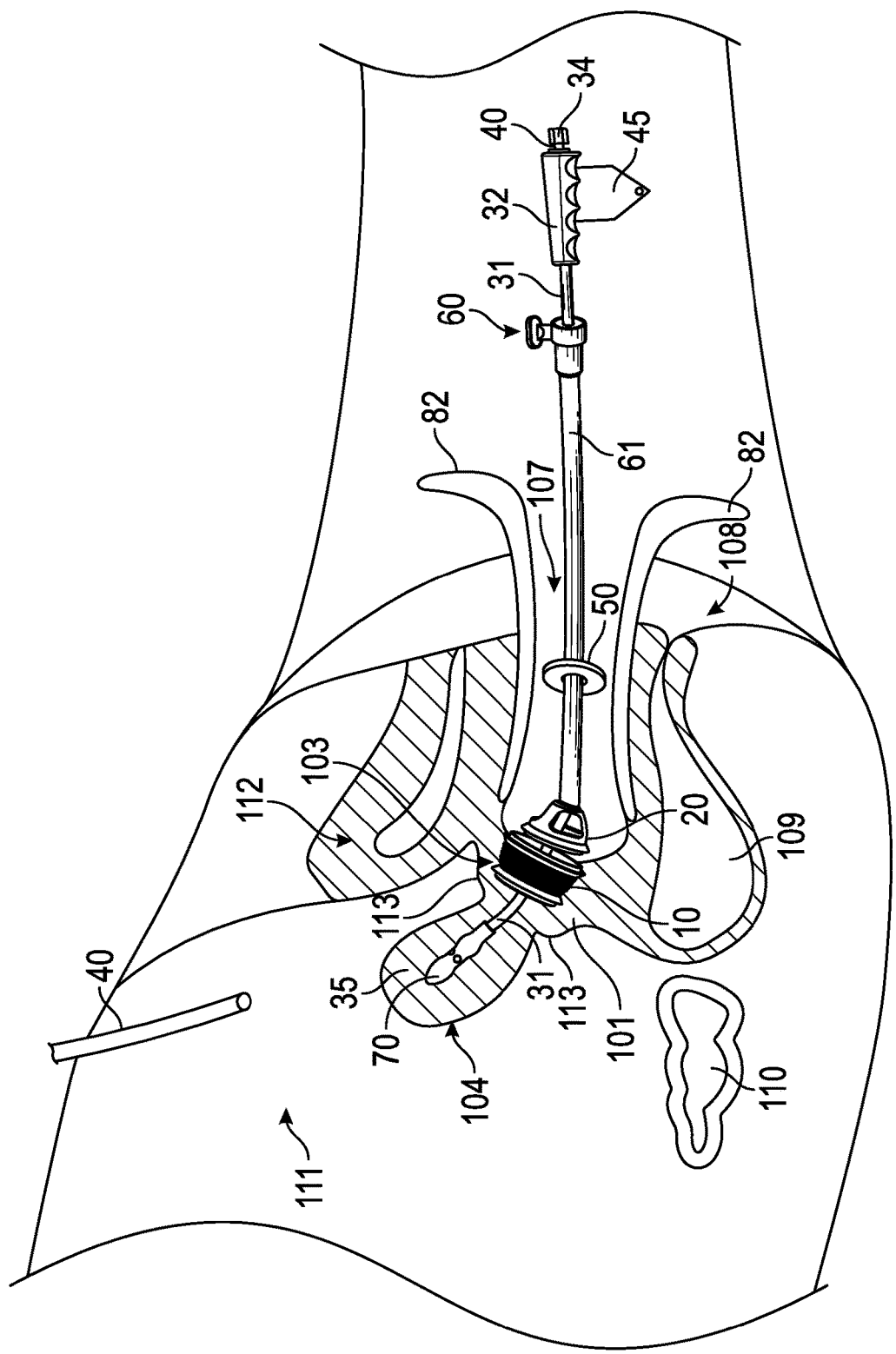
FIG. 17 illustrates an embodiment including a uterine manipulator and fulcrum.

FIGS. 7A-7B shows a stabilizer 20 may be connected to an outer tube 61 made of plastic, metal, nanofibers or some other biocompatible material. The tube 61 slides over a portion of the uterine shaft 31, as shown in FIG. 2A, and therefore minimizes the risk of the stabilizer 20 falling into the vaginal canal upon removal from the vagina. The outer tube 61 also allows for more stable application of force against the stabilizer 20 and reduces slippage of the stabilizer against the collar and uterine shaft when the uterine manipulator system is in use against a cervix. The outer tube 61 may be connected to the stabilizer 20 or manufactured as one part. An outer tube 61 may completely surround the shaft 31, as shown in FIG. 2A, or may partially surround the shaft. The outer tube may partially surround the shaft and remain slidable along the shaft. The outer tube 61 may extend a partial or total length of the shaft, as shown in FIG. 17.

A disc or other object may intermediate the connection between outer 61 tube and stabilizer 20 in order to enable a more even distribution of pressure from the outer tube 61 against the stabilizer 20, and to prevent abdominal air leaks from the stabilizer aperture when an incision is made during a colpotomy.

As illustrated in FIG. 2B, the outer tube 61 may also be part of or in fluid communication with a pressing portion 60 that secures the outer tube 61 onto a desired portion of the uterine shaft 31. The pressing portion 60 may be comprised of a fixing portion 62 connected to a screw 63 (e.g., set screw). When the pressing portion is moved to a desired point on the shaft 31, the screw 63 (which is connected to the fixing portion 62) may be tightened to the shaft 31. This fixes the pressing portion 60 on the shaft 31. In another embodiment, the pressing portion may be comprised of a slidable clip or a spring based-clip that locks into place when released. In yet another embodiment, a fastener may include set screw or any other fastener such as, for example, a stop collar. A stop collar (also called a shaft collar) is a mechanical fastener that goes around a shaft or rod with a screw or clamp or other tightening mechanism to fix the collar in position. Stop collars may take the form of small rings. A user can clamp the collar into place by running a screw through the collar and into the shaft, or by clamping the collar to distribute the pressure more evenly and reduce the risk of damage to the shaft. A stop collar may use a threaded portion that, when tightened, drives a member against the inner shaft to lock the shaft into place. A stop collar is a mechanical stop, which can attach components (e.g., outer tube 61) to a shaft (e.g., shaft 31), and may be used for positioning, limiting, and spacing activities.

When the pressing portion 60 is pressed against the outer tube 61, the fornix may be more precisely delineated. This is because the pressing portion applies pressure to the outer tube 61, which in turn applies pressure to the stabilizer 20 (which may or may not be attached to the outer tube 61). The stabilizer 20 applies pressure against collar 10, which causes the rim of the collar to press against the intra-vaginal fornix and distend the fornix. When the pressing portion 60 is connected to the outer tube 61, there is less slippage between the two components and pressure is more directly applied to the fornix.

In some embodiments, the diameter 17p of the tube 61 may be between 2-4 mm, 4-6 mm, 6-8 mm, or 8-10 mm, 10-12 mm, or 12-14 mm. In some embodiments, the length 17q may be between 5-15 cm, 15-25 cm, 25-35 cm, or 35-45 cm.

Alternatively, the outer tube 61 may extend outside the vagina 107, with or without a pressing portion 60 as shown in FIG. 17. An extended outer tube 61 allows a surgeon to adjust the length of the shaft 31 extended through the vaginal canal and uterus by holding fixed the portion of outer tube 61 outside the vaginal canal and then sliding the shaft 31 forward into the canal or backward outside the canal. Sliding the shaft 31 may be facilitated if the shaft 31 is affixed to a handle 32. When the shaft 31 is affixed to handle 32, a surgeon may adjust the length of the shaft 31 extended through the vaginal canal and uterus by holding fixed the outer tube 61 while pushing forward or pulling back the handle 32. In this embodiment, the outer tube 61 operates as a slider or slidable element. The outer tube may extend a partial length of the shaft, or alternatively may exceed the length of the shaft.

The Uterine Shaft

Figure 8C:
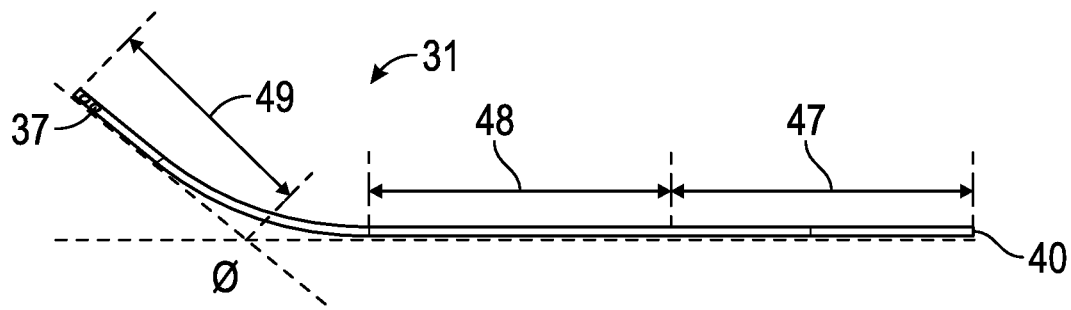

FIGS. 8A-8C show possible embodiments of a uterine shaft 31, a tube made of plastic, metal, or any other biocompatible material, or combination thereof.

For example, the shaft 31 may be a combination of metal or plastic encased by plastic or other nonconductive material. In an embodiment, the shaft 31 contains an inner conduit for passage of fluid. In another embodiment, the tube does not contain an inner conduit.

Figure 8D:
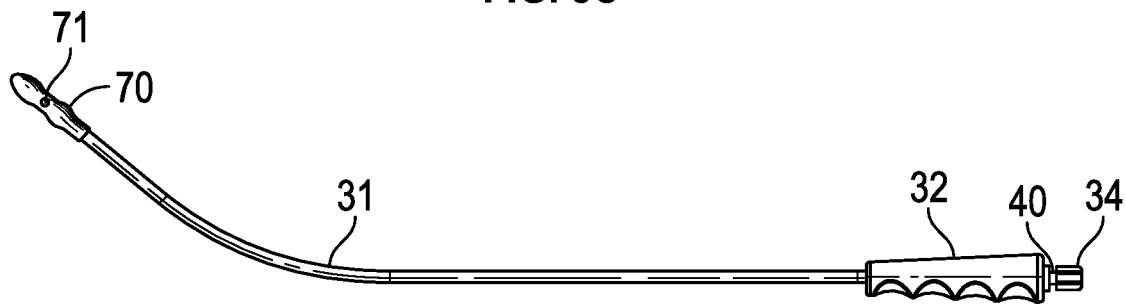
Figure 8E:
Figure 8F:
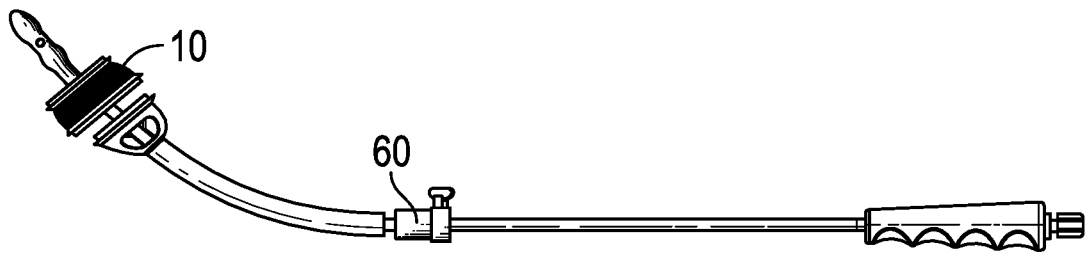

In embodiments where the shaft has an inner conduit, the inlet end of the shaft 31 may contain an inlet 40 configured to receive fluid, as shown in FIGS. 8D-8F. Once injected, fluid may travel to through an outlet 37 at the distal tip of the shaft and into the uterus, or through an outlet 71 on a special tip 70 and into the uterus, as shown in FIGS. 8C & 8D respectively. Inlet 40 may include a cap 34 and lock, luer lock or other mechanism or valve to control fluid flow through shaft 31. As shown in FIGS. 3A-3B and FIG. 12E, the inlet 40 can be attached to either the shaft 31, handle 32, or both. Similarly, the cap 34 may screw on to inlet 40, handle 32, or both.

Figure 8G:
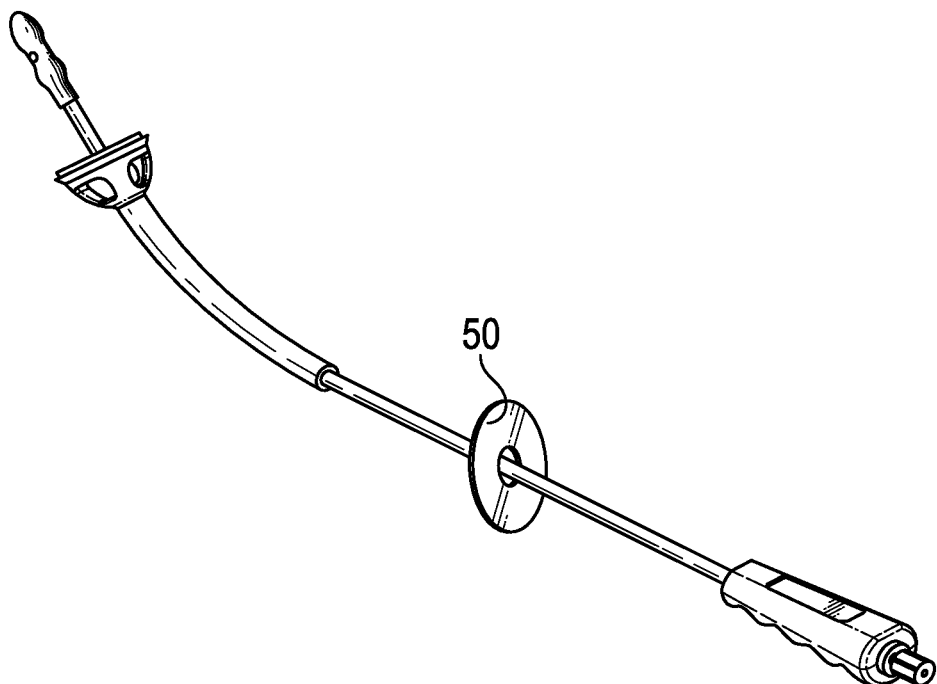
Figure 8H:
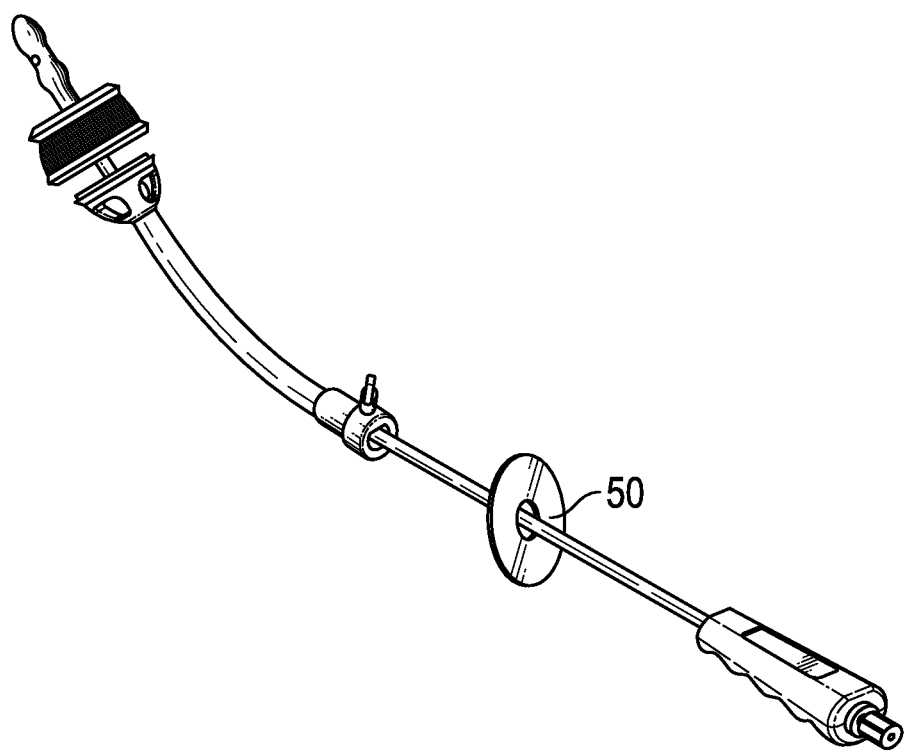

FIGS. 8D-8H show a shaft in combination with various parts, which may or may not be employed depending on the intended use or patient characteristics. For example, FIG. 8D shows a shaft 31 coupled to a tip 70 and handle 32 to create a simple dye delivery system. FIG. 8E shows the addition of a stabilizer 20 and shaft 61 to create an adolescent uterine manipulator system suitable for smaller cervixes. FIG. 8F shows the addition of a collar 10 to create an adult uterine manipulator system for adult cervixes. FIG. 8G and FIG. 8H show the addition of a fulcrum 50 to create a pivot point for the uterine manipulator in the simple and complex uterine manipulator system, respectively.

The outlet end of the shaft 31 may contain a screw portion 36, as shown in FIG. 8A. As shown in FIG. 8A, a screw portion 36 may be comprised of external threads, roots or flanks configured to allow a special tip (such as element 70 shown in FIG. 8D) or balloon to be screwed on for dye delivery, inflation or other medical purposes. Alternatively, the shaft may have one or more openings or holes 37 at its tip or along the shaft's distal sidewalls. The hole 37 may be circular, rectangular, oval, or any other polygonal or trapezoidal shape.

The shaft 31 may have various shapes, as illustrated in FIGS. 8A-8C. FIG. 8A shows a curved shaft 31. FIG. 8B shows a straight shaft 31. FIG. 8C shows a shaft with three sections. The third section 49 is designed for complete or partial insertion into the uterine cavity. The second section 48 is designed to travel partially or completely through vaginal canal. The first section 47 is designed for partial or complete protrusion outside of the vaginal canal. First section 47 may contain a handle 32 and/or inlet 40 with cap 34. As shown in FIG. 8C, the third section 49 may be curved or sharply angled to facilitate manipulation and elevation of the uterus intra-abdominally from nearby vital organs such as the sigmoid colon. Here, the second section 48 includes a second long axis and the distal third section 49 includes a distal end long axis that intersects the second section 48 long axis at an intersection angle between 0 to 90 degrees.

The advantage of the straight shaft with a curved tip, as shown in FIG. 8C, is that movements of the shaft correlate to movements or displacements of the uterus. For example, rotation of the handle leads to direct rotation of the uterus. Movement of the shaft along the horizontal axis leads to horizontal displacement of the uterus. Movement of the shaft along the vertical axis leads to vertical displacement of the uterus. This is not true for multiple curved embodiments of a shaft, such as a shaft shown FIG. 8A. For example, clockwise rotation of an embodiment with a straight shaft with curved tip (e.g., a shaft shown in FIG. 8C) leads to corollary right or clockwise rotation of the uterus. However, in a multi-curved shaft embodiment, exposure of the right fornix requires rotation and a disproportional upward and rightward movement (diagonal movement) of the shaft in order to achieve the same desired orientation. This complex diagonal vector movement is required because of the multiple curvature architecture and lack of a fulcrum in the pelvic cavity. Complex vector movements lead to complex instructions of the surgeon towards the assistant holding the shaft or uterine manipulator system. In contrast, the straight shaft and curved tip as shown in FIG. 8C permits clear instructions of the surgeon to the assistant. Clearer instructions may be facilitated by use of a directional handle described more in detail below.

In an alternative embodiment, the entire shape of the shaft is malleable. In another embodiment, the second and third section is malleable. In another embodiment, the distal third section is malleable. In the latter embodiment, a malleable third section would allow for the distal section to be manipulated 360 degrees along the second section axis and 360 degrees along the axis orthogonal to the second section, or a combination of both. Malleable material includes rubber and other biocompatible materials referenced through this specification or otherwise used in industry.

In some embodiments, the length of the third section 49, or uterine portion, is 4 cm to 15 cm, and may be adjustable. In another embodiment, the length of the uterine portion is approximately 6 cm to 10 cm. The second section 48 designed for the vaginal canal may be 4 cm to 18 cm, depending on the patient's age. Alternatively, it may be a narrow range between 6 cm to 14 cm. The third section 27 containing the handle may be 6 cm or more. In an embodiment, the total length of the uterine shaft from the proximal to the distal end is greater than 15 cm. In an embodiment for adults, this length may be between 25 cm and 40 cm, or more or less. Alternatively, the uterine shaft may be malleable in shape and the outer tube may be employed to adjust the length, as described below. In addition, an acute angle φ between the second section 48 and third section 49 facilitates uterine manipulation and elevation, as shown in FIG. 8C. In an embodiment, this angle is curved and gradual, as shown in FIG. 8C, though it may also be sharp. In an embodiment, this angle may be 20 degrees to 80 degrees, as shown in FIGS. 8C-8F. The angle may be adjustable to achieve greater or lesser angle.

The Tip of the Uterine Shaft

The distal end of the shaft 31 intended for insertion into a uterus may include one or more holes 37 along the sidewall to facilitate release of dye delivered through the shaft's inner lumen, as shown in FIG. 8A. In addition, a hole may be placed at the most distal portion of the shaft's end for release of dye at the most distal portion, as shown in FIG. 8B. Alternatively, a tip 70 may be affixed to the distal end to reduce the risk of perforation of the uterine wall, as shown in FIG. 8D-8F. In an embodiment, tip 70 may be considered a portion of the distal end of the shaft 31.

Figure 9A:
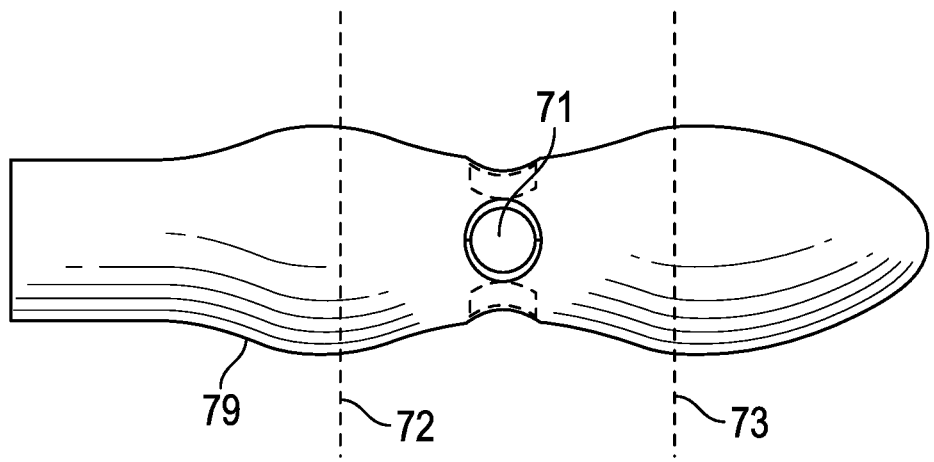
FIGS. 9A-9B illustrate an embodiment of a tip in addition to a cross-section.
Figure 9B:
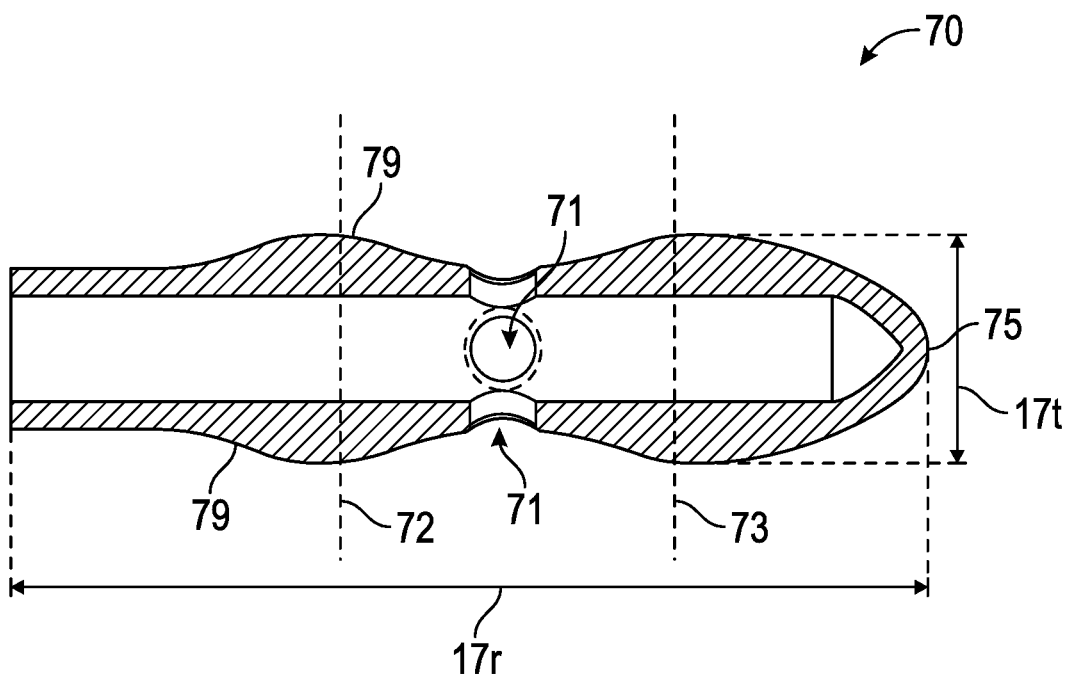

FIG. 9A shows an embodiment of a tip 70, and FIG. 9B show a cross-sectional view. The outlet end of the uterine shaft 31 may be affixed to or screwed into a tip 70 made of plastic, rubber, polyurethane, balloon-like biocompatible material, or other biocompatible or combination material. The tip may be affixed by glue, welding or other mechanism. In addition, the tip and/or the shaft may contain outer ridges, threads, flanks or roots to facilitate a screw mechanism for assembly. The tip 70 is inserted through the cervical canal and into the uterus, as illustrated in FIG. 17.

As shown in FIGS. 9A-9B, the tip 70 may include one or more holes or apertures 71 dispersed along the sidewalls 79. The holes may be circular, oval, rectangular shape, or any other shape, including trapezoidal shape, polygonal or an irregular circle shape. The holes may be microscopic or visible to the human eye. The purpose of the holes is to deliver dye (e.g., blue dye or indigo-carmine dye) into the uterus for, as an example, a "fallopian tube patency" test—an examination carried out to determine whether the fallopian tubes are clear and whether there are any abnormalities in the uterine cavity. To perform the procedure, a surgeon opens the inlet 40 located on the inlet end of the uterine shaft 31 (as shown in FIG. 8B) or on the distal portion of handle 32 (as shown in FIG. 8D), and connects a syringe containing dye to the inlet. The dye is then injected into the uterine shaft 31 and travels along the inner lumen of the shaft 31 into the tip 70 (see FIG. 17 showing anatomy references). The dye then escapes the tip 70 through the hole 71 (or holes) located on the sidewalls 79 into the uterus 104 for the test. If the fallopian tube contains an abnormality, the dye leaks out of the uterus and fallopian tube and is visible in the pelvic cavity 111.

The hole or series of holes 71 may also be placed at the far end 75 of the tip 70, rather than on the sidewalls 79 in an embodiment. However, if the tip 70 is pressed against the uterine wall, the dye does not fill the uterus or enter the fallopian tube but rather remains in the tip or is alternatively absorbed by the uterus tissue or muscle. This may generate a false negative test result, which the current state of the art balloon tip often generates. Hence, in an embodiment, holes are along the sidewalls of the tip 70 to minimize the risk of false negatives by increasing the likelihood that the dye enters the uterus. Alternatively, if a special tip is not employed, one or more holes 37 may exist along the sidewalls of the shaft 31, as shown in FIG. 8A.

Figure 10A:
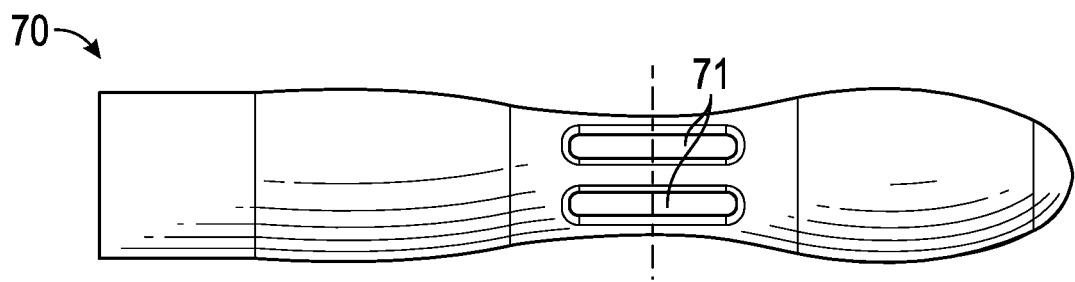
FIGS. 10A-10E illustrate embodiments of a tip.
Figure 10B:
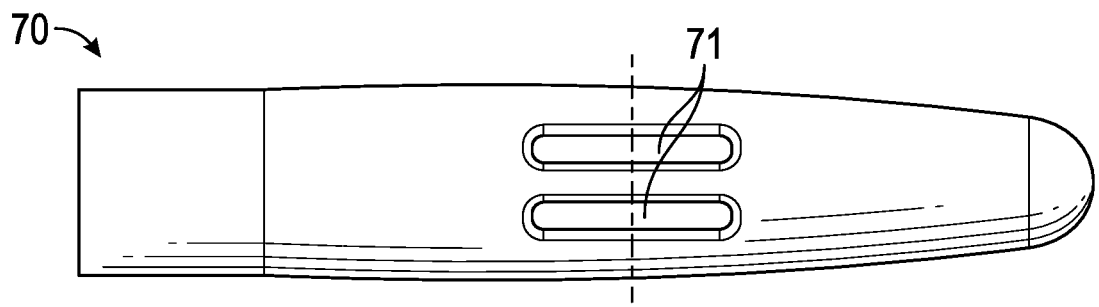
Figure 10C:
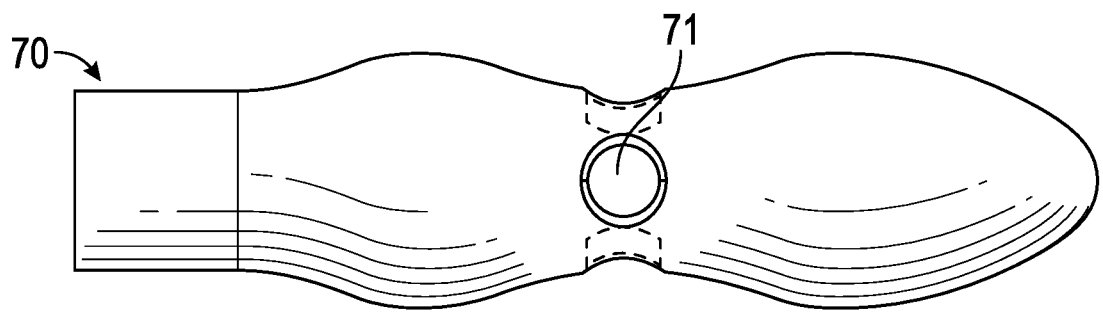
Figure 10D:
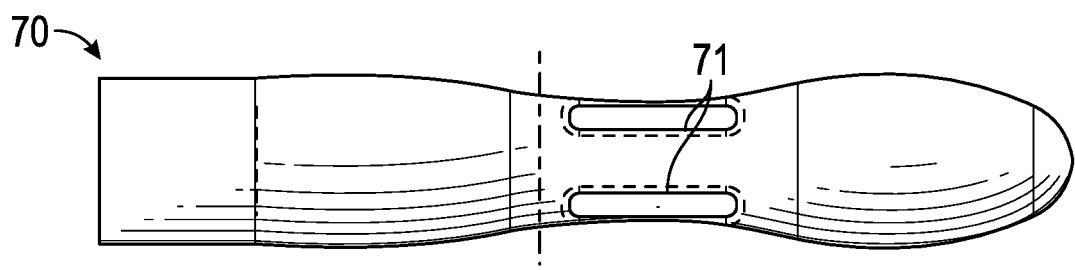
Figure 10E:
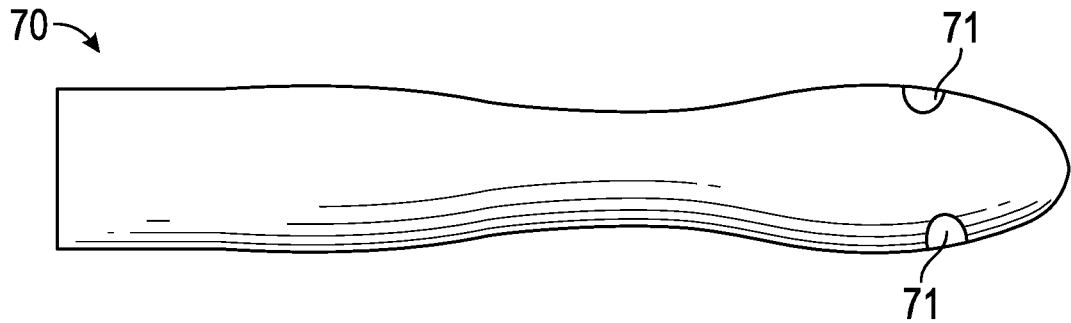

As shown in FIGS. 10A-10E, the tip 70 may have an hourglass, dumbbell, humped, or curved shape. Alternatively it may have less curvature, as shown FIG. 10E, or no or very limited curvature (as shown in FIG. 10B). The curves or humps located at points 73 and/or 72 (shown in FIGS. 9A & 9B) serve to create a back seal between the tip and cervical canal. This prevents the dye from leaking out. In addition the curvature at point 72 prevents the tip from slipping out of the uterus, through the cervix into the vaginal canal. The curve at point 73 provides a rounded, blunted and expanded surface to minimize the risk of perforation of the uterine wall, which may occur if the uterine manipulator is inserted too deeply into the uterus. However, the curvature or number of humps may vary. A tip may have one hump, as shown in FIG. 10B, though it makes the device less efficacious as it is liable to easily slip out. Or the tip may have two or more multiple humps (e.g., 2, 3, 4, 5 and so on). Alternatively, the tip may have different shapes (as shown in FIGS. 10A-10E) at any point including its distal end, such as an oval shape, rectangular shape, oblong shape, arrow shape, and the like. In other embodiments, the tip may have a single rounded snake head, as shown in FIG. 10E.

Figure 11A:
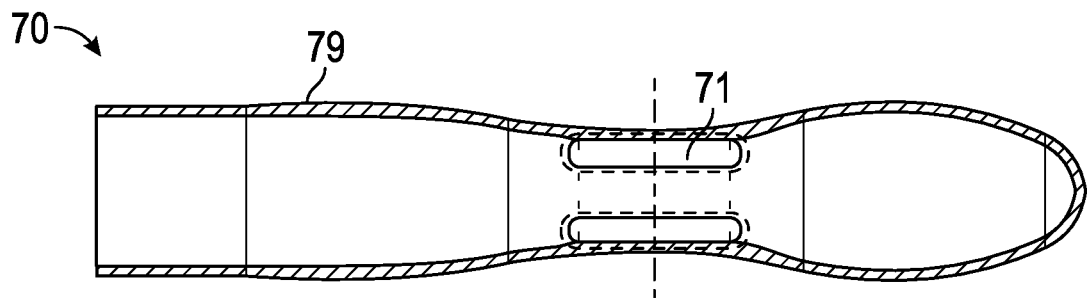
FIGS. 11A-11B illustrate an embodiment of a tip and a cross-sectional view.
Figure 11B:
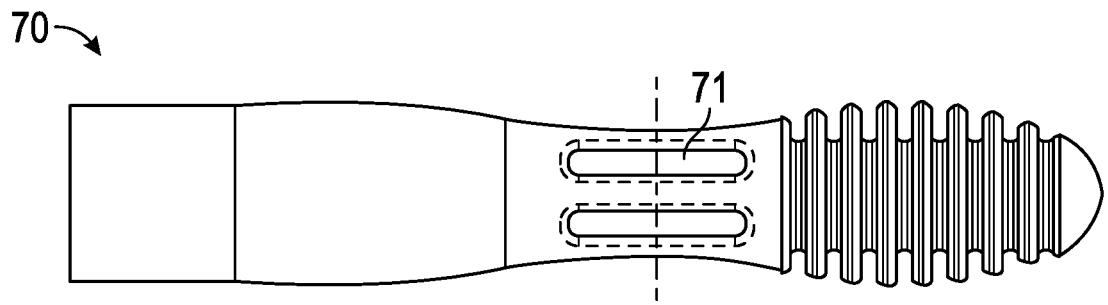

The wall thickness of the tip 70's sidewalls 79 may vary to create an empty oval core 74, as shown in FIG. 9B. Alternatively, the wall may have uniform thickness as shown in FIG. 11A. The tip 70 may also have a ridged exterior to prevent slippage outside of the uterus into the vaginal canal. The ridges may be in on a proximal or distal portion of the tip, as shown in FIG. 11B, or the ridges may be on the entire length of the tip 70. The ridges may be horizontal, vertical, crossed, or in any design. The tip 70 may also include inner ridges at its inner proximal end to facilitate screwing the tip onto the shaft's distal end.

In some embodiments, the length 17r of the tip may be between 10-15 mm, 15-20 mm, 20-25 mm, 25-30 mm, 30-35 mm, 35-40 mm, 40-45 mm, 45-50 mm, 50-55 mm, or 55-60 mm. In some embodiments, the distance between the two humps at point 73 and 72 may be 10 mm to 30 mm. The minimum diameter of the hole(s) 71 may be 0-2 mm, 2-4 mm, 4-6 mm, 6-8 mm, or 8-10 mm. In some embodiments, the diameter 17t at points 73 and 72 may be between 3-5 mm, 6-7 mm, and 8-10 mm. The diameter 17 of the narrow middle portion may be between 0-2 mm, 2-4 mm, 4-6 mm, 6-8 mm, or 8-10 mm.

A uterine manipulator system that is comprised of a shaft 31 and tip 70 may serve as a simple dye delivery system, as shown in FIG. 8D. In addition, a modified uterine manipulator system for small cervixes may exist utilizing the stabilizer 20 without the collar 10, as shown in FIG. 8E. In a modified system, an outer tube 61 and pressing portion 60 may be utilized for additional support and stability.

Uterine Shaft Handle

Figure 12A:
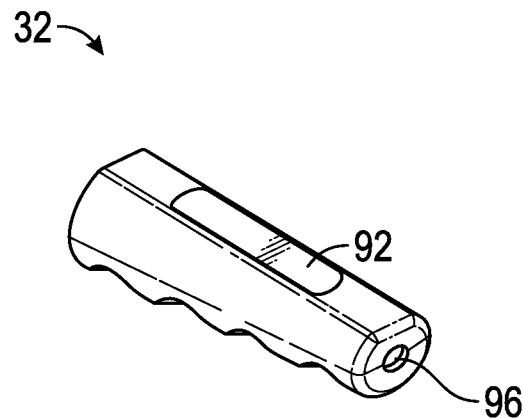
FIGS. 12A-12E illustrate embodiments of a handle.

FIG. 12A shows an embodiment of the handle 32 of the uterine shaft 31 containing a marking, ridge, or compass at 42 to indicate the appropriate angle and direction at which to hold the handle 32. Current uterine manipulators have no indication on the appropriate placement of the manipulator. Physical markers or language at 42, such as "This Side Up" or "Top", would indicate to the holder the appropriate placement of the manipulator and minimize the risk of twisting the manipulator in the wrong direction during surgery. The area with the physical area may be flat or recessed for embossing a label.

As previously discussed, the handle 32 may also have directional components to facilitate precise instructions from the surgeon and corresponding movements of the uterine manipulator from the assistant holding the manipulator. In particular, the handle may have a triangle, polygonal, curved, or mixed shaped base portion 45 with a distinct tip 46 along an axis orthogonal to the axis of the shaft. In other words, the handle may include a base portion 45 that projects orthogonally (or any other angle) to the proximal end of the shaft. This base portion 45 enables a person holding the uterine manipulator to know how many degrees the device is rotated.

This rotation of the shaft 31 is often obscured in current embodiments where a hand wraps entirely around the handle 32, or where rotations of the wrist do not clearly translate to rotations of the device to the human eye. For example, when the base portion 45 is comprised of a triangle with a tip 46, as shown in the embodiment in FIG. 12D, the surgeon may instruct the holder of the device to point the triangle tip 46 to the left or to the right, alternatively at 9 o'clock or 3 o'clock, to achieve the desired configuration. In addition the words "9 o'clock" or "3 o'clock," "left" or "right" or any other such directional language may be printed on either side of the handle. In addition, the tip 46 may also contain a dot or other marking to facilitate simple instructions, such as "dot right" or "dot left" to instruct the holder to rotate the handle appropriately.

Figure 12B:
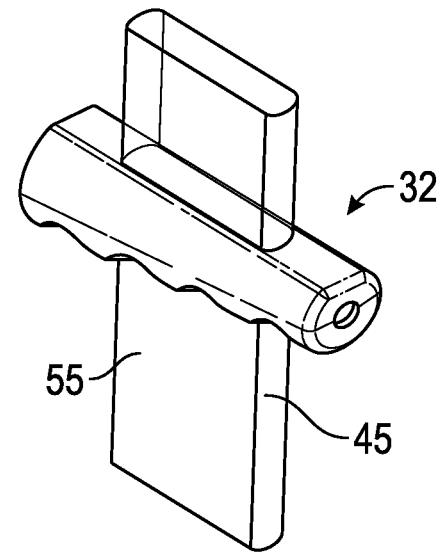
Figure 12C:
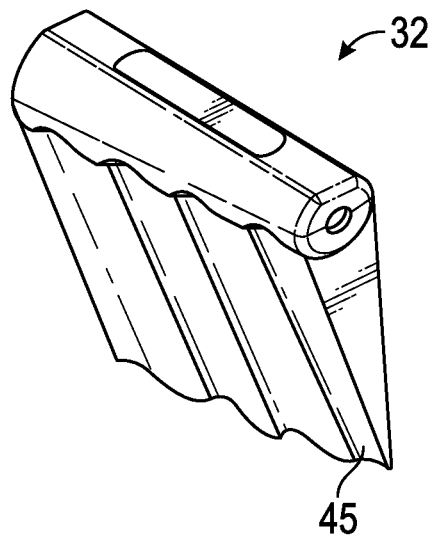
Figure 12D:
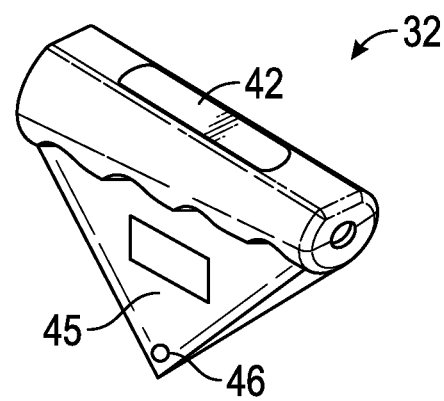
Figure 12E:
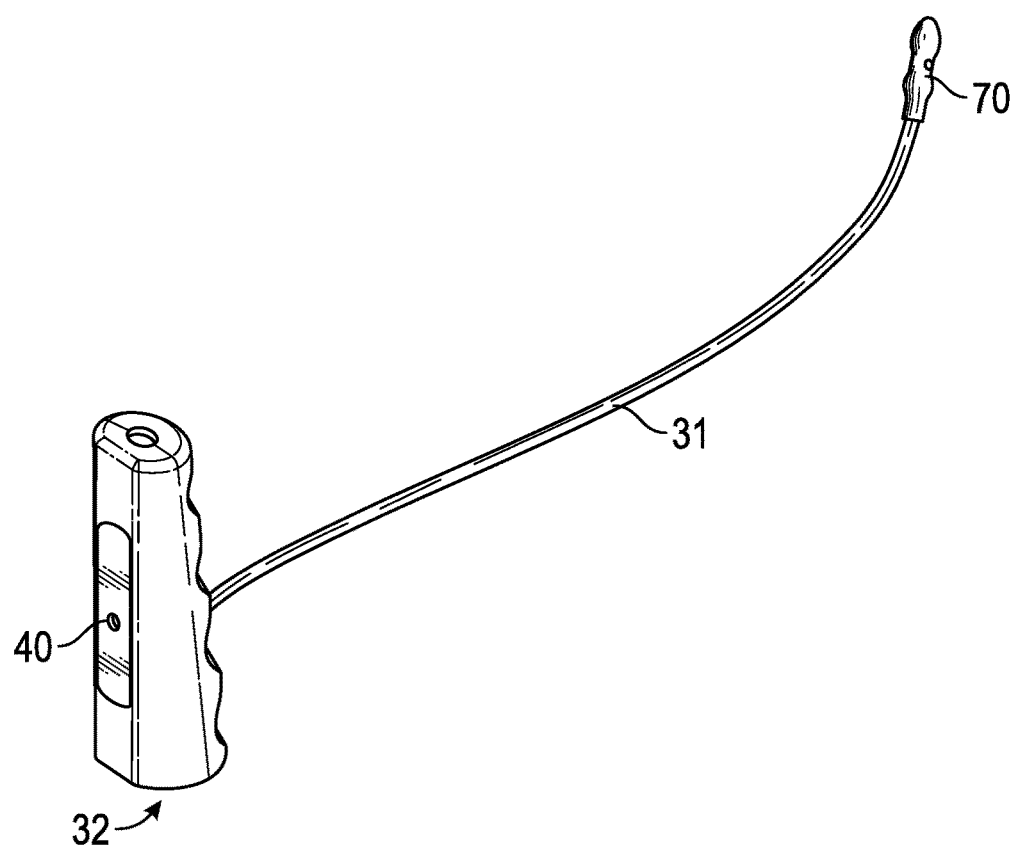

The base portion 45 may also be comprised of a vertical stick, rod or bar 55 attached perpendicularly or at an angle to the handle 32, as shown in FIG. 12B, which allows for similar instruction and printed directional language. The bar 55 may have a triangle or pyramid structure appended to the base portion 45, as shown in FIG. 17. The bar 55 may extend through both ends of the handle 32, forming a T shape, as shown in FIG. 12E. The bar 55 may be rectangular, triangular, or any other polygonal shape. It may be curved or a combination of curves and polygonal shapes. Alternatively, the bar 55 and handle 32 may form a vertical joystick-like grip, wherein fingers are intended to wrap around the face connecting to or proximal to the shaft and the thumb is intended to rest perpendicular to the fingers on the distal portion of the handle 32, as shown in FIG. 12E. When connected to a robotic arm, the grip may be comprised of a robotic arm attachment 220. This attachment may allow allows for forward, vertical, horizontal, and rotational motion or six degrees of freedom of the robotic arm and uterine manipulator system.

Figure 13C:
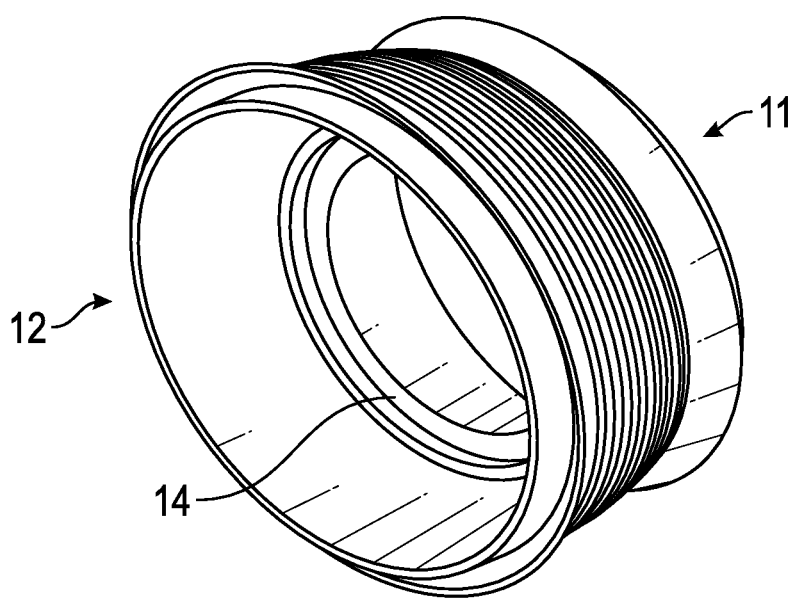
Figure 15A:
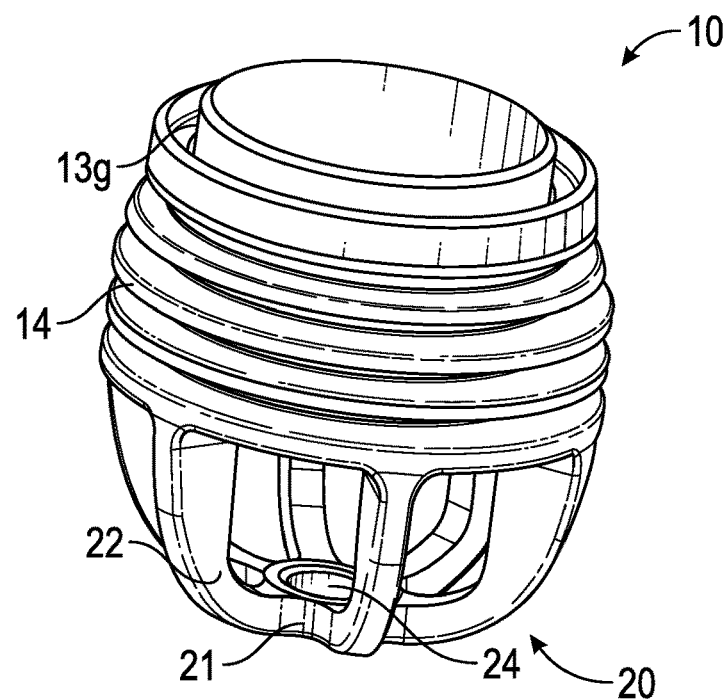
FIGS. 15A-15C illustrate embodiments of a stabilizer coupled to a collar.
Figure 15B:
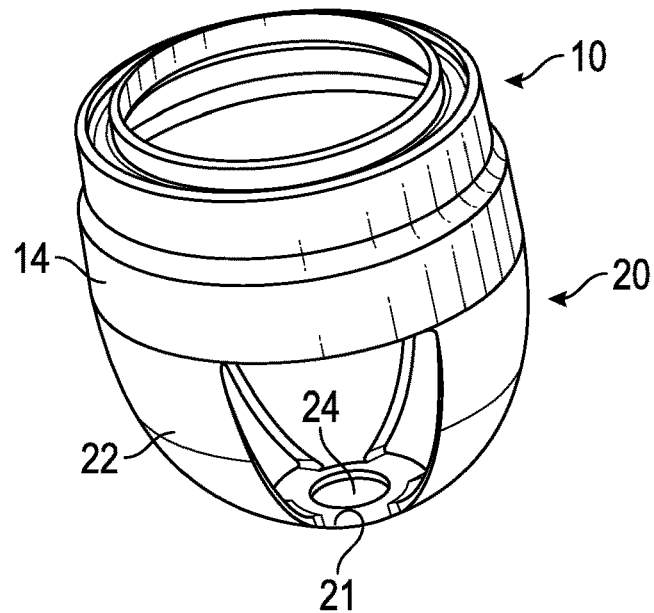
Figure 15C:
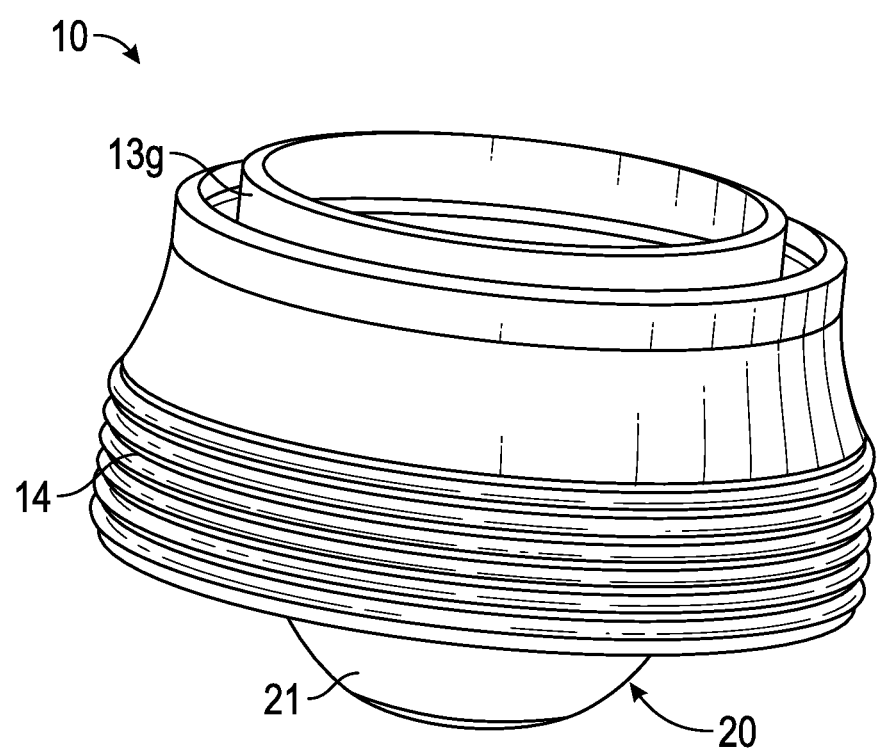

FIGS. 13A-C, 14A-H and 15A-C illustrate alternative embodiments of a stabilizer 20 and collar 10. Each of the embodiments shown in FIGS. 13A-13C generally show opposing ends of a collar whereby one end has a larger diameter than the other end. Like the collar shown in FIG. 2A, the collars 10 shown in FIGS. 13B and 13C include ridges on the outside wall to help guide a cutting surface. FIG. 13B shows an additional hole 14e to facilitate the attachment of a strap 64. FIG. 13B also shows a shelf 14c located at a distal portion, whereas FIG. 13C shows a shelf 14c located at the midpoint of the collar wall 14. FIGS. 14A through 14D show embodiments of a stabilizer configured for attachment to a collar 10. FIG. 14A shows a stabilizer 20 without prongs and instead a sidewall 29. FIG. 14C shows a stabilizer with a double-rim configured for delineating use on a small cervix. FIG. 14D shows a stabilizer with ribbed outer walls configured to reduce slippage within the vaginal canal. FIGS. 14E-14F illustrate an embodiment of a stabilizer with sidewalls 29 and small windows 27. FIGS. 15A-15C show embodiments of a collar and stabilizer manufactured as one piece.

Fulcrum

To facilitate precise displacement of the uterus, the shaft may contain a fulcrum (hereinafter "fulcrum") 50 or an attachment for positioning a fulcrum or fulcrum point, as shown in FIG. 8G-8H. The fulcrum 50 may be placed intravaginally or exist external to vagina. When placed intravaginally, the fulcrum may be comprised of a disc, plate or sponge as shown in FIG. 8G. Alternatively, the fulcrum may be spherical or rounded in shape as shown in FIG. 8H. Alternatively, the fulcrum may be polygonal or trapezoidal in shape. The fulcrum 50 may be positioned or slidable along any portion of the shaft 31. For example, the fulcrum 50 may surround the second section 48 or third section 49 of the shaft 31, as shown in FIG. 8G; it may surround, be a affixed to or part of the outer tube 61, as shown in FIG. 17; or the fulcrum 50 may be positioned between components, such as the outer tube 61 and pressing portion 60, or between the stabilizer 20 and outer tube 61.

Figure 18A:
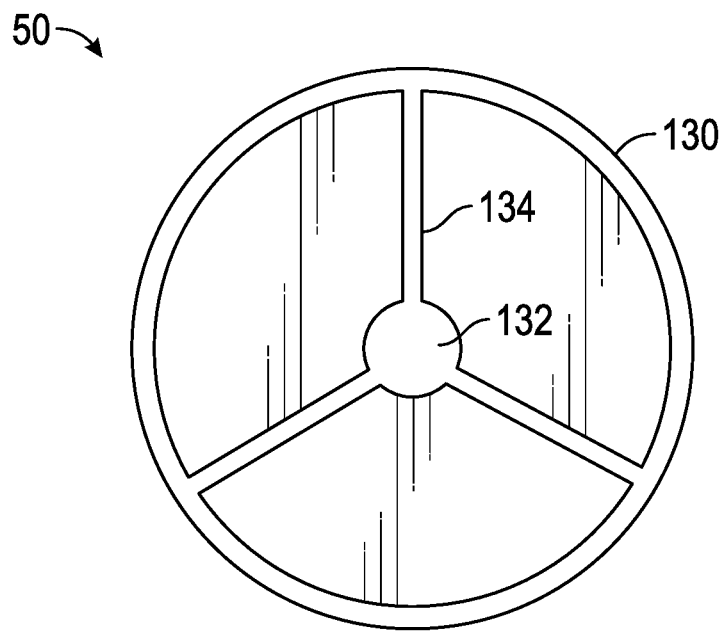
FIGS. 18A-18B include embodiments of a fulcrum.
Figure 18B:
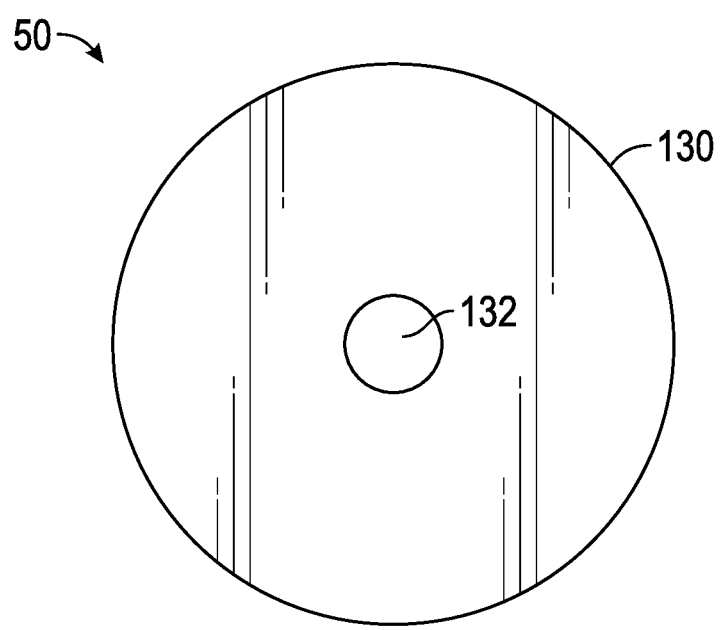

FIG. 18A shows an embodiment of a fulcrum wherein it is a disk structure with one or more arms 134, rim 130 and hole 132. Space exists between arms to facilitate insertion of a tenaculum and provide access to the cervix. Alternatively, as shown in FIG. 18B, the fulcrum may contain no arms and be comprised of a solid disc with one or more holes. When a solid object with a single hole to receive the shaft, the fulcrum has serves as a plug against intrabdominal air leaks after an incision made at the fornix. The rim 130 is adapted to contact the vaginal wall. The fulcrum 50 may also exist, in the alternative, as spherical, oval, trapezoidal, and polygonal shapes. The fulcrum may also be spherical or rounded in shape, or have extended depth into the vaginal canal. Hole 132 may be at the center point of the fulcrum, or another point.

In some embodiments, the fulcrum 50 may be a sponge which slides over the shaft 31 between the stabilizer and shaft handle. A sponge prevents the escape of $CO_2$ from the abdominal area when the fornix is incised. This sponge may be configured to expand into and fill the vaginal cavity. Alternatively, the sponge may be located between the stabilizer 20 and collar 10, and fill any extra space between in cavity 19 of the collar not filled by the cervix. The sponge may be made of gauze or the like. It may be comprised of natural or synthetic sponge material, foam, or any material that naturally expands into the vaginal cavity.

In addition, a plate, tube, speculum or retractor (hereinafter "retractor") 82 may be placed intravaginally to provide resistance against or fixed support for the fulcrum 50. FIG. 17 illustrates an embodiment of a uterine manipulator having a collar 10, stabilizer 20, uterine shaft 31, outer tube 61, pressing portion 60, handle 32, tip 70, and fulcrum 50, used in conjunction with a vaginal retractor 82.

The vaginal retractor 82 is placed within a vaginal canal and used to expand the upper and lower walls of the vagina. A uterine manipulator shaft travels between the retractor and is inserted into the cervix. The retractor plates provide a fixed platform against which the fulcrum 50 operates.

The retractor 82 may be comprised of a spoon like structure with an elongated body and concave distal portion of greater diameter than the elongated body. Alternatively, the retractor 82 may be a speculum, or be comprised of a plate, which may have concave curvature or one or more protrusions perpendicular to the elongated plate, as in a "Sims Retractor." Or the retractor 82 may be comprised of a simple elongated body, which may be concave or convex. The retractor 82 may also be comprised of a hollow tube with two open ends, or a speculum structure with a diameter larger than the uterine manipulator system to permit horizontal and vertical movement of the shaft within the tube. Or the retractor 82 may be any tool or surface that provides a fixed plane. The material may be metal, plastic, or any other biocompatible material.

Figure 16A:
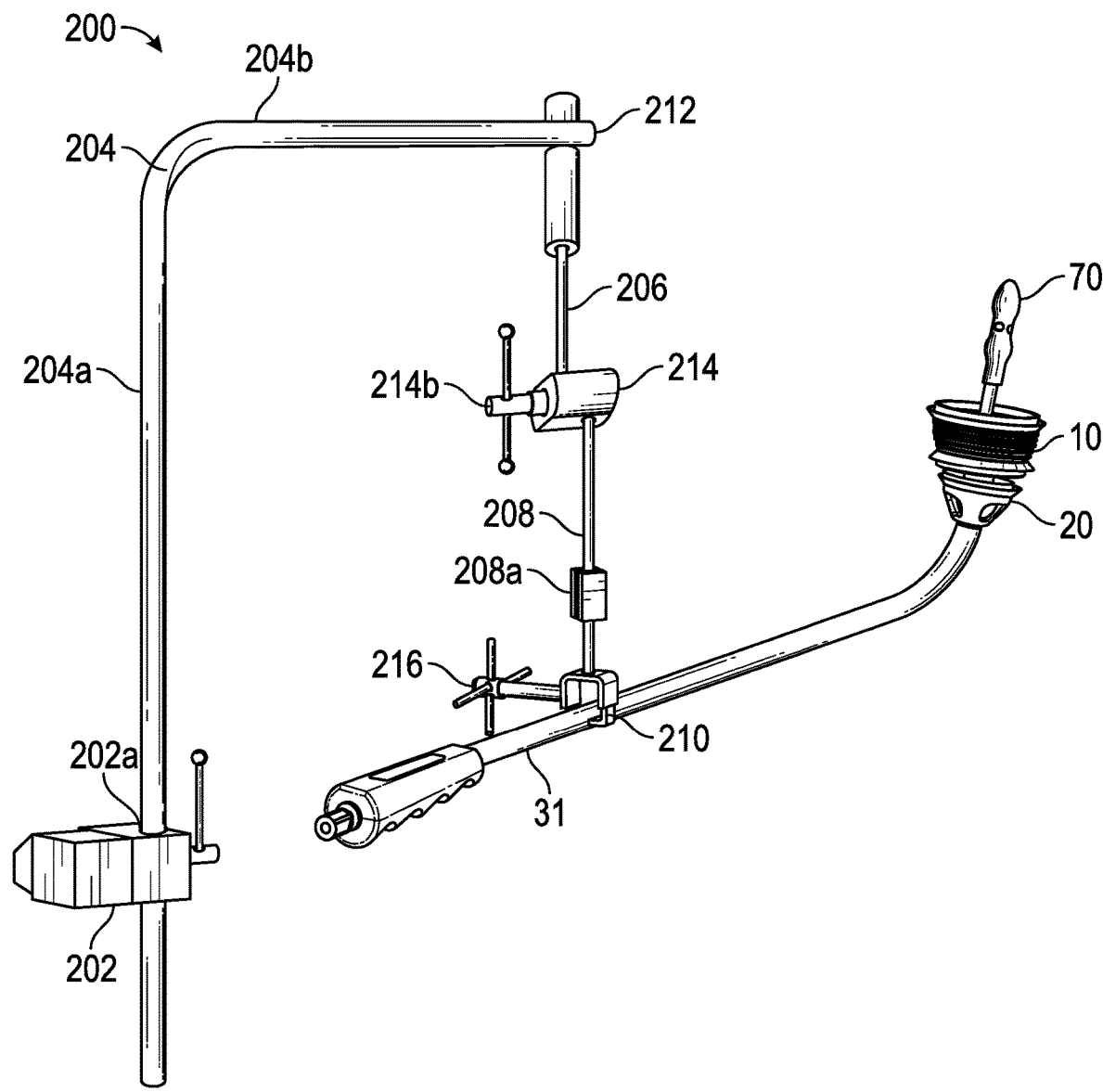
FIGS. 16A-16F illustrate an embodiment of a uterine manipulator system used in conjunction with a fulcrum and linkage to assist in articulation of the uterine manipulator.
Figure 16B:
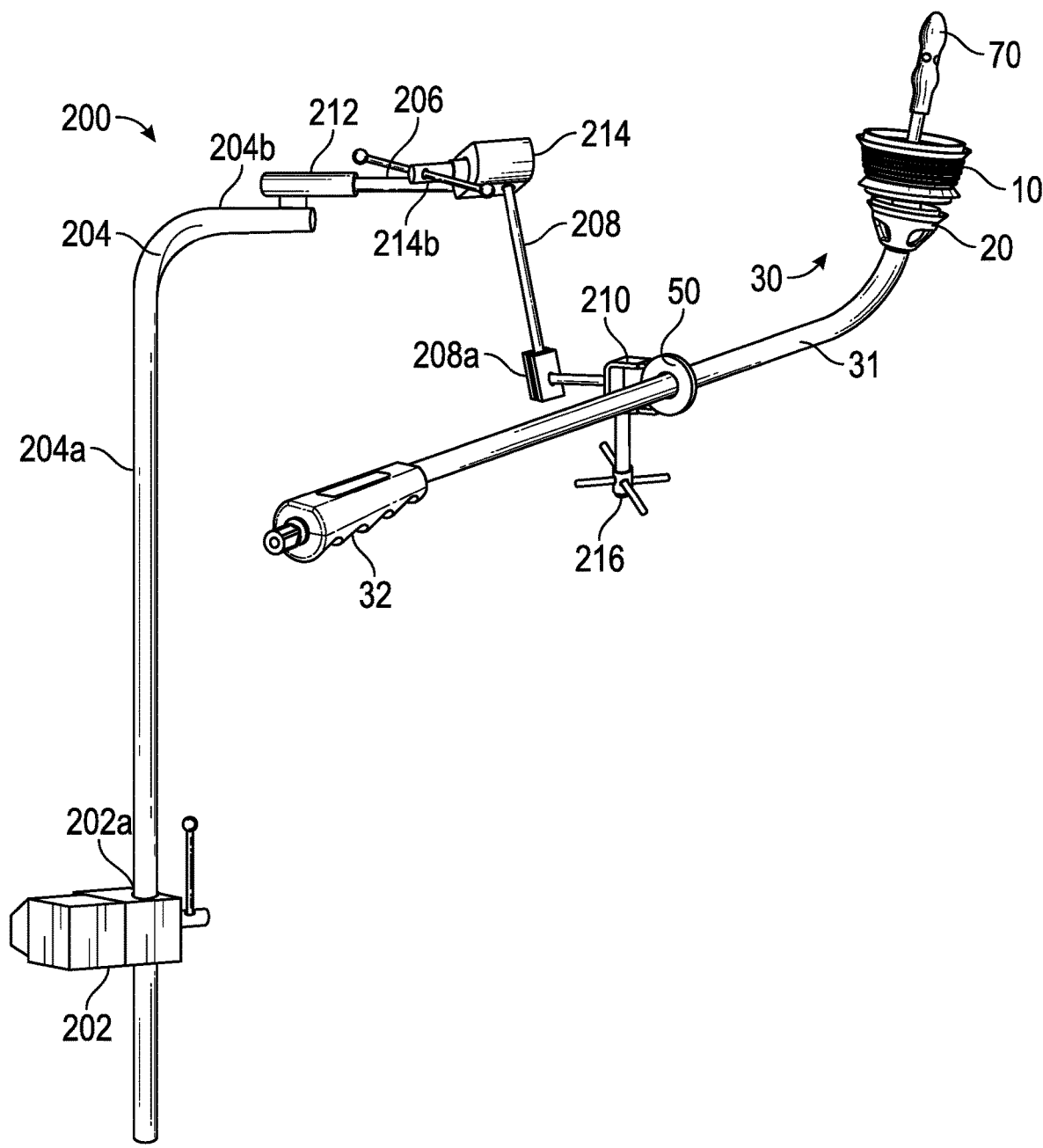

In another embodiment, the fulcrum 50 may be created by coupling an external arm 200 to a shaft 31, handle 32 or outer tube 61 of a uterine manipulator system 30, or dye delivery system, as shown in FIGS. 16A-16F. As shown in FIGS. 16A and 16B, the arm 200 may attach at the second section 48 or first section 47 of shaft 31 to create a fulcrum 50 at the attachment point of the arm 90 to the shaft 31 (e.g., the second section 48 or first section 47 of shaft 31 as shown in FIG. 8C). The arm may also attach to the third section 49, however, this may be invasive in the vaginal canal. When the shaft 31, or other component parts of a uterine manipulator system (e.g., handle 32 or outer tube 61) attaches to an external arm, a fulcrum 50 is created at the attachment point. The fulcrum 50 enables movements of the external arm to correlate to movements of the uterine manipulator system 30 and, when inserted into the uterus, movements of the uterus 104. A fulcrum is particularly well suited for the shaft shapes illustrated in FIG. 8B & FIG. 8C.

Figure 16C:
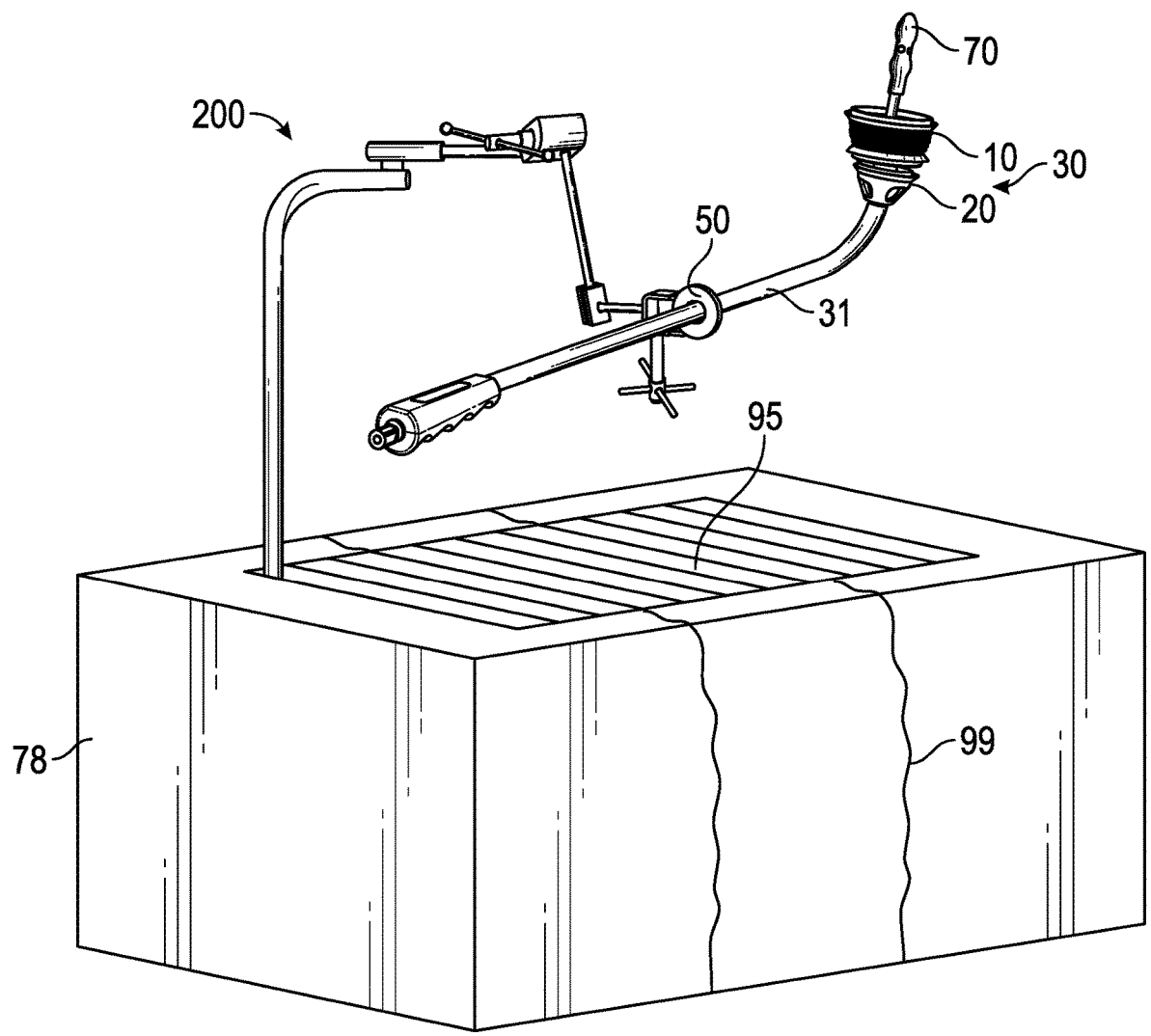
Figure 16D:
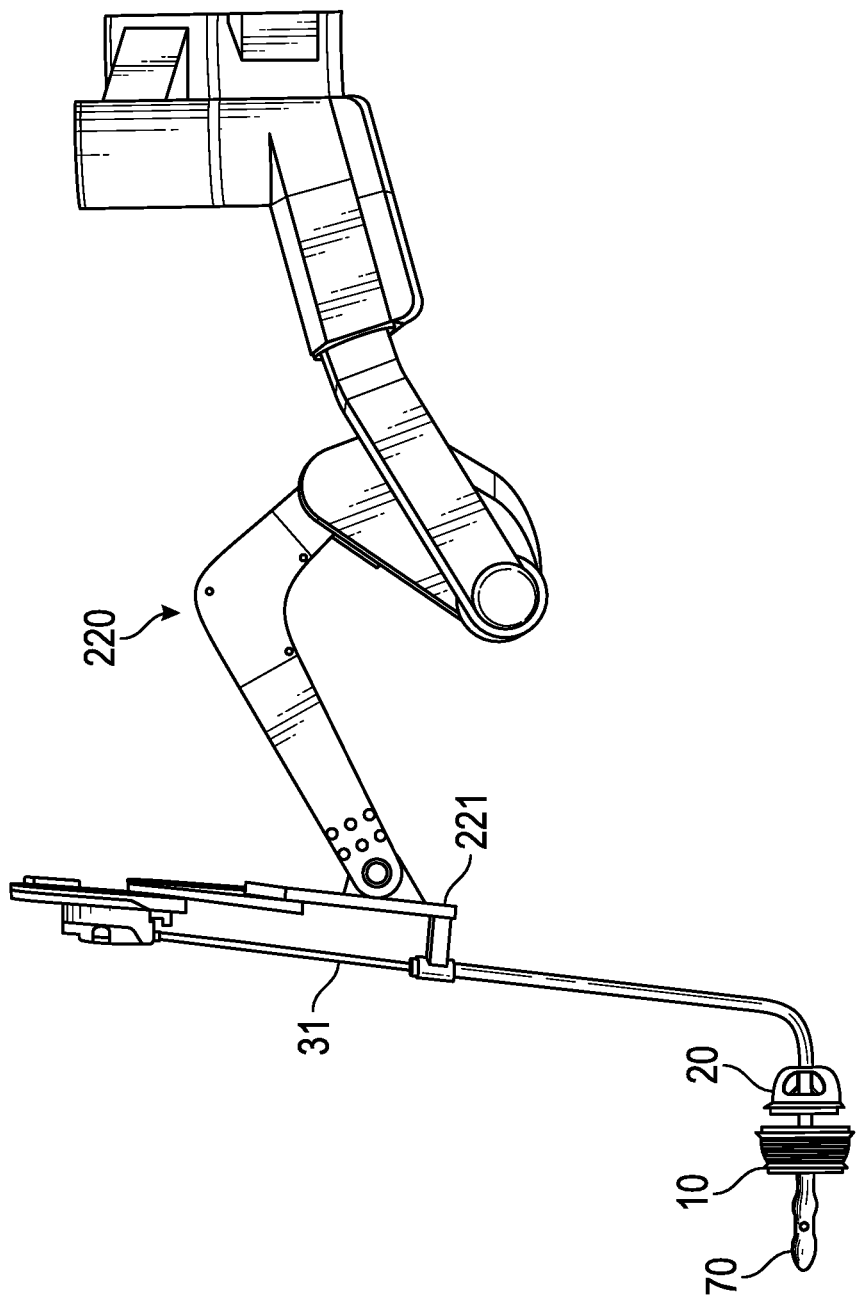
Figure 16E:
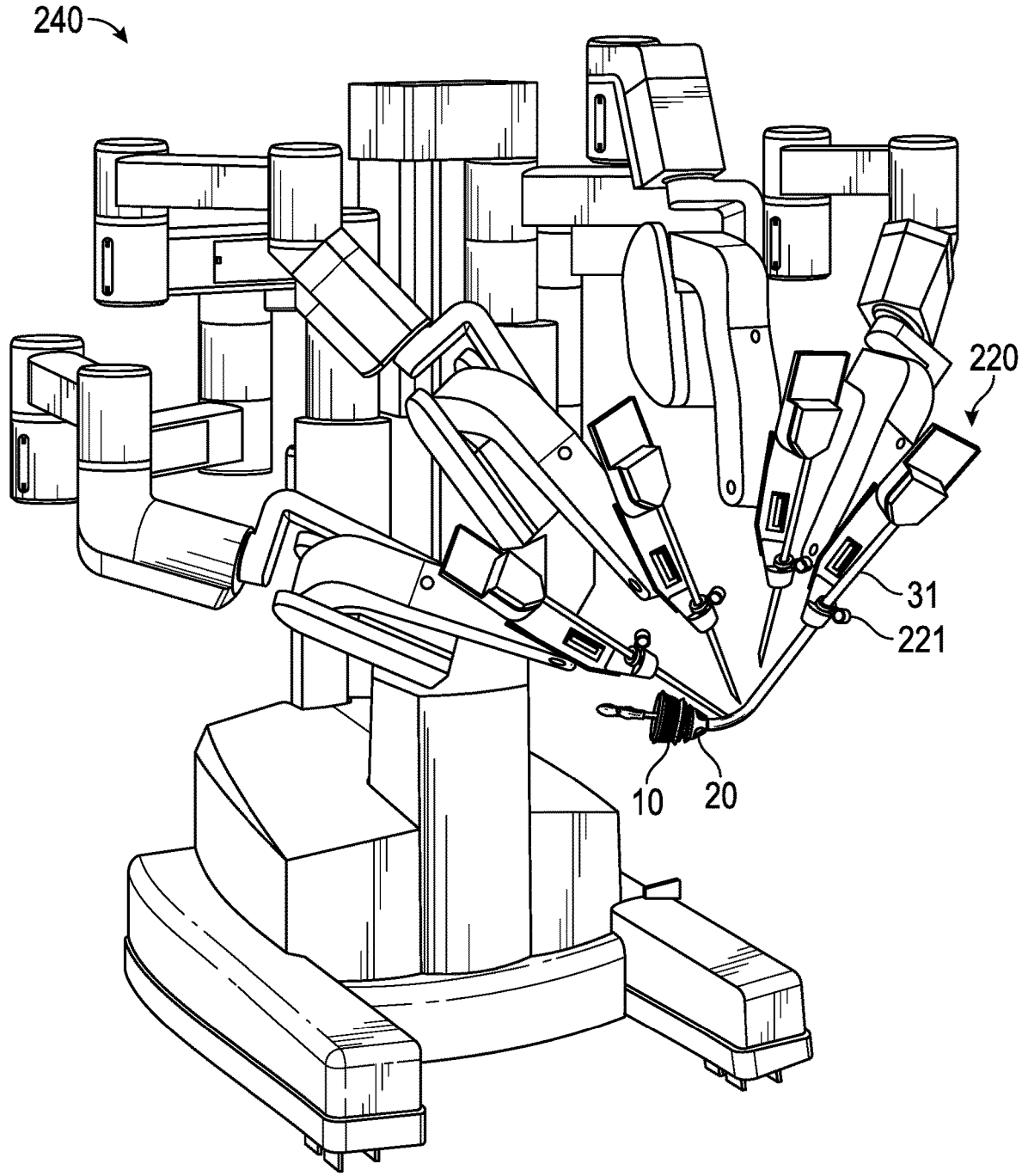

The arm 200 may be comprised of a robotic arm part of a robotic surgery platform. In robotic surgery, an automated arm leads to automated movements of the uterine manipulator system 30, as shown in FIGS. 16E-16D.

Alternatively, the arm may have an attachment point 202, which clamps, screws or affixes onto an operating table, as shown in FIG. 16A. Alternatively the attachment point 202 may attach to a patient's extremities, such as legs. FIG. 16C shows an arm 200 attached to a plate 95, which the patient's body rests upon and is therefore immobile due to the gravitational force of the patient's body. The plate may be affixed to the operating table 98 via a strap(s) 99 or other fixing mechanism to ensure it is immobile. Alternatively, the strap may encircle the patient and be secured via a knot, velcro or other fixing mechanism. The plate 95 may be any circular, oval, rectangular, square, polygonal or other mixed shape ARTICULATION SYSTEM The uterine manipulator system 30 or dye delivery system may include a fulcrum 50 comprised of a linkage to assist in articulation of the uterine manipulator. The linkage may include, for example, a collection of rigid shafts interconnected by pivots and/or clamps to enable selected ranges of motion. The selected ranges of motion are adapted to extend within a three-space envelope needed or expected to be needed for the uterus undergoing the procedure.

The linkage, for example, may include an arm 200, as shown in FIG. 16A and FIG. 16B, such as a Martin's arm). The arm includes an attachment point 202 comprised of a clamp, a right angle shaft 204, a secondary shaft 206, a tertiary shaft 208 and an end clamp 210. The attachment point 202 is configured to fix the arm 200 to a fixed surface in proximity to the patient, such as an operating table.

The attachment point 202 may connect to the right angle shaft at a first end and may have two degrees of freedom. The attachment point 202 may include a rotational component that can be freed or fixed with a locking knob. The attachment point 202 may also include a second locking knob that allows sliding translation of the right angle shaft 204.

The right angle shaft 204 may have a long portion 204a configured to extend through a linear opening 202a defined in the attachment point 202. The right angle shaft may include a short portion 204b extending at a right angle to the long portion 204a and supporting a ball at its free end. The long portion 204a of the right angle shaft 204 may be sized and shaped to extend vertically the anterior-posterior thickness of a patient reclined on the operating table. The short portion 204b of the right angle shaft 204 may be sized to partially close the distance between the table's edge and the patient's uterus.

The secondary shaft 206 may include a lockable socket 212 at a first end. The lockable socket 212 may be configured to receive the ball at the free end of the right angle shaft 204. The lockable socket 212 may be configured to allow the secondary shaft 206 to move with three rotational degrees of freedom relative to the right angle shaft 204. The lockable socket 212 may be configured for a friction fit with the ball of the right angle shaft 204. The friction fit may be calibrated to allow the health care worker to move the secondary shaft 206 relative to the right angle shaft 204 but to remain relatively fixed when not under hand forces.

The secondary shaft 206 may be a linear shaft and relatively shorter than the long portion of the right angle shaft 204 and about the same length as the shorter portion of the right angle shaft.

The secondary shaft 206 may include a second end with a lockable pivot 214. The lockable pivot 214 may connect the second end of the secondary shaft 206 to a first end of the tertiary shaft. The lockable pivot 214 may include a locking knob 214b configured to fix the single pivoting degree of freedom between the secondary and tertiary shafts.

The tertiary shaft 208 is a linear shaft that may be the same length as the secondary shaft 206. The tertiary shaft 208 may include a second end 208a with a socket similar to the socket of the secondary shaft 206.

The end clamp 210 includes a ball configured to rotate with three degrees of rotational freedom within the socket of the tertiary shaft 208. The end clamp 210 includes a C or U shaped body defining an opening configured to slidably receive a portion or shaft of the uterine manipulator. The end clamp 210 also includes a screw mechanism 216 having a lever at a free end and a locking face at an end extending into the opening of the C or U shaped body of the end clamp 210. The lever may be gripped to rotate the screw and advance the locking face into the portion of the uterine manipulator extending through the opening of the body. The screw mechanism 216 is therefore configured to lock or fix the uterine manipulator into place relative to the end clamp 210.

Once the uterine manipulator is fixed to the end clamp 210, the intervening movable connections between the shafts enable a relatively full range of six degree of freedom motion relative to the patient. At the same time, the healthcare worker can selectively fix the various interconnecting joints to eliminate degrees of freedom and provide for a more controlled manipulation of the uterus. A modified arm 200 with fewer degrees of motion and fewer intervening shafts may be used, as illustrated in FIG. 16F.

Figure 16F:
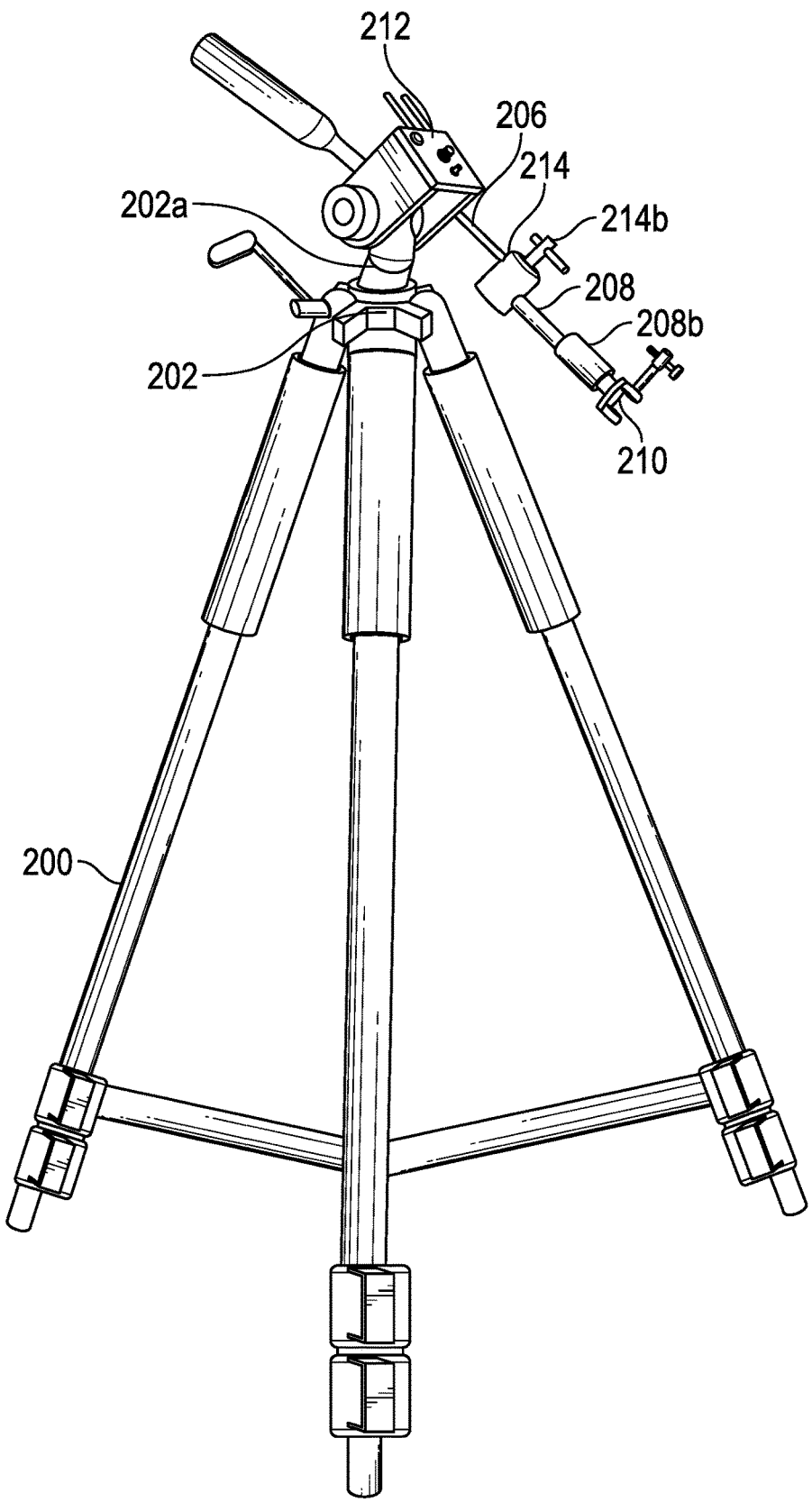

In another embodiment, an arm may be connected to a tripod-like structure, as shown in FIG. 16F. In such an embodiment the tripod legs 200, which may be two or more, would support a base portion 202 and have similar mechanics as a Martin's arm. For example, the height or vertical translation could be controlled by an attachment point 202 and the device could include a secondary shaft 206, a tertiary shaft 208 and an end clamp 210. The secondary shaft 206 may also include a lockable socket 212 at a first end configured to receive the ball at the free end. The lockable socket 212 may be configured to allow the secondary shaft 206 to move with three rotational degrees of freedom. The secondary shaft 206 may also include a second end with a lockable pivot 214. The lockable pivot 214 may connect the second end of the secondary shaft 206 to a first end of the tertiary shaft. The lockable pivot 214 may include a locking knob 214b configured to fix the single pivoting degree of freedom between the secondary and tertiary shafts. The tertiary shaft 208 may include a second end 208a with a socket similar to the socket of the secondary shaft 206. And the end clamp 210 includes a ball configured to rotate with three degrees of rotational freedom within the socket of the tertiary shaft 208. The end clamp 210 includes a C or U shaped body defining an opening configured to slidably receive a portion or shaft of the uterine manipulator. The end clamp 210 also includes a screw mechanism 216 having a lever at a free end and a locking face at an end extending into the opening of the C or U shaped body of the end clamp 210. The lever may be gripped to rotate the screw and advance the locking face into the portion of the uterine manipulator extending through the opening of the body. The screw mechanism 216 is therefore configured to lock or fix the uterine manipulator into place relative to the end clamp 210.

Rather than a hand-operated arm, the linkage 150 may include various motors to form a partial or full robotic system 240. FIG. 16D illustrates a robotic arm 220 coupled to a uterine manipulator system 30 and FIG. 16E illustrates a robotic arm 220 and uterine manipulator system 30 as part of a robotic system. The robotic system may be configured to achieve the same full six degrees of freedom motion within the envelope needed to perform the uterine manipulation. The robotic system may be a generalized robotic arm 220 with an end effector 221 configured to grip or lock onto a portion of the uterine manipulator. The effector 221 also serves as a fulcrum 50. A commercially available robotic arm system, for example, is the da Vinci surgical system sold by Intuitive Surgical. The linkage system need not be commercially available but instead could be selectively combine various dimensions and motorization to best fit the desired amount of precision, motion and control desired by the health care worker.

Not every embodiment of a uterine manipulator system necessarily includes the particular features, structures, or characteristics described in the specification. For example, a uterine manipulator system may be comprised of a shaft 31 and tip and may serve as a simple dye delivery system, as shown in FIG. 8D. The tip 70 may be substituted with a balloon. In other embodiments, the system may also include a fulcrum 50 or fulcrum attachment. Alternatively, the system may also include a stabilizer 20 that may or may not be accompanied by an outer tube 61. In other embodiments, the system may include additionally a collar 10.

The uterine manipulator system and its various embodiments may be packed, sold or delivered as a kit with a surgical tool or device, such as an arm, linkage, robotic arm or any device the facilitates articulation. In addition, one more collars and stabilizers may be sold in a single uterine manipulator kit. For example, such a kit may include one or more collars and one or more stabilizers in addition to a shaft 31, tip 70 and handle 32. Alternatively, a kit may include a shaft 31, tip 70 and handle 32, but the collars and stabilizers are sold separately. The device may come pre-assembled or separately with the system. The kit may include other materials including appropriate labeling, one or more sterile barriers (e.g., 2 barriers), trays, bags, and a box. These other components may be sterile.

All parts may be constructed from a variety of materials, including but not limited to plastic, metal, cloth, textiles, synthetic fibers, nylon, rubber, Silicone (Polydimethylsiloxane), Polyurethane (e.g., Aliphatic Aromatic), Polycarbonate Urethane, Polyvinyl Chloride (PVC), Polyethylene Mesh or Film (e.g, LLDPE, LDPE, HDPE), Polypropylene Mesh or Film, Nylon, Pebax, Polycarbonate, or other materials with other appropriate or similar properties.

Various Examples of Embodiments are Now Discussed.

Example A includes a uterine manipulator, comprising a uterine shaft, collar, and stabilizer; wherein the collar has a first end having a first opening with a rim to encircle the first opening, and a second end having a second opening with a rim to encircle the second opening; the second end having a diameter greater than the first end, and the collar having an inner surface and outer surface to define an inner cavity; and a stabilizer comprising a base portion and a plurality of prongs extending from the base portion; wherein the uterine shaft slides through the base portion of the stabilizer, and the ends of the prongs of the stabilizer contact the collar.

Another example includes the uterine manipulator of Example A, wherein the collar has one of a trapezoid cross-section shape, a domed cross-section shape, polygonal or a combination of a polygonal and domed cross-section shape.

Another example includes the uterine manipulator of Example A, wherein the collar has a plurality of parallel ridges around an outer surface of the collar.

Another example includes the uterine manipulator of Example A, wherein the collar has one of a hole, ring, tab, or other shelf fixed to the collar to receive a strap.

Another example includes the uterine manipulator of Example A, wherein one or more rims include an outer edge, an inner edge, and a rim surface between the outer edge and the inner edge to define the opening, and the rim surface is angled with respect to a plane defined by the outer edge.

Another example includes the uterine manipulator of Example A, wherein one or more rims include a shelf extending inward toward a middle portion of the collar from the first end.

Another example includes the uterine manipulator of Example A, wherein one or more rims comprise a first outer rim edge adjacent to the first opening and a second outer rim edge separated from the first outer rim edge by a gully.

Another example includes the uterine manipulator of Example A, wherein the base portion of the stabilizer has a guide hole. Another example may include the subject matter of the immediately preceding example, wherein the ends of the prongs contact a gully on the inner surface between the second outer rim edge and collar wall.

Another example includes the uterine manipulator of Example A, wherein the ends of the prongs contact an inner surface of the collar.

Another example includes the uterine manipulator of Example A, wherein the ends of the prongs of the stabilizer contact a rim of the collar.

Example B includes the uterine manipulator of Example A, wherein the stabilizer includes a stabilizer rim connecting the ends of the prongs that are opposite the base portion. Another example includes the uterine manipulator of Example B, wherein the stabilizer rim contacts the inner surface of the collar. Another example includes the uterine manipulator of Example B, wherein the stabilizer rim contacts a rim of the collar. Another example includes the uterine manipulator of Example B, wherein the stabilizer rim contacts a gully on the inner surface between an outer rim edge and collar wall.

Example C includes the uterine manipulator of Example A, wherein the inner surface of the collar wall includes one or more shelves. Another example includes the uterine manipulator of Example C, wherein the stabilizer rim contacts a shelf on the inner surface of the collar wall. Another example includes the uterine manipulator of Example C, wherein the stabilizer prongs contacts a shelf on the inner surface of the collar wall. Another example includes the uterine manipulator of Example C, wherein the shelves contain additional angled shelves. Another example includes the uterine manipulator of Example C, wherein the shelf(s) constitutes a circular inner rim or edge along the inner surface of the collar wall. Another example includes the uterine manipulator of Example C, wherein the shelf(s) is located at the midpoint between the inner and outer end of the collar.

Another example includes the uterine manipulator of Example A, wherein the stabilizer rim includes an outer edge, an inner edge, and a rim surface between the outer edge and the inner edge to define the opening.

Another example includes the uterine manipulator of Example A, wherein the stabilizer rim comprises a first outer rim edge adjacent to the first opening and a second outer rim edge separated from the first outer rim edge by a gully.

Another example includes the uterine manipulator of Example A, wherein the stabilizer prongs extend from the base portion to form one of a "U" shape, a "V" shape, or a wishbone shape, with the base portion located at a center point of the "U," the "V", and the wishbone, respectively.

Another example includes the uterine manipulator of Example A, wherein ends of the plurality of prongs opposite the base portion of the stabilizer are not mechanically connected to each other.

Another example includes the uterine manipulator of Example A, wherein the base portion of the stabilizer is connected to a hollow tube.

Another example includes the uterine manipulator of Example A, wherein a pressing portion including a screw and fixing portion slide over the uterine shaft.

Example D includes the uterine manipulator of Example A, wherein the shaft includes an inlet at one end an outlet at the opposite end. Another example includes the uterine manipulator of Example D, wherein the inlet is a luer lock. Another example includes the uterine manipulator of Example D, wherein the inlet includes a cap. Another example includes the uterine manipulator of Example D, wherein the outlet is a hole on the sidewall of the shaft. Another example includes the uterine manipulator of Example D, wherein the end containing the outlet has a screw portion. Another example includes the uterine manipulator of Example D, wherein the outlet is a hole on the sidewall of the shaft.

Example E includes the uterine manipulator of Example D, wherein the outlet end of the shaft includes a tip. Another example includes the uterine manipulator of Example E, wherein the tip is detachable. Another example includes the uterine manipulator of Example E, wherein the tip includes one or more holes. Another example includes the uterine manipulator of the immediately preceding example, wherein the holes are on the sidewalls of the tip. Another example includes the uterine manipulator of Example E, wherein the tip has an hourglass, dumbbell, or curved shape. Another example includes the uterine manipulator of Example A, wherein the tip has a ribbed portion.

Another example includes the uterine manipulator of Example A, wherein the shaft includes a handle. Another example includes the uterine manipulator of the immediately preceding example, wherein the handle has a marking, ridge, compass, or shelf.

Example 1 includes a uterine manipulator system comprising: (1) a collar including (a)(i) a first end comprising a first opening, having a first diameter, surrounded by a first rim, (a)(ii) a second end, opposite the first end, having a second opening, having a second diameter that is larger than the first diameter, surrounded by a second rim, (a)(iii) an inner surface, coupling the first end to the second end, adapted to contact a cervix, (a)(iv) an outer surface adapted to contact a vaginal wall, (a)(v) a hollow tunnel, including the inner surface, the first opening, and the second opening wherein the hollow tunnel is adapted to receive the cervix; and (a)(vi) a first shelf connected to the inner surface and located between the first and second ends; and wherein the first shelf includes a first surface and a second surface opposite the first surface, the first surface being between the second surface and the first end and the second surface being between the second end and the first surface; (2) a stabilizer including (b)(i) a first stabilizer end comprised of a base portion with a stabilizer aperture, (b)(ii) a second stabilizer end, opposite the first stabilizer end, having a stabilizer rim adapted to couple to the first shelf or the second shelf, wherein a diameter of the first stabilizer end is less than a diameter of the second stabilizer end; (3) a shaft configured to pass through the stabilizer aperture; wherein the shaft contains a hollow inner channel coupling a distal end of the shaft to a proximal end of the shaft; and wherein the distal end of the shaft includes at least one of a distal shaft aperture in fluid communication with the hollow inner channel, and the proximal end of the shaft includes at least one of a proximal shaft aperture in fluid communication with the hollow inner channel; (4) a bulbous portion having a maximum bulbous diameter greater than a maximum diameter of the shaft; wherein the bulbous portion includes a first portion, a second portion, and a third portion; wherein the second portion is located between the first portion and the third portion; wherein the first portion is configured for coupling to the distal end of the shaft; wherein the first portion, the second portion, and the third portion respectively include a first diameter, a second diameter, and a third diameter; wherein the second diameter is smaller than the first diameter and the third diameter; and wherein at least one or more of a bulbous portion aperture is located on the second portion and is in fluid communication with the distal shaft aperture and the hollow inner channel.

In example 2, the subject matter of Example 1 can optionally include a first rim including a first inner edge, separated by a first gully from a first outer edge; wherein the second rim includes a second inner edge, separated by a second gully from a second outer edge; wherein the first outer edge is closer than the first inner edge to the second outer edge in a linear direction; wherein the second outer edge is closer than the second inner edge to the first outer edge in a linear direction; and wherein the first outer edge is farther from a center of the collar in a radial direction than the first inner edge; and the second outer edge is farther from the center of the collar in a radial direction than the second inner edge.

In example 3, the subject matter of Examples 1-2 can optionally include a first rim with a diameter between 25 mm and 40 mm; wherein the diameter of the second rim is between 25 mm and 45 mm; wherein the diameter of the stabilizer rim is between 15 mm and 35 mm; wherein the distance between the first end and second end is less than 40 mm; and wherein the first diameter and the third diameter is 5 mm to 10 mm.

Example 4 includes a uterine manipulator system comprising: a collar including (a)(i) a first end comprising a first opening, having a first diameter, surrounded by a first rim, (a)(ii) a second end, opposite the first end, having a second opening, having a second diameter that is larger than the first diameter, surrounded by a second rim, (a)(iii) an inner surface, coupling the first end to the second end, adapted to contact a cervix, (a)(iv) an outer surface adapted to contact a vaginal wall, (a)(v) a hollow tunnel, including the inner surface, the first opening, and the second opening wherein the hollow tunnel is adapted to receive the cervix; and (a)(vi) a first shelf connected to the inner surface and located between the first and second ends; wherein the first shelf includes a first surface and a second surface opposite the first surface, the first surface being between the second surface and the first end and the second surface being between the second end and the first surface; and a stabilizer including (b)(i) a first stabilizer end comprised of a base portion with a stabilizer aperture, (b)(ii) a second stabilizer end, opposite the first stabilizer end, having a stabilizer rim adapted to couple to the first shelf or the second shelf, wherein a diameter of the first stabilizer end is less than a diameter of the second stabilizer end.

In example 5, the subject matter of Example 4 can optionally include a shaft configured to pass through the stabilizer aperture; wherein the shaft contains a hollow inner channel coupling a distal end of the shaft to a proximal end of the shaft; wherein the proximal end of the shaft includes at least one of a proximal shaft aperture in fluid communication with the hollow inner channel; and wherein the shaft includes a middle portion between the proximal end of the shaft and the distal end of the shaft.

In example 6, the subject matter of Examples 4-5 can optionally include the middle portion with a middle portion long axis and the distal end with a distal end long axis that intersects the middle portion long axis at an intersection angle between 0 to 90 degrees.

In example 7, the subject matter of Examples 4-6 can optionally include the stabilizer with at least one of a window between the stabilizer rim and the base portion.

In example 8, the subject matter of Examples 4-7 can optionally include a first configuration wherein the stabilizer rim couples to the first surface and not the second surface; and a second configuration wherein the stabilizer rim couples to the second surface and not the first surface.

In example 9, the subject matter of Examples 4-8 can optionally include a second shelf connected to the inner surface and located between the second end and the first shelf; wherein in a first configuration the stabilizer rim connects directly to the first shelf and not the second shelf; and wherein in a second configuration the stabilizer rim connects directly to the second shelf and not the first shelf.

In example 10, the subject matter of Examples 4-9 can optionally include the inner surface of the collar including two or more inner shelves; and wherein the stabilizer rim is configured to couple to at least one inner shelf.

In example 11, the subject matter of Examples 5-10 can optionally include the distal end of the shaft including a bulbous portion having a maximum bulbous diameter greater than a maximum diameter of the shaft; wherein the maximum bulbous diameter is adapted to resist withdrawal of the distal end from the cervix; and wherein at least one or more of a bulbous portion aperture is located on the bulbous portion and is in fluid communication with the proximal shaft aperture and the hollow inner channel.

In example 12, the subject matter of Examples 11 can optionally include the bulbous portion including a first portion, a second portion, and a third portion; wherein the second portion is located between the first portion and the third portion; wherein the first portion is configured for coupling to the distal end of the shaft; wherein the first portion, the second portion, and the third portion respectively include a first diameter, a second diameter, and a third diameter; wherein the second diameter is smaller than the first diameter and the third diameter; and wherein the second portion includes at least one or more of the bulbous portion aperture.

In example 13, the subject matter of Examples 5-12 can optionally include a fulcrum configured to slidably couple to the shaft, wherein the shaft pivots about the fulcrum; wherein the fulcrum is selected from the group comprising a disc, a plate, a ball, a rim with prongs, and a sponge; and wherein the fulcrum is configured to fit within a vaginal canal that comprises the vaginal wall; and wherein the fulcrum contains a hole to receive the shaft.

In example 14, the subject matter of Examples 5-13 can optionally include a fulcrum configured to slidably couple to the shaft and wherein the shaft pivots about the fulcrum and a powered linkage configured to articulate the system; wherein the linkage is a robotic arm configured to articulate the system through six degrees of freedom; and wherein the powered linkage includes an end effector configured to interface with the system.

In example 15, the subject matter of Examples 12-14 can optionally include a conduit wherein the conduit is hollow with an inner diameter greater than the diameter of the stabilizer aperture and a diameter of the shaft; wherein the distal end of the conduit is configured couple to the base portion; wherein the conduit is configured to slide between the proximal end of the shaft and the distal end of the shaft; and wherein the base portion is distal to the conduit, and one or more of the bulbous portion aperture is distal to the stabilizer.

In example 16, the subject matter of Example 15 can optionally include a proximal end of the conduit adapted to couple to a fastener to fixedly fasten the conduit to the shaft.

In example 17, the subject matter of Examples 5-16 can optionally include the middle portion including a middle portion long axis and the distal end including a distal end long axis that intersects the middle portion long axis; and wherein the angle between the two axis is adjustable and the curvature of the shaft is malleable.

In example 18, the subject matter of Examples 12-17 can optionally include the diameter of the first rim being between 25 mm and 40 mm; wherein the diameter of the second rim is between 25 mm and 45 mm; the diameter of the stabilizer rim is between 15 mm and 35 mm; the distance between the first end and second end is less than 40 mm; and the first diameter and the third diameter is 5 mm to 10 mm.

Example 19 includes a uterine manipulator system comprising: (1) a shaft configured to pass through the stabilizer aperture; wherein the shaft contains a hollow inner channel coupling a distal end of the shaft to a proximal end of the shaft; and wherein the distal end of the shaft includes at least one of a distal shaft aperture in fluid communication with the hollow inner channel, and the proximal end of the shaft includes at least one of a proximal shaft aperture in fluid communication with the hollow inner channel; (2) a bulbous portion having a maximum bulbous diameter greater than a maximum diameter of the shaft; wherein the bulbous portion includes a first portion, a second portion, and a third portion; wherein the second portion is located between the first portion and the third portion; wherein the first portion is configured for coupling to the distal end of the shaft; wherein the first portion, the second portion, and the third portion respectively include a first diameter, a second diameter, and a third diameter; wherein the second diameter is smaller than the first diameter and the third diameter; wherein at least one or more of a bulbous portion aperture is located on the second portion and is in fluid communication with the distal shaft aperture and the hollow inner channel; and wherein the maximum first diameter and third diameter is 5 mm to 10 mm.

In example 20, the subject matter of Example 19 can optionally include (1) a stabilizer comprising (a)(i) a first stabilizer end comprised of a base portion with a stabilizer aperture, (a)(ii) a second stabilizer end, opposite the first stabilizer end; wherein a diameter of the first stabilizer end is less than a diameter of the second stabilizer end; wherein in a first configuration the stabilizer aperture is slidable along the shaft; wherein one or more of the bulbous portion aperture is distal to the stabilizer; and (2) a conduit wherein the conduit is hollow with an inner diameter greater than the diameter of the stabilizer aperture and a diameter of the shaft; wherein the distal end of the conduit is configured couple to the base portion; wherein the conduit is configured to slide between the proximal end of the shaft and the distal end of the shaft; wherein the base portion is distal to the conduit, and one or more of the bulbous portion aperture is distal to the stabilizer; and wherein a proximal end of the conduit is adapted to couple to a fastener to fixedly fasten the conduit to the shaft.

In example 21, the subject matter of Examples 6-18 can optionally include the proximal end of the shaft being collinear with the middle portion and the intersection angle is adjustable.

In example 22, the subject matter of Examples 5-18 can optionally include the distal end of the shaft including a first portion, a second portion, and a third portion wherein the second portion is located between the first portion and the third portion, the first portion being proximal to the second portion; wherein the first portion, the second portion, and the third portion respectively include a first diameter, a second diameter, and a third diameter, and the second diameter is less than the first diameter and the third diameter; and wherein the first diameter is greater than a maximum diameter of the shaft.

In example 23, the subject matter of Examples 22 can optionally include one or more of the distal shaft aperture included in the second portion.

In example 24, the subject matter of Examples 23 can optionally include a first configuration wherein the stabilizer aperture is slidable along the shaft; and wherein one or more of the distal shaft aperture is distal to the collar, and the collar is distal to the stabilizer.

In example 25, the subject matter of Examples 4-18 can optionally include the stabilizer including at least one of a window between the stabilizer rim and the base portion, and between two or more prongs that couple the base portion to the stabilizer rim.

In example 26, the subject matter of Examples 11-18 can optionally include the bulbous portion including a first portion, a second portion, and a third portion; wherein the second portion is located between the first portion and the third portion; wherein the first portion is configured for coupling to the distal end of the shaft; wherein the first portion, the second portion, and the third portion respectively include a first diameter, a second diameter, and a third diameter; wherein the second diameter is smaller than the first diameter and the third diameter; and wherein a distal tip of the third portion includes at least one or more of the bulbous portion aperture.

In example 27, the subject matter of Examples 14-18 can optionally include the fulcrum adapted for use with a vaginal retractor or a speculum.

In example 28, the subject matter of Examples 17-18 can optionally include the fastener including at least one of a set screw or a stop collar.

In example 29, the subject matter of Examples 16-18 can optionally include a disc configured to couple to the distal end of the conduit and the base portion.

In example 30, the subject matter of Examples 5-18 can optionally include a strap or string configured for attachment to the collar.

In example 31, the subject matter of Example 30 can optionally include the collar having a hole, a ring or a protrusion to receive the strap or the string.

In example 32, the subject matter of Examples 5-18 can optionally include a handle coupled to the proximal end of the shaft, the handle including a projection that projects orthogonally to a long axis of the proximal end of the shaft.

In example 33, the subject matter of Examples 32 can optionally include the projection including a pointed end.

In example 34, the subject matter of Examples 13-18 can optionally include the fulcrum configured to connect to an arm with six degrees of freedom.

In example 35, the subject matter of Examples 34 can optionally include the arm configured to attach to a table, a robotic platform, a plate, a pad, a sled, or a fixed point.

In example 36, the subject matter of Examples 5-18 can optionally include a linkage configured to articulate the system.

In example 37, the subject matter of Example 36 can optionally include the linkage including at least one degree of freedom for articulating the system.

In example 38, the subject matter of Example 37 can optionally include the degree of freedom being rotation approximately within a sagittal plane of the patient.

In example 39, the subject matter of Example 38 can optionally include wherein approximately within the sagittal plane of the patient is within plus or minus 5 degrees of the sagittal plane.

In example 40, the subject matter of Example 39 can optionally include the linkage configured to articulate the system through six degrees of freedom.

In example 41, the subject matter of Example 40 can optionally include the linkage configured to selectively lock relative motion of its links.

In example 42, the subject matter of Example 37 can optionally include the linkage being a powered linkage configured to articulate the system.

In example 43, the subject matter of Example 42 can optionally include the powered linkage including an end effector configured to interface with the system.

In example 44, the subject matter of Example 43 can optionally include the powered linkage being a robotic arm having six degrees of freedom In example 45, the subject matter of Example 5 can optionally include a sponge configured to slidably couple to the shaft.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A uterine manipulator system comprising:
   a collar including (a)(i) a first end comprising a first opening, having a first diameter, surrounded by a first rim, (a)(ii) a second end, opposite the first end, having a second opening, having a second diameter that is larger than the first diameter, surrounded by a second rim, (a)(iii) an inner surface, coupling the first end to the second end, adapted to contact a cervix, (a)(iv) an outer surface adapted to contact a vaginal wall, (a)(v) a hollow tunnel, including the inner surface, the first opening, and the second opening wherein the hollow tunnel is adapted to receive the cervix; and (a)(vi) a first shelf connected to the inner surface and located between the first and second ends wherein the collar is reversible to operate in a first orientation and a second orientation, wherein the first rim and the second rim is adapted to contact a fornix;
   wherein the first shelf includes a first surface and a second surface opposite the first surface, the first surface being between the second surface and the first end and the second surface being between the second end and the first surface; and a stabilizer including (b)(i) a first stabilizer end comprised of a base portion with a stabilizer aperture, (b)(ii) a second stabilizer end, opposite the first stabilizer end, having a stabilizer rim adapted to couple to the first surface and the second surface, wherein a diameter of the first stabilizer end is less than a diameter of the second stabilizer end, wherein in the first orientation the first rim is configured to be coupled to the stabilizer and in the second orientation the second rim is configured to be coupled to the stabilizer.

2. The system of claim 1 comprising (1) a shaft configured to pass through the stabilizer aperture;

wherein the shaft contains a hollow inner channel coupling a distal end of the shaft to a proximal end of the shaft;

wherein the distal end of the shaft includes at least one of a distal shaft aperture in fluid communication with the hollow inner channel, and the proximal end of the shaft includes at least one of a proximal shaft aperture in fluid communication with the hollow inner channel; and wherein the shaft includes a middle portion between the proximal end of the shaft and the distal end of the shaft;

(2) a bulbous portion having a maximum bulbous diameter greater than a maximum diameter of the shaft including a longitudinal axis;

wherein the bulbous portion includes a first portion, a second portion, and a third portion, wherein the second portion is located between the first portion and the third portion;

wherein the first portion is configured for coupling to the distal end of the shaft wherein the first portion, the second portion, and the third portion respectively include a first diameter, a second diameter, and a third diameter, wherein the bulbous portion includes a continuously convexly sloped perimeter extending from the third diameter and crossing the longitudinal axis to form a closed, rounded distal end of the bulbous portion;

wherein the second diameter is smaller than the first diameter and the third diameter; and wherein a first outlet is located between the second portion and the distal end of the bulbous portion, and the first outlet is in fluid communication with the distal shaft aperture and the hollow inner channel.

3. The system of claim 2:

wherein the middle portion includes a middle portion long axis and the distal end includes a distal end long axis that intersects the middle portion long axis at an intersection angle between 0 to 90 degrees.

4. The system of claim 2, wherein the maximum bulbous diameter is configured to resist withdrawal of the distal end from the cervix, wherein the first outlet is located on the bulbous portion and is in fluid communication with the proximal shaft aperture and the hollow inner channel.

5. The system of claim 2 including a fulcrum configured to slidably couple to the shaft.

6. The system of claim 5 wherein the fulcrum is selected from the group comprising a disc, a plate, a ball, a rim with prongs, and a sponge.

7. The system of claim 5 wherein the fulcrum is configured to fit within a vaginal canal that comprises the vaginal wall.

8. The system of claim 5 wherein the fulcrum contains a hole to receive the shaft.

9. The system of claim 2 including a fulcrum configured to slidably couple to the shaft and wherein the shaft pivots about the fulcrum and a powered linkage configured to articulate the system.

10. The system of claim 2 having a conduit wherein the conduit is hollow with an inner diameter greater than the diameter of the stabilizer aperture and a diameter of the shaft;

wherein the distal end of the conduit is configured couple to the base portion;

wherein the conduit is configured to slide between the proximal end of the shaft and the distal end of the shaft; and wherein the base portion is distal to the conduit, and the first outlet is distal to the stabilizer.

11. The system of claim 10, wherein a proximal end of the conduit is adapted to couple to a fastener to fixedly fasten the conduit to the shaft.

12. The system of claim 2:

wherein the middle portion includes a middle portion longitudinal axis and the distal end includes a distal end longitudinal axis that intersects the middle portion longitudinal axis; and wherein the angle between the two axis is adjustable and the curvature of the shaft is malleable.

13. The system of claim 1 wherein the stabilizer includes at least one of a window between the stabilizer rim and the base portion.

14. The system of claim 1, wherein in a first configuration the stabilizer rim couples to the first surface and not the second surface; and wherein in a second configuration the stabilizer rim couples to the second surface and not the first surface.

15. The system of claim 1 comprising a second shelf connected to the inner surface and located between the second end and the first shelf;

wherein in a first configuration the stabilizer rim connects directly to the first shelf and not the second shelf; and wherein in a second configuration the stabilizer rim connects directly to the second shelf and not the first shelf.

16. The system of claim 1, wherein the inner surface of the collar includes two or more inner shelves; and wherein the stabilizer rim is configured to couple to at least one inner shelf.

17. The system of claim 1:

wherein a diameter of the first rim is between 25 mm and 40 mm;

wherein a diameter of the second rim is between 25 mm and 45 mm;

wherein a diameter of the stabilizer rim is between 15 mm and 35 mm;

wherein a distance between the first end and second end is less than 40 mm; and wherein the first diameter and the third diameter is 5 mm to 10 mm.

18. A uterine manipulator system comprising:

(1) a shaft;

wherein the shaft contains a hollow inner channel coupling a distal end of the shaft to a proximal end of the shaft; and wherein the distal end of the shaft includes at least one of a distal shaft aperture in fluid communication with the hollow inner channel, and the proximal end of the shaft includes at least one of a proximal shaft aperture in fluid communication with the hollow inner channel;

(2) a bulbous portion having a maximum bulbous diameter greater than a maximum diameter of the shaft;

wherein the bulbous portion includes a first portion, a second portion, a third portion, and a longitudinal axis;

wherein the second portion is located between the first portion and the third portion;

wherein the first portion is configured for coupling to the distal end of the shaft;

wherein the first portion, the second portion, and the third portion respectively include a first diameter, a second diameter, and a third diameter;

wherein the second diameter is smaller than the first diameter and the third diameter;

wherein the bulbous portion includes a continuously convexly sloped perimeter extending from the third diameter and crossing the longitudinal axis to form a closed, rounded distal end of the bulbous portion, wherein a first outlet is located on the continuously sloped perimeter between the second diameter and the distal end of the bulbous portion and is in fluid communication with the distal shaft aperture and the hollow inner channel, wherein the bulbous portion does not include an additional inlet and corresponding outlet extending in parallel to a longitudinal axis of the shaft between the first portion and the second portion.

19. The system of 18, including:

(1) a stabilizer comprising (a) (i) a first stabilizer end comprised of a base portion with a stabilizer aperture, (a)(ii) a second stabilizer end, opposite the first stabilizer end;

wherein a diameter of the first stabilizer end is less than a diameter of the second stabilizer end;

wherein in a first configuration the stabilizer aperture is slidable along the shaft;

wherein the first outlet is distal to the stabilizer; and (2) a conduit wherein the conduit is hollow with an inner diameter greater than the diameter of the stabilizer aperture and a diameter of the shaft;

wherein the distal end of the conduit is configured couple to the base portion;

wherein the conduit is configured to slide between the proximal end of the shaft and the distal end of the shaft;

wherein the base portion is distal to the conduit, and the first outlet is distal to the stabilizer; and wherein a proximal end of the conduit is adapted to couple to a fastener to fixedly fasten the conduit to the shaft.

\* \* \* \* \*